(12) United States Patent
Mizuki et al.

(10) Patent No.: US 9,923,146 B2
(45) Date of Patent: *Mar. 20, 2018

(54) AROMATIC AMINE DERIVATIVE AND ORGANIC ELECTROLUMINESCENT ELEMENT USING SAME

(71) Applicant: IDEMITSU KOSAN CO., LTD., Tokyo (JP)

(72) Inventors: Yumiko Mizuki, Sodegaura (JP); Masahiro Kawamura, Sodegaura (JP); Sayaka Mizutani, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/644,675

(22) Filed: Jul. 7, 2017

(65) Prior Publication Data

US 2017/0309822 A1 Oct. 26, 2017

Related U.S. Application Data

(63) Continuation of application No. 15/045,496, filed on Feb. 17, 2016, which is a continuation of application No. 13/138,443, filed as application No. PCT/JP2010/007269 on Dec. 15, 2010, now Pat. No. 9,331,285.

(30) Foreign Application Priority Data

Dec. 16, 2009 (JP) .................. 2009-284969

(51) Int. Cl.
| | |
|---|---|
| H01L 51/00 | (2006.01) |
| C07D 303/00 | (2006.01) |
| C09K 11/06 | (2006.01) |
| C07C 211/54 | (2006.01) |
| C09K 11/02 | (2006.01) |
| H05B 33/14 | (2006.01) |
| C07F 7/08 | (2006.01) |
| C07D 235/08 | (2006.01) |
| C07C 255/58 | (2006.01) |
| C07C 211/61 | (2006.01) |
| H01L 51/50 | (2006.01) |

(52) U.S. Cl.
CPC .......... *H01L 51/006* (2013.01); *C07C 211/54* (2013.01); *C07C 211/61* (2013.01); *C07C 255/58* (2013.01); *C07D 235/08* (2013.01); *C07F 7/0818* (2013.01); *C09K 11/025* (2013.01); *C09K 11/06* (2013.01); *H01L 51/0054* (2013.01); *H01L 51/0058* (2013.01); *H01L 51/0073* (2013.01); *H01L 51/0094* (2013.01); *H05B 33/14* (2013.01); *C07C 2603/24* (2017.05); *C07C 2603/50* (2017.05); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/5012* (2013.01)

(58) Field of Classification Search
CPC ... C07C 211/54; C07C 211/61; C07C 255/58; C07C 2603/24; C07C 2603/50; C07D 235/08; C07F 7/0818; C09K 11/025; C09K 11/06; C09K 2211/1007; C09K 2211/1011; C09K 2211/1014; C09K 2211/1029; C09K 2211/1088; C09K 2211/1092; H01L 51/0054
See application file for complete search history.

(56) References Cited

U.S. PATENT DOCUMENTS

| | | | |
|---|---|---|---|
| 5,759,444 | A | 6/1998 | Enokida et al. |
| 7,732,063 | B2 | 6/2010 | Matsuura et al. |
| 7,839,074 | B2 | 11/2010 | Ikeda et al. |
| 7,927,716 | B2 | 4/2011 | Matsuura et al. |
| 8,592,051 | B2 | 11/2013 | Funahashi |
| 2003/0050489 | A1 | 3/2003 | Abe et al. |
| 2003/0077480 | A1 | 4/2003 | Hosokawa et al. |
| 2003/0118866 | A1 | 6/2003 | Oh et al. |
| 2003/0186144 | A1 | 10/2003 | Kunieda et al. |

(Continued)

FOREIGN PATENT DOCUMENTS

| | | |
|---|---|---|
| DE | 10002561 A1 | 7/2001 |
| DE | 10 2004 029 695 A1 | 1/2006 |

(Continued)

*Primary Examiner* — Dawn L Garrett

(74) *Attorney, Agent, or Firm* — Foley & Lardner LLP

(57) ABSTRACT

An aromatic amine derivative represented by the following formula (1):

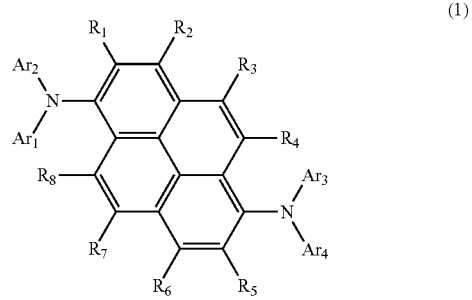

wherein at least one of $R_1$ to $R_8$ is a group other than a hydrogen atom, $Ar_1$ to $Ar_4$ are a substituted or unsubstituted aryl group having 6 to 30 ring carbon atoms.

18 Claims, No Drawings

(56) References Cited

U.S. PATENT DOCUMENTS

| | | |
|---|---|---|
| 2004/0053069 A1 | 3/2004 | Sotoyama et al. |
| 2004/0137270 A1 | 7/2004 | Seo et al. |
| 2005/0064233 A1 | 3/2005 | Matsuura et al. |
| 2006/0033421 A1 | 2/2006 | Matsuura et al. |
| 2006/0043858 A1 | 3/2006 | Ikeda et al. |
| 2006/0134456 A1 | 6/2006 | Ikeda et al. |
| 2007/0009758 A1 | 1/2007 | Funahashi |
| 2007/0060777 A1 | 3/2007 | Moriwaki et al. |
| 2007/0063638 A1 | 3/2007 | Tokairin et al. |
| 2007/0090755 A1 | 4/2007 | Eida et al. |
| 2007/0114917 A1 | 5/2007 | Funahashi et al. |
| 2007/0152565 A1 | 7/2007 | Kubota et al. |
| 2007/0172701 A1 | 7/2007 | Tada |
| 2007/0202354 A1 | 8/2007 | Funahashi |
| 2007/0237984 A1 | 10/2007 | Matsuura et al. |
| 2007/0247063 A1 | 10/2007 | Murase et al. |
| 2007/0252511 A1 | 11/2007 | Funahashi |
| 2008/0001123 A1 | 1/2008 | Inoue et al. |
| 2008/0015399 A1 | 1/2008 | Funahashi |
| 2008/0100206 A1 | 5/2008 | Kondo et al. |
| 2008/0111478 A1 | 5/2008 | Lyu et al. |
| 2008/0113101 A1 | 5/2008 | Inoue et al. |
| 2008/0203905 A1 | 8/2008 | Je et al. |
| 2008/0206447 A1 | 8/2008 | Inoue et al. |
| 2008/0315754 A1 | 12/2008 | Kawamura et al. |
| 2009/0131673 A1 | 5/2009 | Tanabe et al. |
| 2009/0134781 A1 | 5/2009 | Jang et al. |
| 2009/0206748 A1 | 8/2009 | Moriwaki et al. |
| 2010/0045170 A1 | 2/2010 | Lee et al. |
| 2010/0052526 A1 | 3/2010 | Je et al. |
| 2010/0117028 A1 | 5/2010 | Takeshima et al. |
| 2010/0187512 A1 | 7/2010 | Ito |
| 2010/0259163 A1 | 10/2010 | Mizuki et al. |
| 2010/0270913 A1 | 10/2010 | Matsuura et al. |
| 2010/0277061 A1 | 11/2010 | Matsuura et al. |
| 2010/0289014 A1 | 11/2010 | Ito et al. |
| 2010/0295030 A1 | 11/2010 | Kawamura |
| 2010/0295445 A1 | 11/2010 | Kuma et al. |
| 2010/0301313 A1 | 12/2010 | Ito et al. |
| 2010/0314615 A1* | 12/2010 | Mizuki ............... C07D 307/91 257/40 |
| 2010/0320452 A1 | 12/2010 | Kawamura |
| 2011/0034744 A1 | 2/2011 | Ikeda et al. |
| 2011/0042660 A1 | 2/2011 | Kawamura et al. |
| 2011/0121268 A1 | 5/2011 | Nagao et al. |
| 2011/0127510 A1 | 6/2011 | Seo et al. |
| 2011/0156016 A1 | 6/2011 | Kawamura et al. |
| 2011/0193064 A1 | 8/2011 | Funahashi |
| 2011/0204339 A1 | 8/2011 | Dobbs et al. |
| 2011/0220886 A1 | 9/2011 | Takeshima et al. |
| 2011/0240125 A1 | 10/2011 | Ikeda et al. |
| 2011/0297923 A1 | 12/2011 | Mizuki et al. |
| 2012/0112169 A1 | 5/2012 | Mizuki et al. |
| 2012/0138918 A1 | 6/2012 | Naraoka et al. |
| 2012/0313511 A1 | 12/2012 | Tsurutani et al. |
| 2014/0034943 A1 | 2/2014 | Mizuki et al. |

FOREIGN PATENT DOCUMENTS

| | | |
|---|---|---|
| EP | 1 146 034 A1 | 10/2001 |
| EP | 2 163 550 | 3/2010 |
| JP | 08-199162 A | 8/1996 |
| JP | 10-072580 A | 3/1998 |
| JP | 10-072581 A | 3/1998 |
| JP | 10-088122 A | 4/1998 |
| JP | 11-265788 A | 9/1999 |
| JP | 2000-239235 A | 9/2000 |
| JP | 2002-124385 A | 4/2002 |
| JP | 2003-229273 A | 8/2003 |
| JP | 2004-006379 A | 1/2004 |
| JP | 2004-075580 A | 3/2004 |
| JP | 2005-314239 A | 11/2005 |
| JP | 2006-128715 A | 5/2006 |
| JP | 2007-063501 A | 3/2007 |
| JP | 2007-077094 A | 3/2007 |
| JP | 2008-214332 A | 9/2008 |
| JP | 2009-016693 A | 1/2009 |
| JP | 2010-034548 A | 2/2010 |
| JP | 2010-150425 A | 7/2010 |
| JP | 2011-023614 A | 2/2011 |
| JP | 2011-093931 A | 5/2011 |
| KR | 10-2007-0105081 A | 10/2007 |
| KR | 10-2007-0115588 A | 12/2007 |
| KR | 10-0793795 B1 | 1/2008 |
| KR | 20090065201 A | 6/2009 |
| KR | 102008007995 | 7/2009 |
| KR | 2009086015 A | 8/2009 |
| KR | 2010002030 A | 1/2010 |
| KR | 2010-0021367 A | 2/2010 |
| KR | 1020100066424 | 6/2010 |
| KR | 2011-0002155 A | 1/2011 |
| KR | 2011-0024695 A | 3/2011 |
| KR | 2011-0029831 A | 3/2011 |
| KR | 1020110099195 A | 9/2011 |
| WO | WO-2004/018587 A1 | 3/2004 |
| WO | WO-2004/018588 A1 | 3/2004 |
| WO | WO-2005/108348 A1 | 11/2005 |
| WO | WO-2006/011879 A1 | 2/2006 |
| WO | WO-2008/143229 A1 | 11/2008 |
| WO | WO-2009/063846 A1 | 5/2009 |
| WO | WO-2009/069537 A1 | 6/2009 |
| WO | WO-2009/081776 A1 | 7/2009 |
| WO | WO-2009/102026 A1 | 8/2009 |
| WO | WO-2009/102054 A1 | 8/2009 |
| WO | WO-2009/107596 A1 | 9/2009 |
| WO | WO-2009/116628 A1 | 9/2009 |
| WO | WO-2009/133917 A1 | 11/2009 |
| WO | WO-2009/142230 A1 | 11/2009 |
| WO | WO-2009/154207 A1 | 12/2009 |
| WO | WO-2010/010924 A1 | 1/2010 |
| WO | WO-2010/013675 A1 | 2/2010 |
| WO | WO-2010/013780 A1 | 2/2010 |
| WO | WO-2010/016405 A1 | 2/2010 |
| WO | WO-2010/052885 A1 | 5/2010 |
| WO | WO-2010/122810 A1 | 10/2010 |

\* cited by examiner ance device using an aromatic amine derivative and an anthracene derivative, and in particular, to an organic electroluminescence device having a high chromatic purity and a long life, and an aromatic amine derivative realizing it.

AROMATIC AMINE DERIVATIVE AND ORGANIC ELECTROLUMINESCENT ELEMENT USING SAME

CROSS-REFERENCE TO RELATED APPLICATIONS

The present application is a continuation of U.S. application Ser. No. 15/045,496, filed Feb. 17, 2017, which is a continuation of U.S. application Ser. No. 13/138,443, filed Aug. 16, 2011, based upon PCT National Stage Application No. PCT/JP2010/007269, filed Dec. 15, 2010, and claims the benefit of priority from Japanese Patent Application No. 2009-284969, filed Dec. 16, 2009, the contents of which are hereby incorporated by reference in their entireties.

TECHNICAL FIELD

The invention relates to an organic electroluminescence device using an aromatic amine derivative and an anthracene derivative, and in particular, to an organic electroluminescence device having a high chromatic purity and a long life, and an aromatic amine derivative realizing it.

BACKGROUND ART

An organic electroluminescence (EL) device using an organic substance is a promising solid-state emitting type inexpensive and large full-color display device, and has been extensively developed. In general, an organic EL device includes an emitting layer and a pair of opposing electrodes holding the emitting layer therebetween. When an electric field is applied between the electrodes, electrons are injected from the cathode and holes are injected from the anode. Emission is a phenomenon in which the electrons recombine with the holes in the emitting layer to produce an excited state, and energy is emitted as light when the excited state returns to the ground state.

The performance of an organic EL device has been gradually improved with improvements in emitting materials for an organic EL device. In particular, improvement in color purity (shortening of emission wavelength) of a blue-emitting organic EL device is an important factor leading to high color reproducibility of a display.

As examples of a material for an emitting layer, Patent Documents 1 to 8 disclose diaminopyrene derivatives. Patent Documents 3 to 8 disclose organic EL devices using a diaminopyrene derivative as a doping material. Indeed, by using the materials described in these documents, properties of the organic EL device can be improved. However, it is difficult to obtain pure blue light emission, whereby it is not easy to use those materials as a material for a display. Patent Documents 1 and 2 disclose diaminopyrene derivatives which can emit blue light having a short wave length. However, there is a problem that the luminous lifetime of the organic EL devices obtained by using these materials is very short.

Patent Document 1: Korean Patent Publication No. 10-2007-0115588
Patent Document 2: Korean Patent Publication No. 10-2008-0079956
Patent Document 3: WO2005/108348
Patent Document 4: WO2004/018588
Patent Document 5: WO2004/018587
Patent Document 6: WO2009/102054
Patent Document 7: WO2009/102026
Patent Document 8: WO2009/107596

DISCLOSURE OF THE INVENTION

An object of the invention is to provide a material for an organic EL device which can emit blue light which is high in color purity and has a long luminous lifetime.

According to the invention, the following organic electroluminescent device and the like are provided.

1. An aromatic amine derivative represented by the following formula (1):

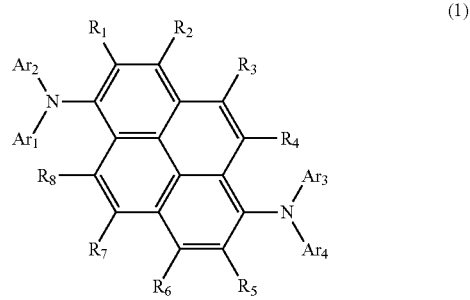

wherein $R_1$ to $R_8$ are independently a hydrogen atom, a halogen atom, a substituted or unsubstituted alkyl group having 1 to 20 carbon atoms, a substituted or unsubstituted cycloalkyl group having 3 to 10 carbon atoms, a substituted or unsubstituted alkylsilyl group having 3 to 30 carbon atoms, a substituted or unsubstituted arylsilyl group having 8 to 30 carbon atoms that form a ring (hereinafter referred to as "ring carbon atoms"), a substituted or unsubstituted alkoxy group having 1 to 20 carbon atoms, a substituted or unsubstituted aralkyl group having 6 to 20 ring carbon atoms, or a substituted or unsubstituted aryl group having 6 to 10 ring carbon atoms, at least one of $R_1$ to $R_8$ is a group other than a hydrogen atom, and $Ar_1$ to $Ar_4$ are a substituted or unsubstituted aryl group having 6 to 30 ring carbon atoms, at least one of $Ar_1$ to $Ar_4$ is an aryl group substituted with one or more substituents selected from a cyano group, a fluorine atom, a halogenated alkyl group, a nitro group and a carbonyl group, provided that, when at least one of $Ar_1$ to $Ar_4$ is a p-fluorophenyl group, at least one of $Ar_1$ to $Ar_4$ which are not a p-fluorophenyl group is an aryl group other than a p-fluorophenyl group which is substituted with one or more substituents selected from a cyano group, a fluorine atom, a halogenated alkyl group, a nitro group and a carbonyl group.

2. The aromatic amine derivative according to 1, which is represented by the following formula (2):

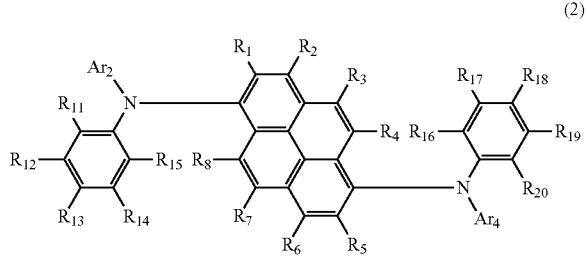

wherein $R_1$ to $R_8$, $Ar_2$ and $Ar_4$ are the same as those in the formula (1), $R_{11}$ to $R_{20}$ are independently a hydrogen atom, a substituted or unsubstituted alkyl group having 1 to 20 carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aralkyl group having 6 to 20 ring carbon atoms, or a substituted or unsubstituted aryl group having 6 to 10 ring carbon atoms, a cyano group, a fluorine atom, a halogenated alkyl group, a nitro group or a carbonyl group, and at least one of $R_{11}$ to $R_{15}$ is a cyano group, a fluorine atom, a halogenated alkyl group, a nitro group or a carbonyl group, and at least one of $R_{16}$ to $R_{20}$ is a cyano group, a fluorine atom, a halogenated alkyl group, a nitro group or a carbonyl group.

3. The aromatic amine derivative according to 2, wherein one of $R_{11}$ to $R_{15}$ is a cyano group, and the remaining $R_{11}$ to $R_{15}$ are hydrogen atoms, and one of $R_{16}$ to $R_{20}$ is a cyano group, and the remaining $R_{16}$ to $R_{20}$ are hydrogen atoms.

4. The aromatic amine derivative according to 3, wherein $R_1$, $R_3$, $R_4$, $R_5$, $R_7$ and $R_8$ are hydrogen atoms.

5. The aromatic amine derivative according to 4, wherein $R_2$ and $R_6$ are independently a substituted or unsubstituted alkyl group having 1 to 20 carbon atoms, a substituted or unsubstituted cycloalkyl group having 3 to 10 carbon atoms or a substituted or unsubstituted silyl group having 3 to 30 carbon atoms.

6. The aromatic amine derivative according to any one of 1 to 5, wherein $Ar_1$ to $Ar_4$ are a substituted or unsubstituted aryl group having 6 to 30 ring carbon atoms, and at least one of $Ar_1$ to $Ar_4$ is an aryl group having one or more cyano groups.

7. An organic luminescent medium comprising the aromatic amine derivative according to any one of 1 to 6.

8. The organic luminescent medium according to 7, which comprises the aromatic amine derivative as a doping material.

9. The organic luminescent medium according to 7 further comprising an anthracene derivative represented by the following formula (10):

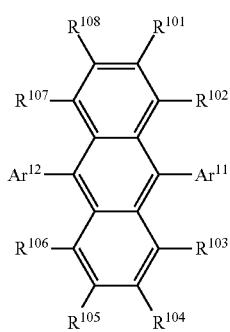

(10)

wherein $Ar^{11}$ and $Ar^{12}$ are independently a substituted or unsubstituted aryl group having 6 to 30 ring carbon atoms or a substituted or unsubstituted heterocyclic group having 5 to 30 atoms that form a ring (hereinafter referred to as "ring atoms"), and $R^{101}$ to $R^{108}$ are independently a hydrogen atom, a fluorine atom, a substituted or unsubstituted alkyl group having 1 to 10 carbon atoms, a substituted or unsubstituted cycloalkyl group having 3 to 10 carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 30 ring carbon atoms, or a substituted or unsubstituted heterocyclic group having 5 to 30 ring atoms.

10. The organic luminescent medium according to 9, wherein in the formula (10), $Ar^{11}$ and $Ar^{12}$ are independently a substituted or unsubstituted fused aromatic ring group having 10 to 30 ring carbon atoms.

11. The organic luminescent medium according to 9, wherein in the formula (10), $Ar^{11}$ is a substituted or unsubstituted phenyl group, and $Ar^{12}$ is a substituted or unsubstituted fused aromatic ring group having 10 to 30 ring carbon atoms.

12. The organic luminescent medium according to 11, wherein the anthracene derivative is represented by the following formula (10-4);

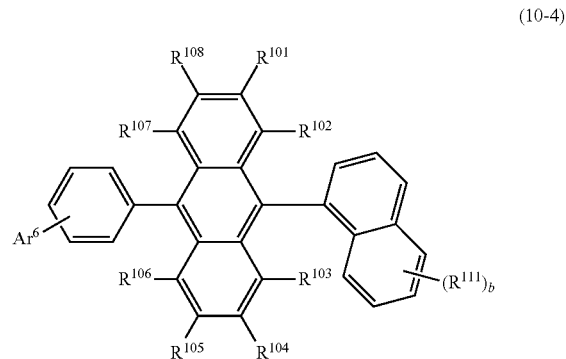

(10-4)

wherein $R^{101}$ to $R^{108}$ are the same as those in formula (10), $R^{111}$ is a substituted or unsubstituted aryl group having 6 to 30 ring carbon atoms, a substituted or unsubstituted heterocyclic group having 5 to 30 ring atoms, a substituted or unsubstituted alkyl group having 1 to 10 carbon atoms, a substituted or unsubstituted cycloalkyl group having 3 to 10 ring carbon atoms, a substituted or unsubstituted alkoxy group having 1 to 20 carbon atoms, a substituted or unsubstituted silyl group, a cyano group or a fluorine atom, b is an integer of 0 to 7, and plural $R^{111}$s may be the same or different when b is an integer of 2 or more, and $Ar^6$ is a substituted or unsubstituted aryl group having 6 to 30 ring carbon atoms, a substituted or unsubstituted alkyl group having 1 to 10 carbon atoms, a substituted or unsubstituted cycloalkyl group having 3 to 10 ring carbon atoms or a substituted or unsubstituted heterocyclic group having 5 to 30 ring atoms, or $Ar^6$ may form a ring with the benzene ring to which $Ar^6$ bonds.

13. The organic luminescent medium according to 11, wherein the anthracene derivative is represented by the following formula (10-5):

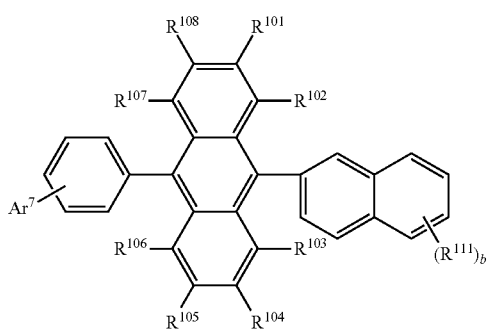

(10-5)

wherein $R^{101}$ to $R^{108}$ are the same as those in formula (10), $R^{111}$ is a substituted or unsubstituted aryl group having 6 to 30 ring carbon atoms, a substituted or unsubstituted heterocyclic group having 5 to 30 ring atoms, a substituted or unsubstituted alkyl group having 1 to 10 carbon atoms, a substituted or unsubstituted cycloalkyl group having 3 to 10 ring carbon atoms, a substituted or unsubstituted alkoxy group having 1 to 20 carbon atoms, a substituted or unsubstituted silyl group, a cyano group or a fluorine atom, b is an integer of 0 to 7, and plural $R^{111}$s may be the same or different when b is an integer of 2 or more, and $Ar^7$ is a substituted or unsubstituted aryl group having 6 to 30 ring carbon atoms, a substituted or unsubstituted alkyl group having 1, to 10 carbon atoms, a substituted or unsubstituted cycloalkyl group having 3 to 10 ring carbon atoms or a substituted or unsubstituted heterocyclic group having 5 to 30 ring atoms, or $Ar^7$ may form a ring with the benzene ring to which $Ar^7$ bonds.

14. The organic luminescent medium according to 9, wherein the anthracene derivative is represented by the following formula (10-6):

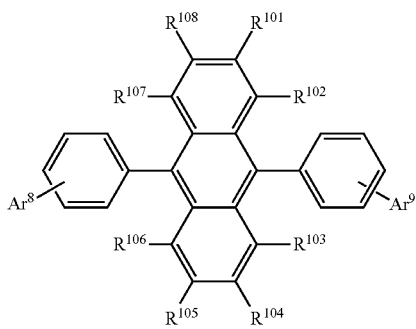

(10-6)

wherein $R^{101}$ to $R^{108}$ are the same as those in the formula (10), $Ar^8$ is a substituted or unsubstituted aryl group having 6 to 30 ring carbon atoms, a substituted or unsubstituted alkyl group having 1 to 10 carbon atoms, a substituted or unsubstituted cycloalkyl group having 3 to 10 ring carbon atoms, or a substituted or unsubstituted heterocyclic group having 5 to 50 ring atoms, or $Ar^8$ may form a ring with the benzene ring to which $Ar^8$ bonds, and $Ar^9$ is a substituted or unsubstituted aryl group having 6 to 30 ring carbon atoms, a substituted or unsubstituted alkyl group having 1 to 10 carbon atoms, a substituted or unsubstituted cycloalkyl group having 3 to 10 ring carbon atoms, or a substituted or unsubstituted heterocyclic group having 5 to 50 ring atoms.

15. The organic luminescent medium according to 9, wherein the anthracene derivative is represented by the following formula (10-7):

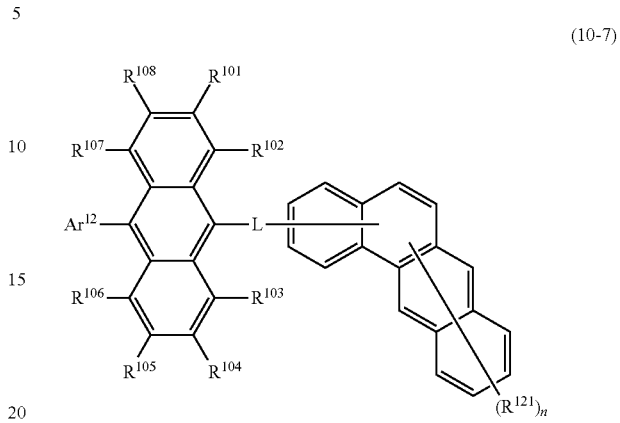

(10-7)

wherein $R^{101}$ to $R^{108}$ and $Ar^{12}$ are the same as those in the formula (10), L is a single bond, a substituted or unsubstituted arylene group having 6 to 30 ring carbon atoms or a substituted or unsubstituted divalent heterocyclic group having 5 to 30 ring atoms, $R^{121}$ is a substituted or unsubstituted aryl group having 6 to 30 ring carbon atoms, a substituted or unsubstituted heterocyclic group having 5 to 30 ring atoms, a substituted or unsubstituted alkyl group having 1 to 10 carbon atoms, a substituted or unsubstituted cycloalkyl group having 3 to 10 ring carbon atoms, a substituted or unsubstituted alkoxy group having 1 to 20 carbon atoms, a substituted or unsubstituted silyl group, a cyano group or a fluorine atom, and n is an integer of 0 to 11, and plural $R^{121}$s may be the same or different when n is an integer of 2 or more.

16. The organic luminescent medium according to 9, wherein the anthracene derivative is represented by the following formula (10-8):

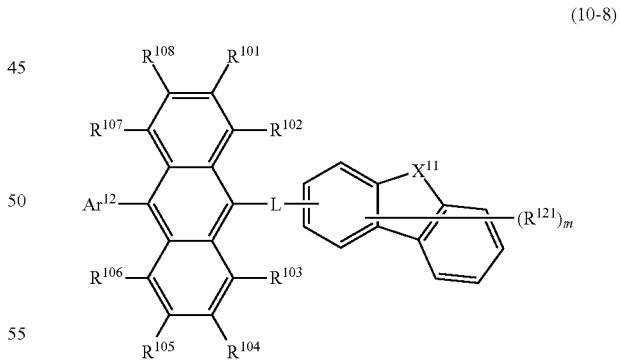

(10-8)

wherein $R^{101}$ to $R^{108}$ and $Ar^{12}$ are the same as those in the formula (10), L is a single bond, a substituted or unsubstituted arylene group having 6 to 50 ring carbon atoms or a substituted or unsubstituted divalent heterocyclic group having 5 to 50 ring atoms, $X^{11}$ is an oxygen atom, a sulfur atom, or —NR— wherein R is the same as in $R^{101}$ to $R^{108}$, $R^{121}$ is a substituted or unsubstituted aryl group having 6 to 30 ring carbon atoms, a substituted or unsubstituted heterocyclic group having 5 to 30 ring atoms, a substituted or unsubstituted alkyl group having 1 to 10 carbon atoms, a substituted or unsubstituted cycloalkyl group having 3 to 10 ring carbon atoms, a substituted or unsubstituted alkoxy group having 1 to 20 carbon atoms, a substituted or unsubstituted silyl group, a cyano group or a fluorine atom, and m is an integer of 0 to 7, and plural $R^{121}$s may be the same or different when m is an integer of 2 or more.

17. The organic luminescent medium according to 9, wherein the anthracene derivative is represented by the following formula (10-9):

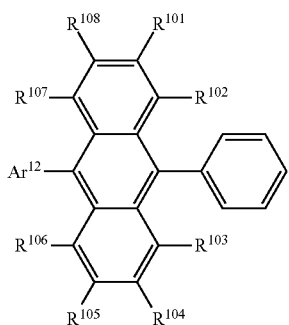

(10-9)

wherein $R^{101}$ to $R^{108}$ and $Ar^{12}$ are the same as those in the formula (10).

18. The organic luminescent medium according to 9, wherein the anthracene derivative is represented by the following formula (10-10):

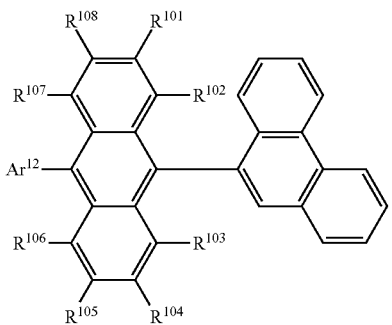

(10-10)

wherein $R^{101}$ to $R^{108}$ and $Ar^{12}$ are the same as those in the formula (10).

19. The organic luminescent medium according to 9, wherein in the formula (10), $Ar^{11}$ and $Ar^{12}$ are independently a group formed by 1 to 4 hydrocarbon aromatic rings which may be substituted, and $R^{101}$ to $R^{108}$ are independently a hydrogen atom, an alkyl group having 1 to 4 carbon atoms, a silyl group or a silyl group substituted with an alkyl group having 1 to 4 carbon atoms.

20. An organic electroluminescence device comprising a cathode, an anode, and one or more organic thin film layers comprising an emitting layer therebetween, wherein at least one layer of the organic thin film layers comprises the aromatic amine derivative according to any one of 1 to 6 singly or as a component of a mixture.

21. The organic electroluminescence device according to 20, wherein the emitting layer comprises the aromatic amine derivative.

According to the invention, an organic EL device which can emit blue light which is high in color purity and has a long luminous lifetime can be provided.

BEST MODE FOR CARRYING OUT THE INVENTION

The aromatic amine derivative of the invention is represented by the following formula (1):

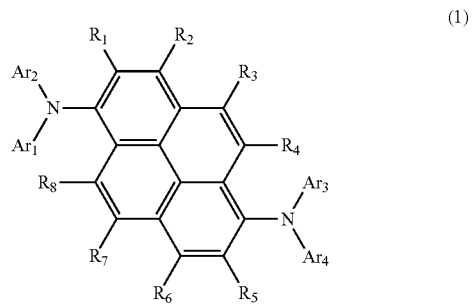

(1)

In the formula (1), $R_1$ to $R_8$ are independently a hydrogen atom, a halogen atom, a substituted or unsubstituted alkyl group having 1 to 20 carbon atoms, a substituted or unsubstituted cycloalkyl group having 3 to 10 carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aralkyl group having 6 to 20 ring carbon atoms, or a substituted or unsubstituted aryl group having 6 to 10 ring carbon atoms, at least one of $R_1$ to $R_5$ is a group (including a halogen atom) other than a hydrogen atom, and $Ar_1$ to $Ar_4$ are a substituted or unsubstituted aryl group having 6 to 30 ring carbon atoms, at least one of $Ar_1$ to $Ar_4$ is an aryl group having one or more groups or atoms selected from a cyano group, a fluorine atom, a halogenated alkyl group, a nitro group and a carbonyl group, provided that, when at least one of $Ar_1$ to $Ar_4$ is a p-fluorophenyl group, at least one of $Ar_1$ to $Ar_4$ which is not a p-fluorophenyl group is an aryl group other than a p-fluorophenyl group which is substituted with one or more substituents selected from a cyano group, a fluorine atom, a halogenated alkyl group, a nitro group and a carbonyl group.

The p-fluorophenyl group is a group in which a phenyl group is substituted by a fluorine atom at the para position, and is not substituted by other substituents than this fluorine atom.

The aromatic amine derivative of the invention can have improved luminous lifetime by allowing a predetermined substituent to be bonded to the pyrene ring. Further, since the aryl group of the diarylamino group has a cyano group, a fluorine atom, a halogenated alkyl group, a nitro group or a carbonyl group, which are electron-attracting groups, blue emission which has a shorter emission wavelength as compared with conventional organic EL devices can be obtained. Hereinafter, a cyano group, a fluorine atom, a halogenated alkyl group, a nitro group or a carbonyl group may often be referred to as the "electron-attracting group".

The electron-attracting group is a group having a function of decreasing the electron density. Due to the presence of these electron-attracting groups, excessive electrons are trapped and electrons are prevented electrons from entering a hole-transporting material. As a result, deterioration of a hole-transporting material can be prevented, whereby an organic EL device has a prolonged lifetime.

Preferable electron-attracting groups include a cyano group, a fluorine atom and a halogenated alkyl group, with a cyano group being particularly preferable.

Of the above-mentioned electron-attracting groups, it is considered that the fluorine atom has an effect of allowing an organic EL device to emit light with a shorter wavelength due to the electronegativity thereof. It is assumed that a shorter distance from the fluorine atom to N (i.e. distance to the main skeleton which affects the wavelength) can further improve color purity.

Therefore, in respect of high color purity, in the formula (1), if at least one of $Ar_1$ to $Ar_4$ is a p-fluorophenyl group, at least one of remaining $Ar_1$ to $Ar_4$ is an aryl group which is substituted by one or more groups or atoms other than the p-fluorophenyl group, i.e. one or more groups or atoms selected from a cyano group, a fluorine atom, a halogenated alkyl group, a nitro group and a carbonyl group.

The aromatic amine derivative of the invention is preferably represented by the following formula (2).

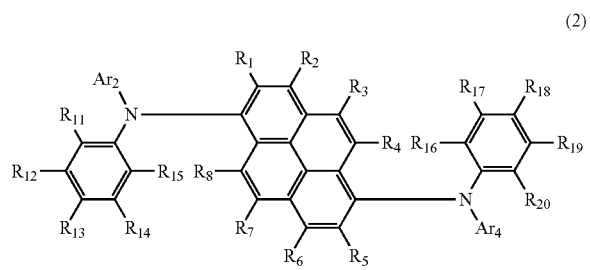

(2)

In the formula (2), $R_1$ to $R_8$ and $Ar_2$ and $Ar_4$ are the same as those in the formula (1).

$R_{11}$ to $R_{20}$ are independently a hydrogen atom, a substituted or unsubstituted alkyl group having 1 to 20 carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aralkyl group having 6 to 20 ring carbon atoms, a substituted or unsubstituted aryl group having 6 to 10 ring carbon atoms, a substituted or unsubstituted heterocyclic group having 5 to 20 ring atoms, a cyano group, a fluorine atoms, a halogenated alkyl group, a nitro group or a carbonyl group.

At least one of $R_{11}$ to $R_{15}$ is a cyano group, a fluorine atom, a halogenated alkyl group, a nitro group or a carbonyl group and at least one of $R_{16}$ to $R_{20}$ is a cyano group, a fluorine atom, a halogenated alkyl group, a nitro group or a carbonyl group.

In respect of high color purity, in the formula (2), if $R_{13}$ or $R_{18}$ is an electron-attracting group, it is preferred that $R_{13}$ or $R_{18}$ be one of a cyano group, a halogenated alkyl group, a nitro group or a carbonyl group. Further, it is preferred that $R_{13}$ and $R_{18}$ be one of a cyano group, a halogenated alkyl group, a nitro group or a carbonyl group, and that the remaining are hydrogen atoms.

In the formula (2), it is preferred that one of $R_{11}$ to $R_{15}$ be a cyano group and the remaining be hydrogen atoms, and one of $R_{16}$ to $R_{20}$ be a cyano group and the remaining be hydrogen atoms.

The aromatic amine derivative of the invention is preferably presented by the following formula (3) or (4).

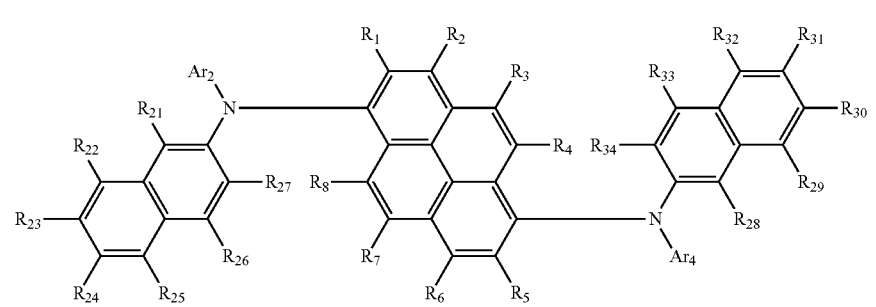

(3)

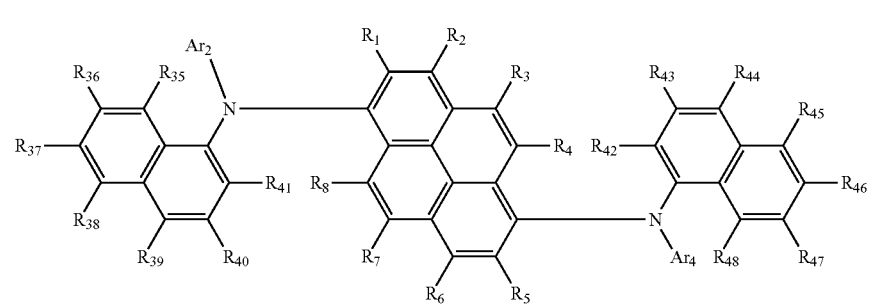

(4)

In the formula (3) or (4), $R_1$ to $R_8$ and $Ar_2$ and $Ar_4$ are the same as those in the formula (1).

$R_{21}$ to $R_{48}$ are independently a hydrogen atom, a substituted or unsubstituted alkyl group having 1 to 20 carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aralkyl group having 6 to 20 ring carbon atoms, a substituted or unsubstituted aryl group having 6 to 10 ring carbon atoms, a substituted or unsubstituted heterocyclic group having 5 to 20 ring atoms, a cyano group, a fluorine atom, a halogenated alkyl group, a nitro group or a carbonyl group.

It is preferred that at least one of $R_{21}$ to $R_{27}$ be a cyano group, a fluorine atom, a halogenated alkyl group, a nitro group or a carbonyl group and that at least one of $R_{28}$ to $R_{34}$ be a cyano group, a fluorine atom, a halogenated alkyl group, a nitro group or a carbonyl group.

In respect of high color purity, if at least one of $R_{22}$ to $R_{25}$ and/or at least one of $R_{29}$ to $R_{32}$ is an electron-attracting group, it is preferred that at least one of $R_{22}$ to $R_{25}$ and/or at least one of $R_{29}$ to $R_{32}$ be a cyano group, a halogenated alkyl group, a nitro group or a carbonyl group.

It is preferred that the remaining be hydrogen atoms.

Further, it is preferred that $Ar_2$ or $Ar_4$ be an aryl group which is other than a p-fluorophenyl group and is substituted by one or more selected from a cyano group, a fluorine atom, a halogenated alkyl group, a nitro group and a carbonyl group, and that $R_{21}$ to $R_{34}$ be hydrogen atoms.

It is preferred that at least one of $R_{35}$ to $R_{41}$ be a cyano group, a fluorine atom, a halogenated alkyl group, a nitro group or a carbonyl group and at least one of $R_{42}$ to $R_{48}$ be a cyano group, a fluorine atom, a halogenated alkyl group, a nitro group or a carbonyl group.

In respect of high color purity, if at least one of $R_{35}$ to $R_{38}$ and/or at least one of $R_{45}$ to $R_{48}$ is an electron-attracting group, it is preferred that at least one of $R_{35}$ to $R_{38}$ and/or at least one of $R_{45}$ to $R_{48}$ be a cyano group, a halogenated alkyl group, a nitro group or a carbonyl group.

It is preferred that the remaining be hydrogen atoms.

Further, it is preferred that $Ar_2$ or $Ar_4$ be an aryl group which is other than a p-fluorophenyl group and is substituted by one or more selected from a cyano group, a fluorine atom, a halogenated alkyl group, a nitro group and a carbonyl group, and that $R_{35}$ to $R_{48}$ be hydrogen atoms.

In addition, it is preferred that $R_1$, $R_3$, $R_4$, $R_5$, $R_7$ and $R_8$ be hydrogen atoms. Since $R_2$ and $R_6$ are the active sites of the pyrene ring, the active sites can be protected by introducing a substituent to $R_2$ and $R_6$. As a result, the stability of the compound is improved.

It is particularly preferred that $R_2$ and $R_6$ be independently a substituted or unsubstituted alkyl group having 1 to 20 carbon atoms, a substituted or unsubstituted cycloalkyl group having 3 to 10 carbon atoms or a substituted or unsubstituted silyl group having 3 to 30 carbon atoms. If $R_2$ and $R_6$ are these groups, the luminous life is particularly improved.

In this specification, the "ring carbon" means a carbon atom which constitutes a saturated ring, an unsaturated ring or an aromatic ring. The "ring atom" means a carbon atom or a hetero atom which constitutes a hetero ring (including a saturated ring, an unsaturated ring and an aromatic ring).

Examples of substituents in "substituted or unsubstituted . . . " include an alkyl group, alkylsilyl group, halogenated alkyl group, aryl group, cycloalkyl group, alkoxy group, heterocyclic group, aralkyl group, aryloxy group, arylthio group, alkoxycarbonyl group, halogen atom, hydroxyl group, nitro group, cyano group, carboxy group, dibenzofuranyl group and fluorenyl group as described below.

The hydrogen atom of the invention includes light hydrogen and deuterium.

Specific examples of the groups in formulas (1) and (2), and the substituents are shown below.

Examples of the alkyl group include a methyl group, ethyl group, propyl group, isopropyl group, n-butyl group, s-butyl group, isobutyl group, t-butyl group, n-pentyl group, n-hexyl group, n-heptyl group and n-octyl group.

The alkyl group preferably has 1 to 10 carbon atoms, and more preferably 1 to 6 carbon atoms. Of these, a methyl group, ethyl group, propyl group, isopropyl group, n-butyl group, s-butyl group, isobutyl group, t-butyl group, n-pentyl group and n-hexyl group are preferable.

The alkylsilyl group is represented by $-SiY_3$, and examples of Y are the same as those of the alkyl group.

As the aryl group, a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 6-chrysenyl group, 1-benzo[c]phenanthryl group, 2-benzo[c]phenanthryl group, 3-benzo[c]phenanthryl group, 4-benzo[c]phenanthryl group, 5-benzo[c]phenanthryl group, 6-benzo[c]phenanthryl group, 1-benzo[g]chrysenyl group, 2-benzo[g]chrysenyl group, 3-benzo[g]chrysenyl group, 4-benzo[g]chrysenyl group, 5-benzo[g]chrysenyl group, 6-benzo[g]chrysenyl group, 7-benzo[g]chrysenyl group, 8-benzo[g]chrysenyl group, 9-benzo[g]chrysenyl group, 10-benzo[g]chrysenyl group, 11-benzo[g]chrysenyl group, 12-benzo[g]chrysenyl group, 13-benzo[g]chrysenyl group, 14-benzo[g]chrysenyl group, 1-triphenylenyl group, 2-triphenylenyl group, 2-fluorenyl group, benzofluorenyl group, dibenzofluorenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group or the like can be given.

The aryl group has preferably 6 to 20, further preferably 6 to 10 ring carbon atoms. Preferable aryl groups are a phenyl group and a naphthyl group.

The arylsilyl group is represented by $-SiZ_3$, and examples of Z are the same as those of the aryl group.

The alkoxy group is represented by $-OY$, and examples of Y are the same as those of the alkyl or aryl group.

The aralkyl group is represented by $-Y-Z$, and examples of Y include alkylene groups corresponding to the examples of the alkyl group, and examples of Z are the same as those of the aryl group.

Examples of the cycloalkyl group include a cyclopropyl group, cyclobutyl group, cyclopentyl group, cyclohexyl group, 4-methylcyclohexyl group, 1-adamantyl group, 2-adamantyl group, 1-norbornyl group and 2-norbornyl group. The cycloalkyl group has preferably 3 to 10 ring carbon atoms, and further preferably 5 to 8 ring carbon atoms.

Specific examples of the aromatic amine derivatives are given below.

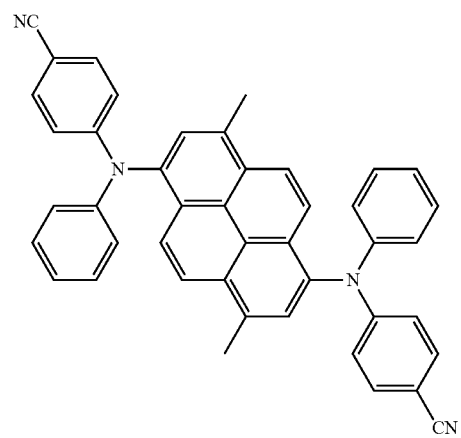
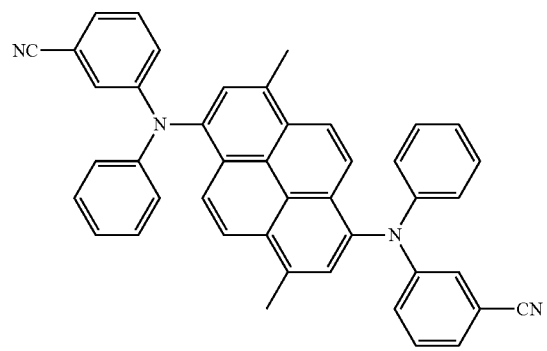
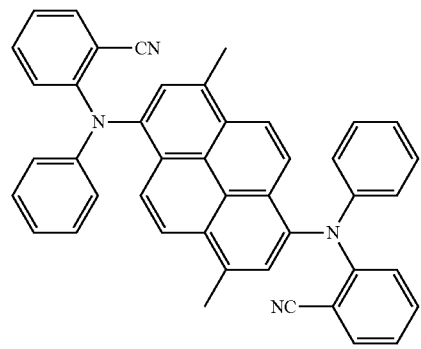
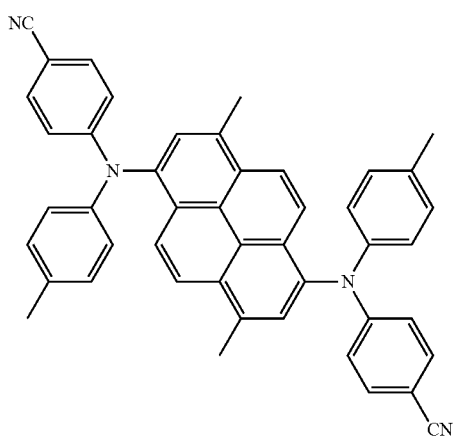
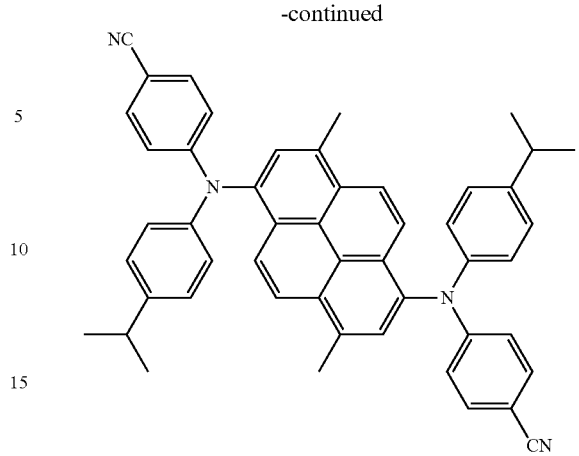
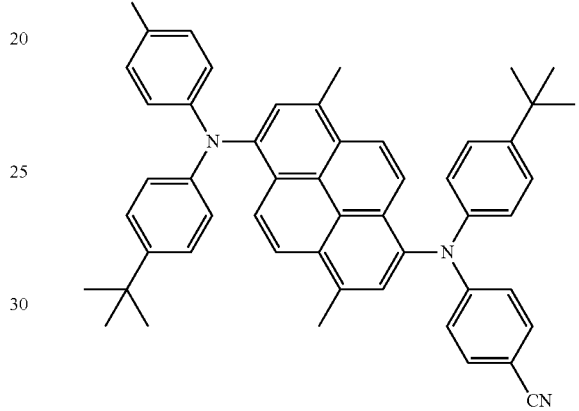
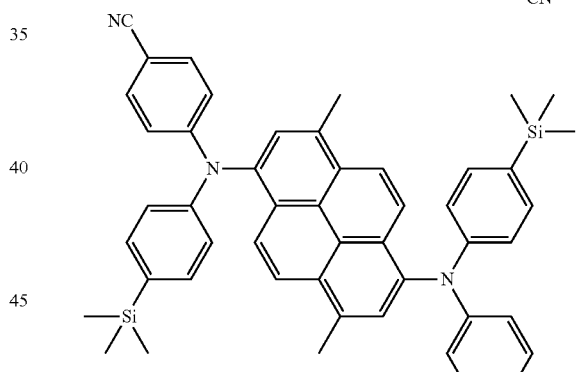
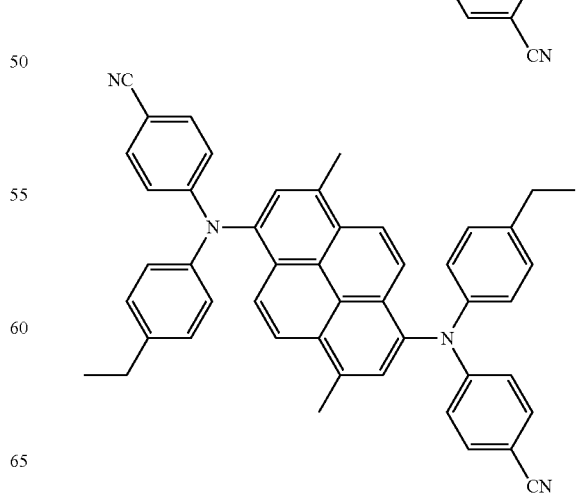

-continued
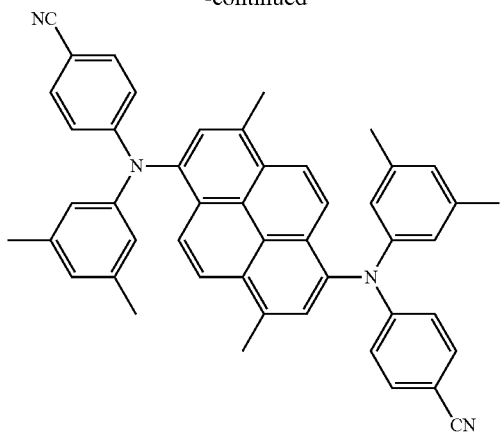
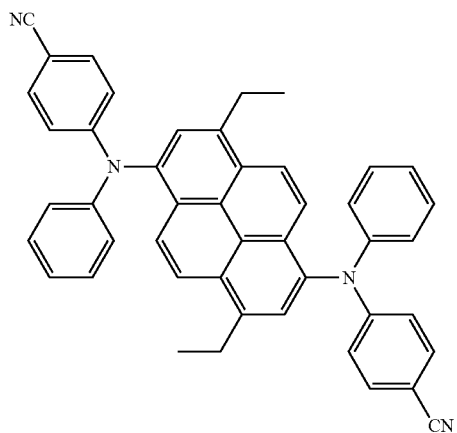
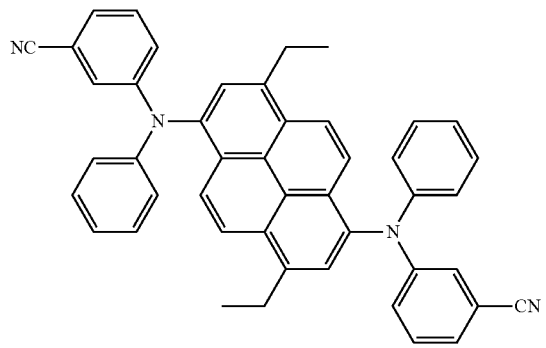
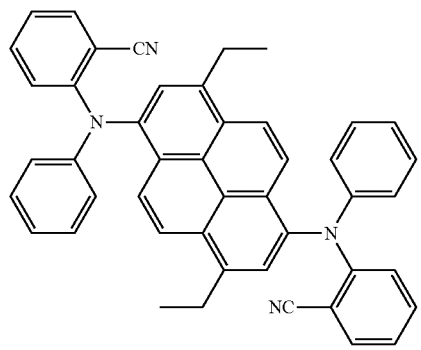
-continued
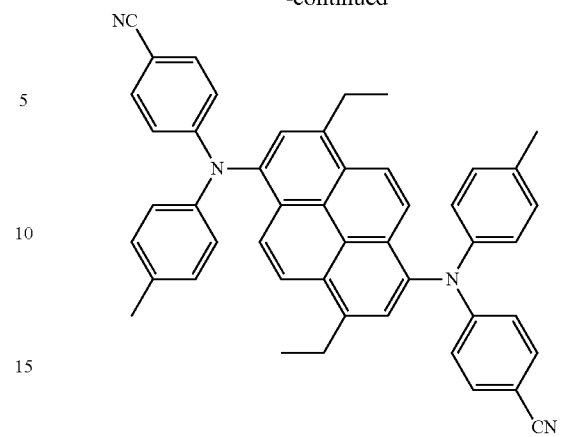
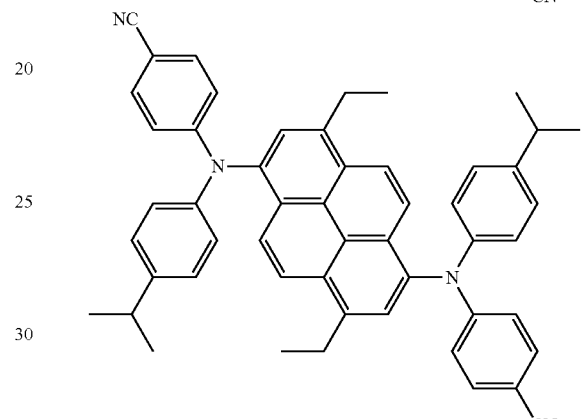
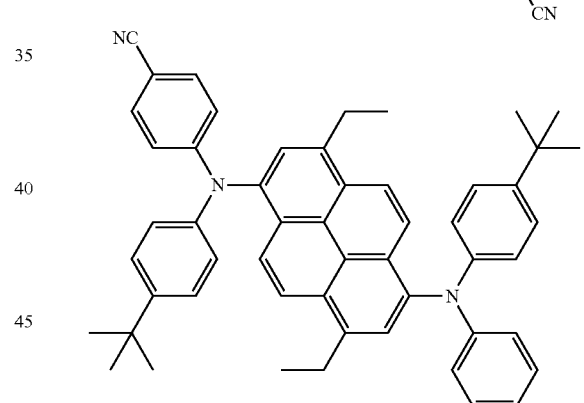
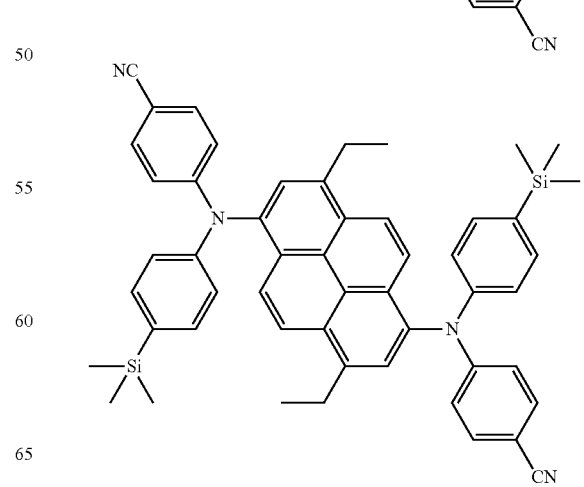

-continued
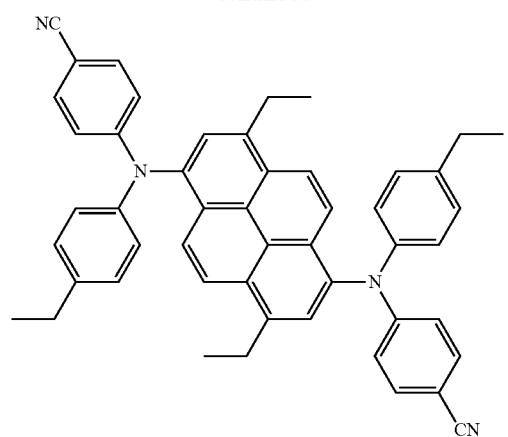
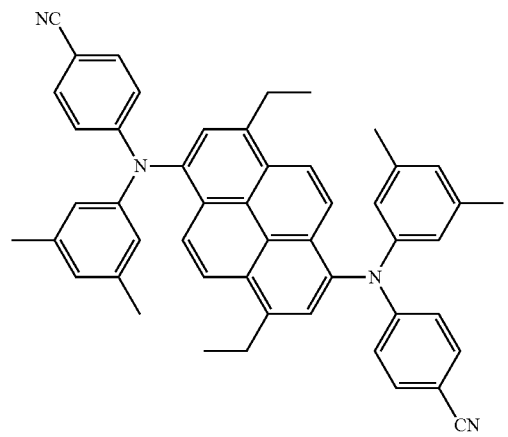
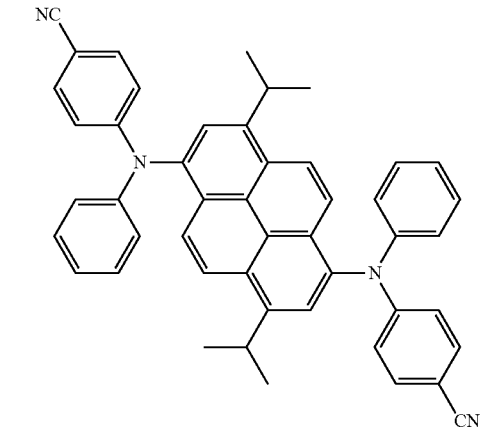
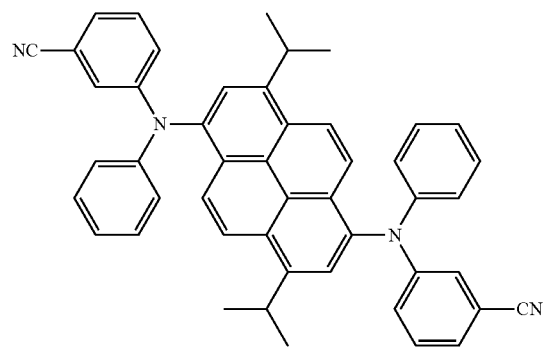
-continued
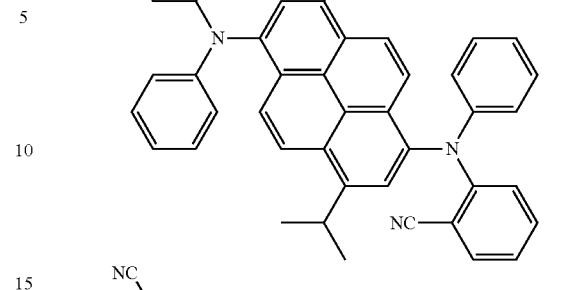
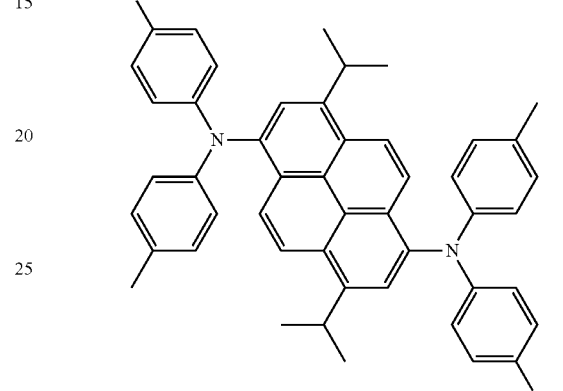
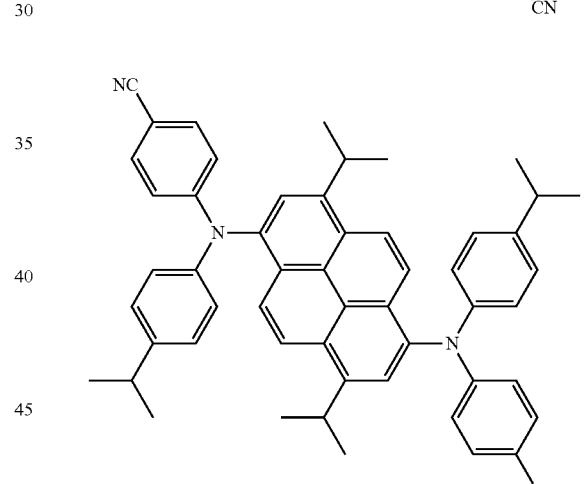
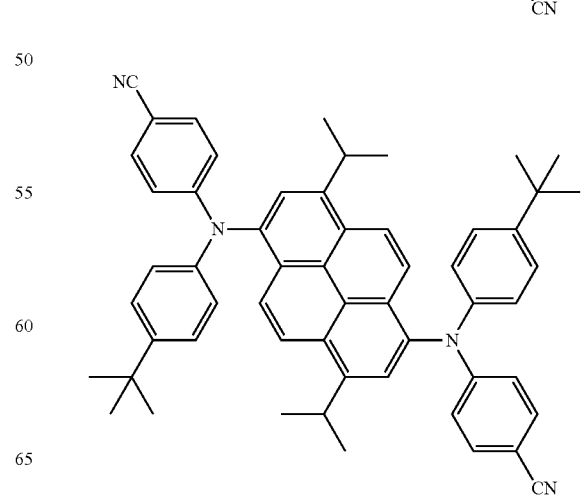

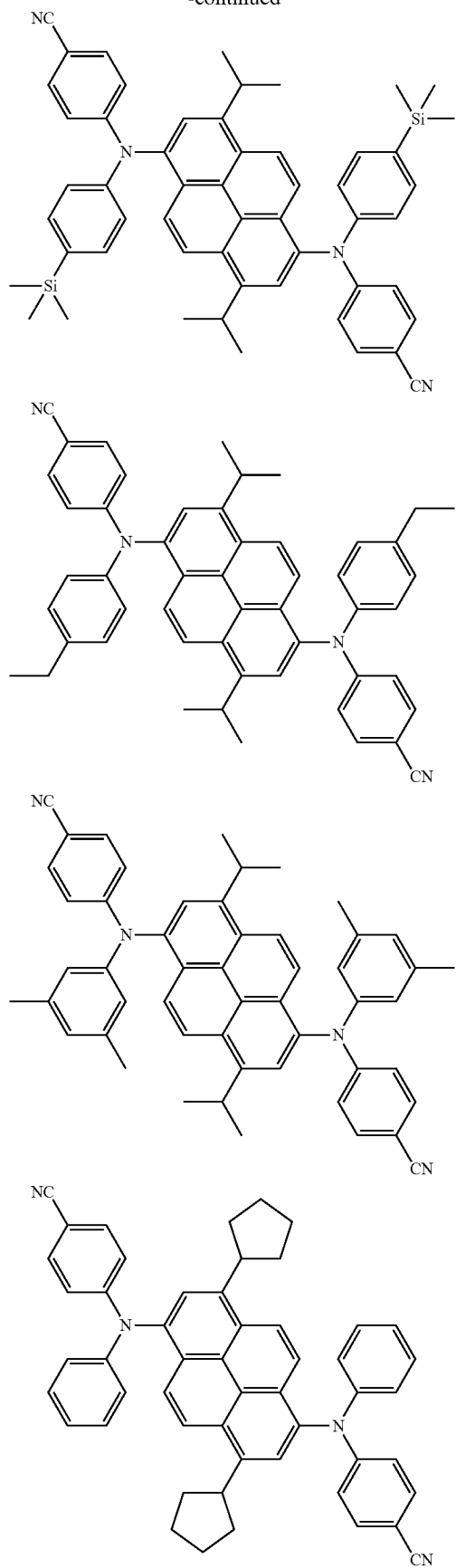
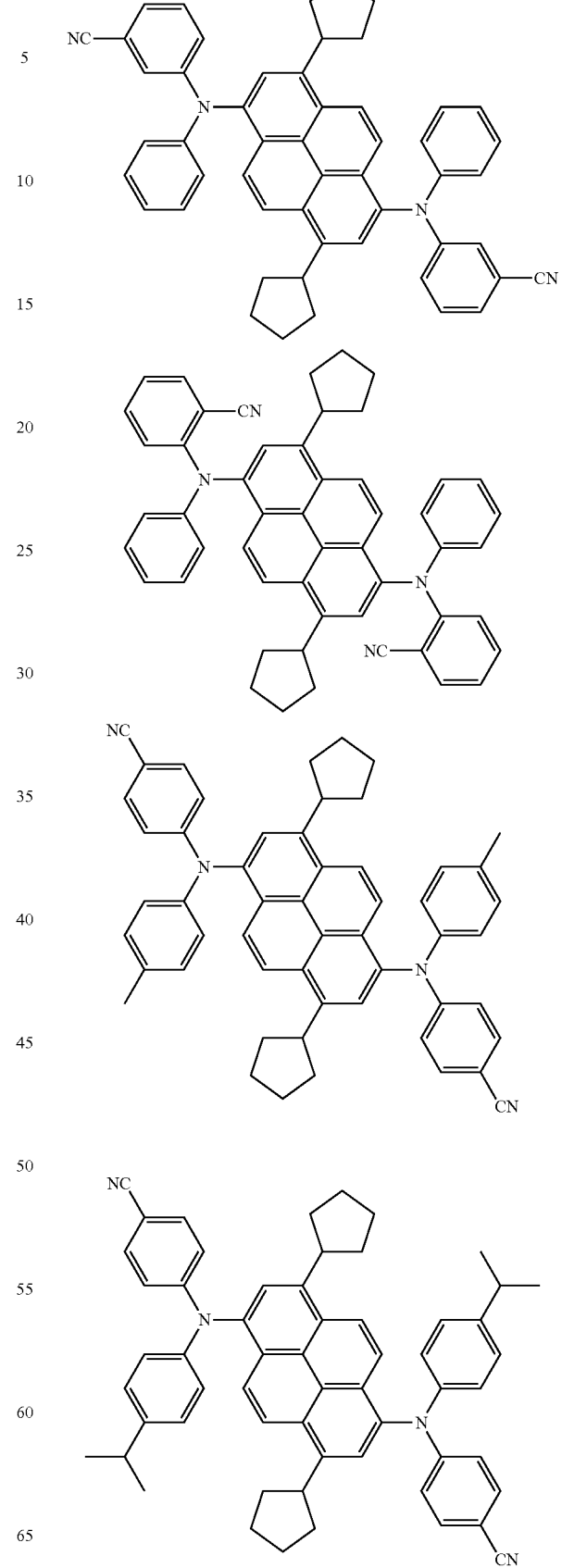

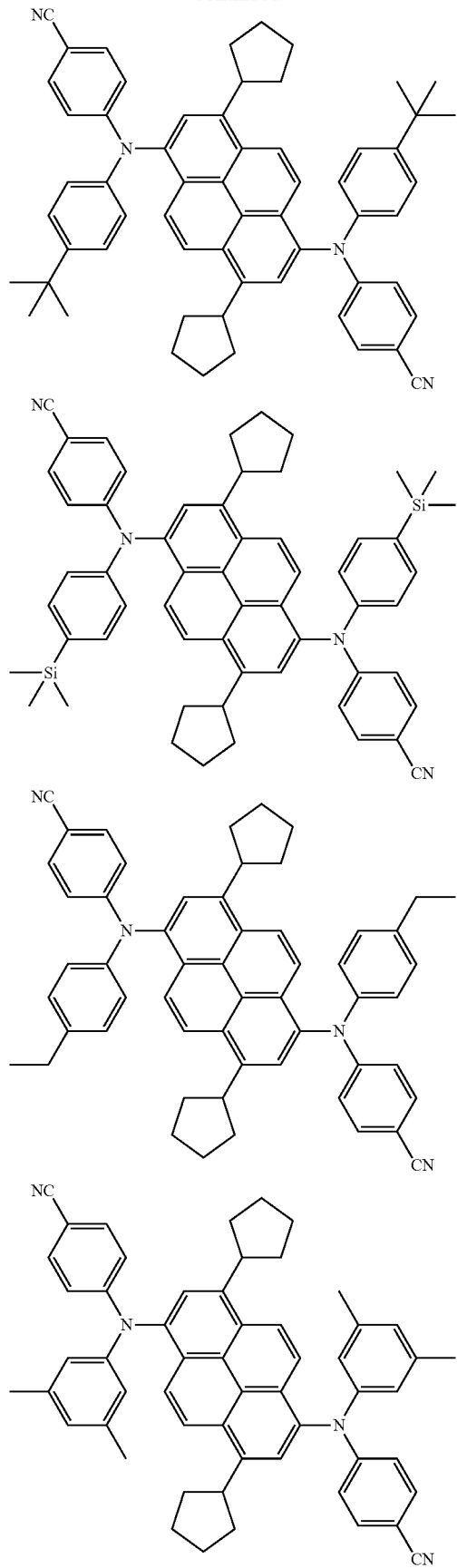
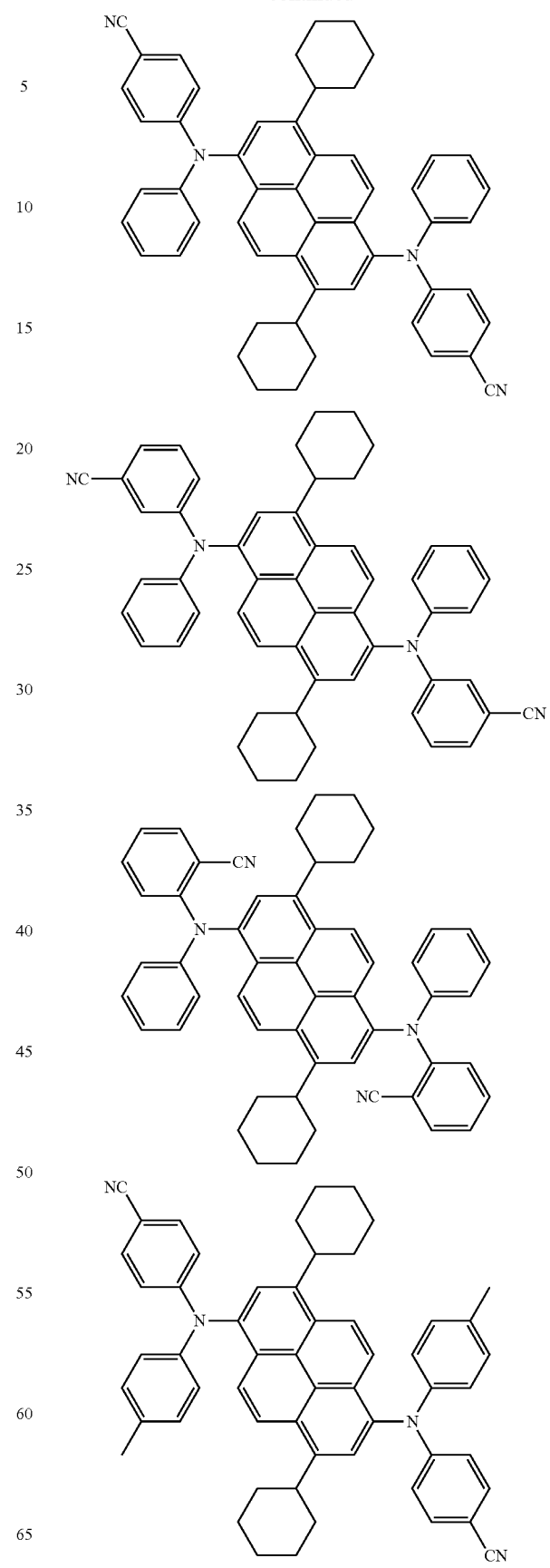

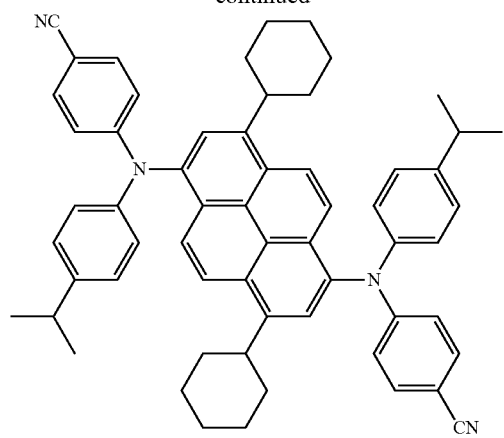
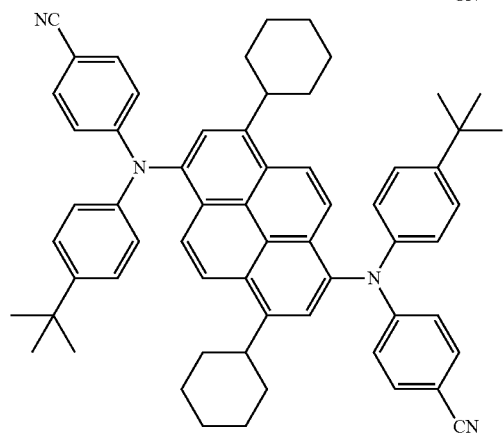
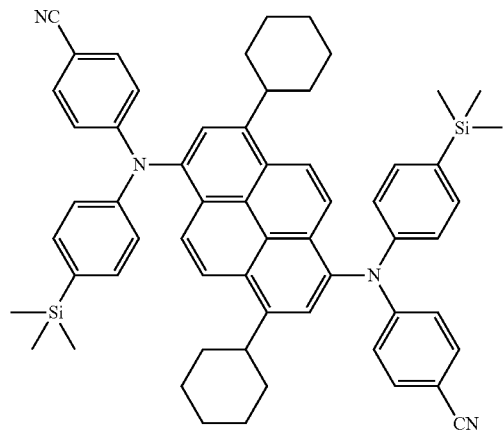
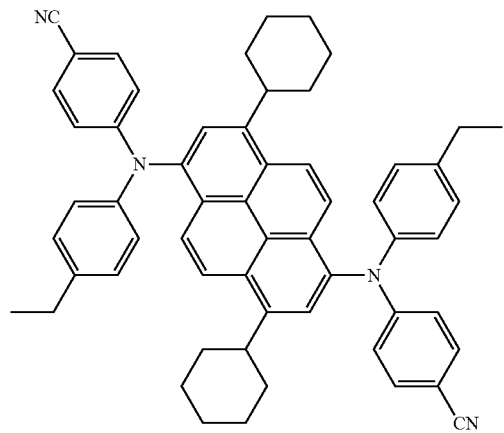
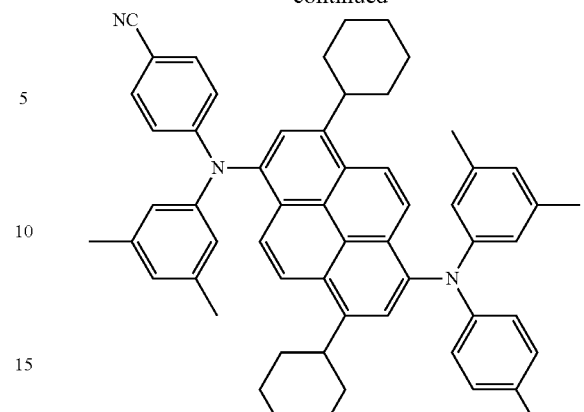
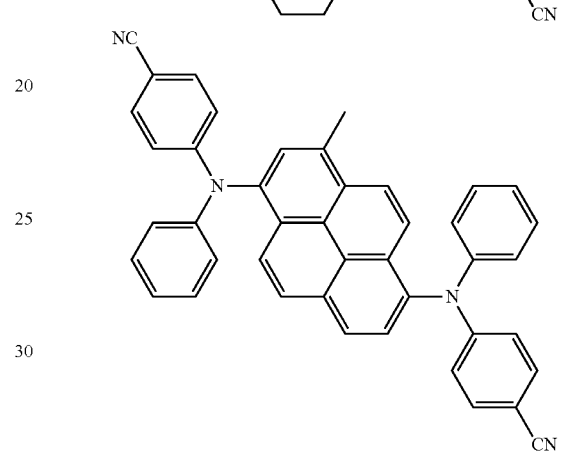
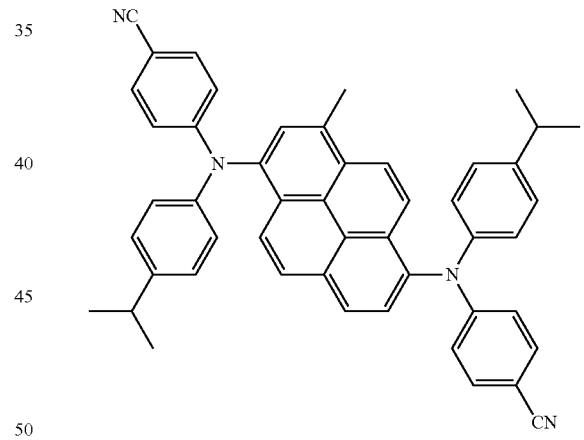
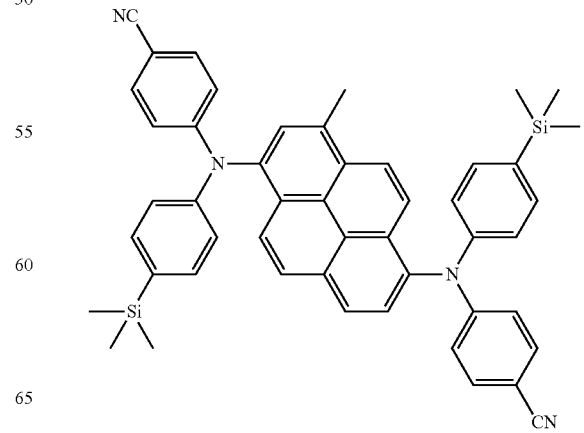

25
-continued
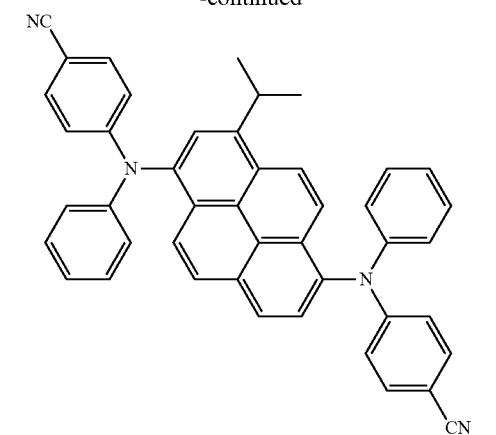
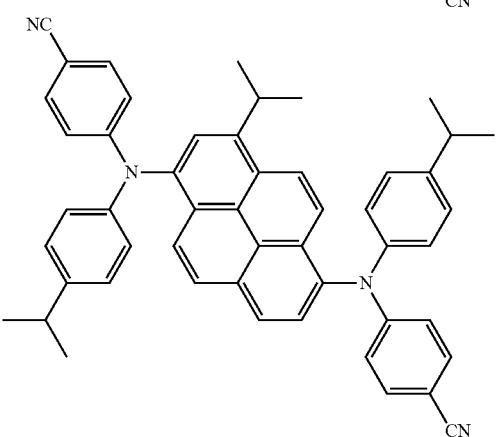
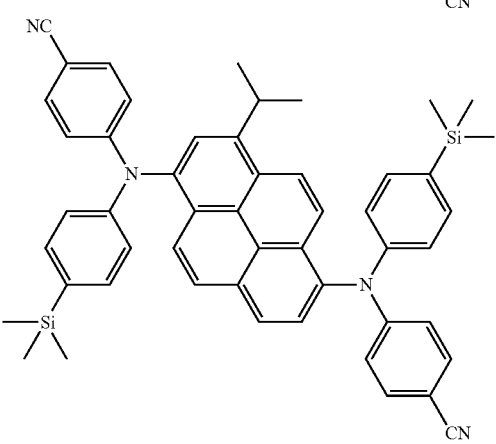
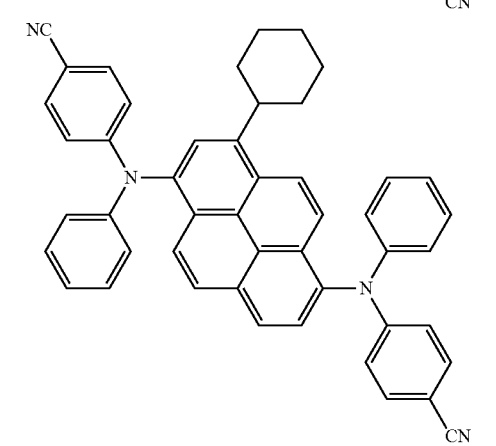
26
-continued
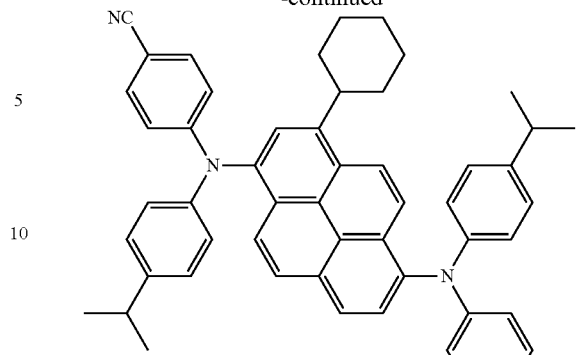
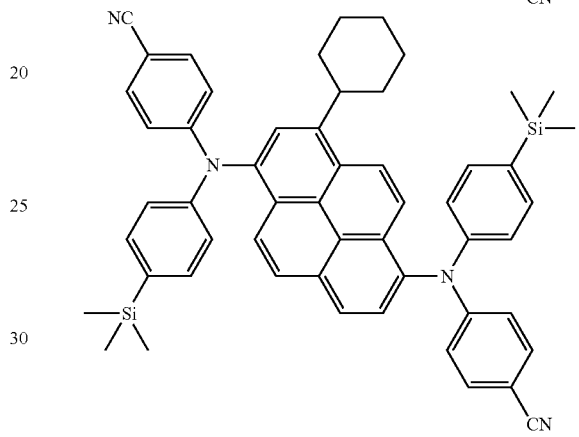
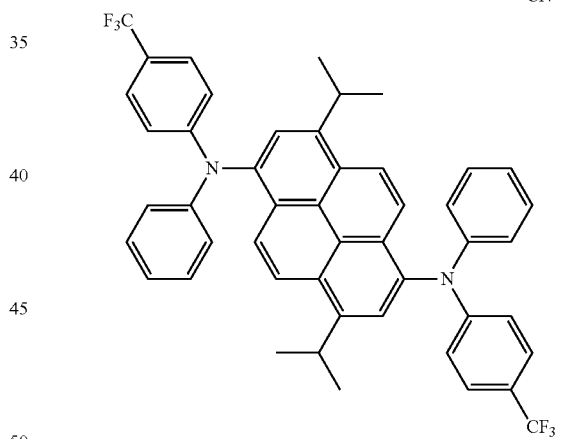
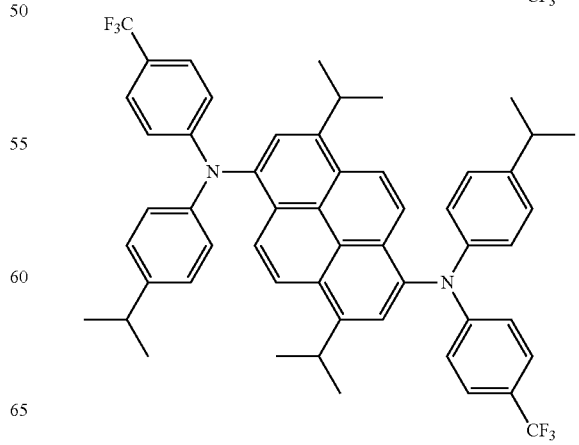

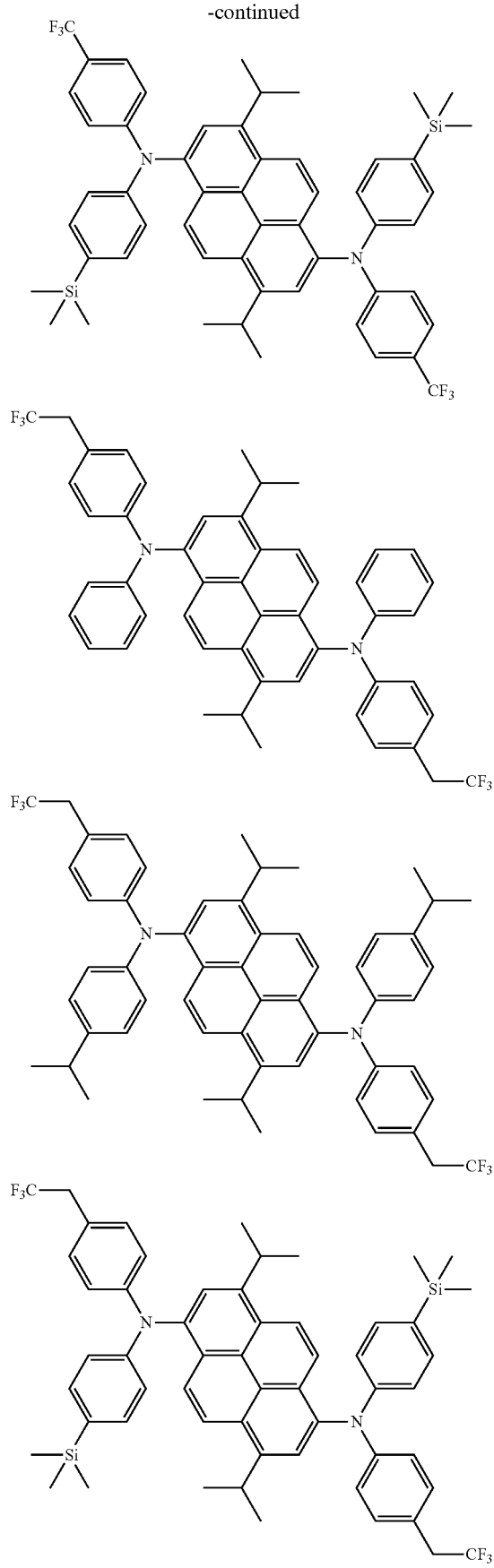
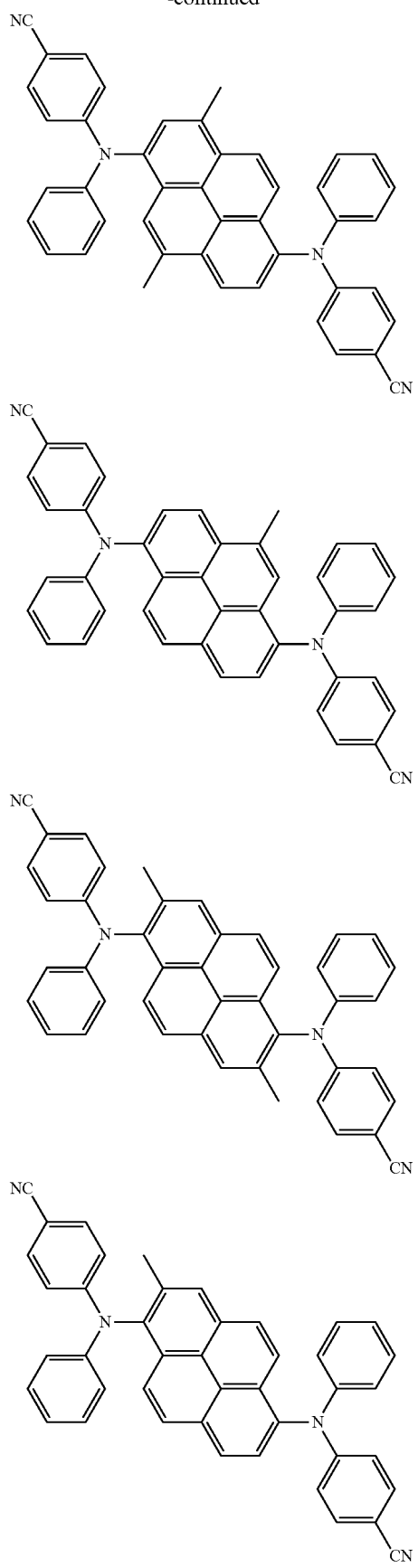

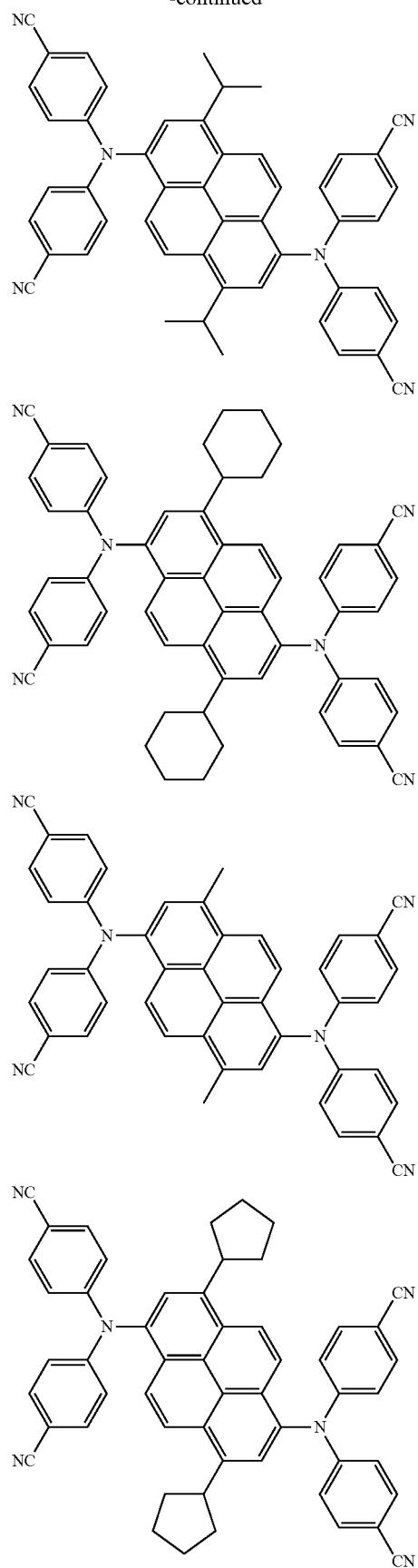
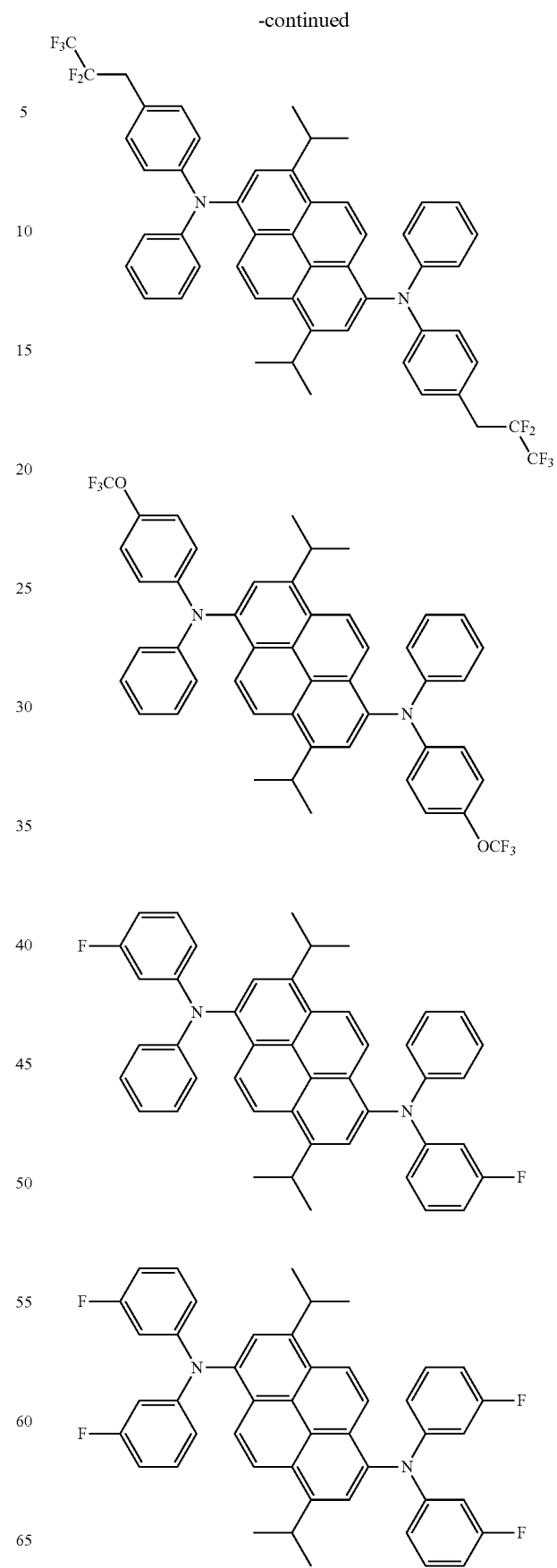

31
-continued
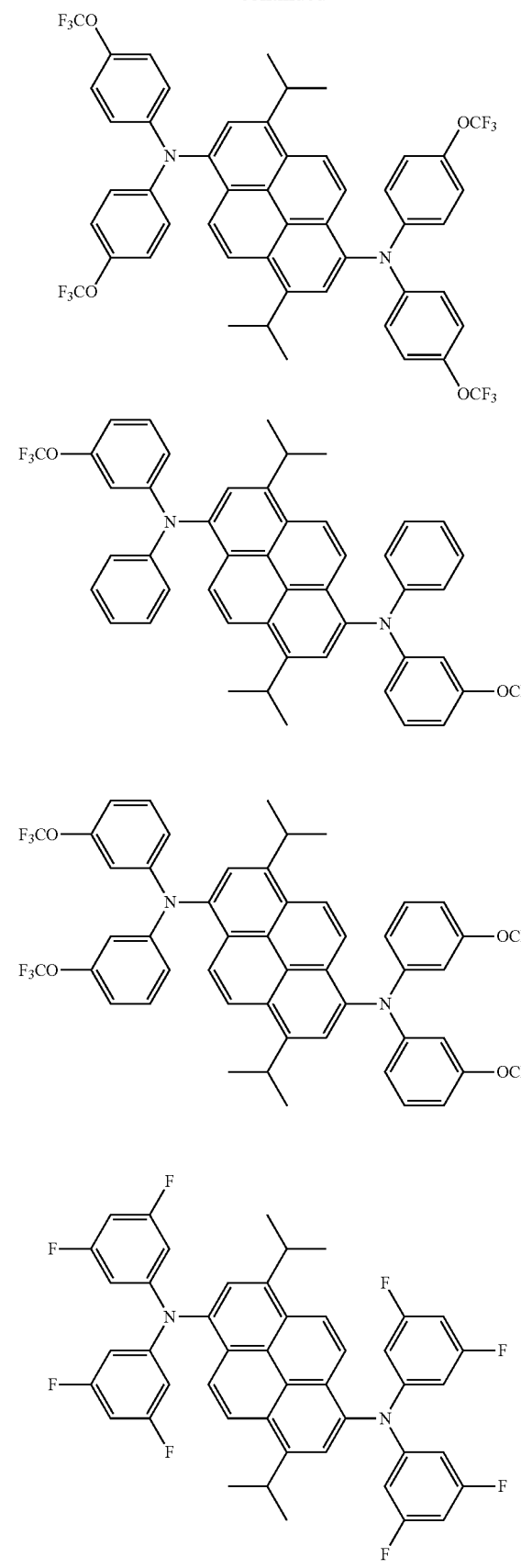
32
-continued
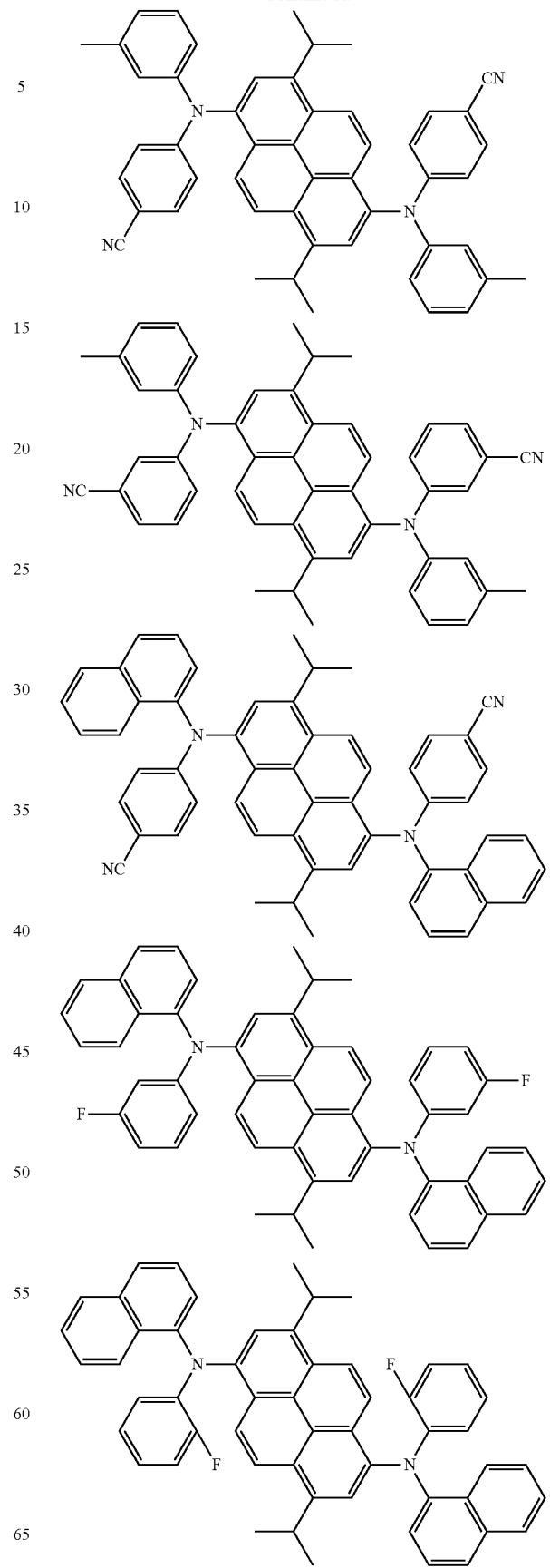

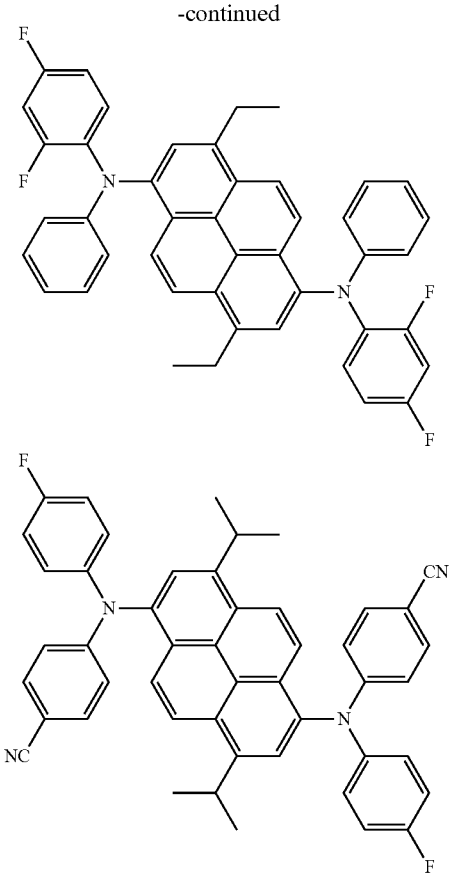

No specific restrictions are imposed on the aromatic amine derivative of the invention. For example, it can be produced from 1,6-dibromopyrene (Journal of Chemical Society, Perkin I, page 1622 (1072) or the like).

The aromatic amine derivative of the invention is suitable as the material for an organic electroluminescence device. In particular, it is preferable to use it as a doping material for the emitting layer. By using it in the emitting layer, an organic electroluminescence device which can emit blue light having a shorter wavelength as compared with conventional devices can be obtained.

It is preferred that the aromatic amine derivative of the invention be combined with an anthracene derivative represented by the following formula (10) and be used as a material for an organic electroluminescence device.

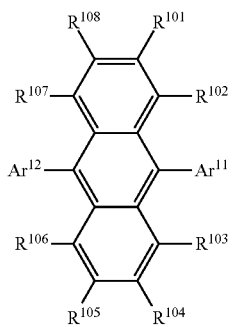

(10)

In the formula (10), $Ar^{11}$ and $Ar^{12}$ are independently a substituted or unsubstituted aryl group having 6 to 30 ring carbon atoms or a substituted or unsubstituted heterocyclic group having 5 to 30 ring atoms, and $R^{101}$ to $R^{108}$ are independently a hydrogen atom, a fluorine atom, a substituted or unsubstituted alkyl group having 1 to 10 carbon atoms, a substituted or unsubstituted cycloalkyl group having 3 to 10 carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 30 ring carbon atoms, or a substituted or unsubstituted heterocyclic group having 5 to 30 ring atoms.

In the formula (10), it is preferred that $Ar^{11}$ and $Ar^{12}$ be independently a substituted or unsubstituted fused aromatic ring group having 10 to 30 ring carbon atoms.

In the formula (10), it is preferred that $Ar^{11}$ be a substituted or unsubstituted phenyl group and $Ar^{12}$ be a substituted or unsubstituted fused aromatic ring group having 10 to 30 ring carbon atoms.

In the anthracene derivative represented by the formula (10), $Ar^{11}$ and $Ar^{12}$ are independently a group formed of 1 to 4 aromatic hydrocarbon rings which may independently be substituted. The group formed of 1 to 4 aromatic hydrocarbon rings is, for example, benzene, naphthalene, phenanthrene, fluorene, anthracene, benzoanthracene or a combination of 2 or 2 or more selected from them. The aromatic hydrocarbon ring is preferably a benzene ring. For example, benzene, naphthalene, a combination of benzene and naphthalene or benzanthracene can be mentioned. Specific examples thereof include a phenyl group, 1-naphthyl group, 2-naphthyl group, 1-naphthylphenyl group, 2-naphthylphenyl group and benzoanthracenyl group. As the substituent of these groups, an alkyl group having 1 to 4 carbon atoms, a silyl group, a silyl group substituted by an alkyl group having 1 to 4 carbon atoms, or the like can be mentioned.

Further, it is preferred that $R^{101}$ to $R^{108}$ be independently a hydrogen atom, an alkyl group having 1 to 4 carbon atoms, a silyl group or a silyl group which is substituted by an alkyl group having 1 to 4 carbon atoms. A hydrogen atom is particularly preferable.

It is preferred that the anthracene derivative represented by the formula (10) be one of the following anthracene derivatives (A), (B) and (C). An anthracene derivative is selected according to the configuration or the required properties of an organic EL device to which the anthracene derivative is used.

(Anthracene Derivative (A))

In this anthracene derivative, $Ar^{11}$ and $Ar^{12}$ in the formula (10) are independently a substituted or unsubstituted fused aromatic ring group having 10 to 30 ring carbon atoms. This anthracene derivative can be divided into one in which $Ar^{11}$ and $Ar^{12}$ are the same substituted or unsubstituted fused aromatic ring group and one in which $Ar^{11}$ and $Ar^{12}$ are different substituted or unsubstituted fused aromatic ring groups.

Specific examples of the anthracene derivative (A) include anthracene derivatives represented by the following formulas (10-1) to (10-3).

The anthracene derivative represented by the following formula (10-1) is an anthracene derivative in which $Ar^{11}$ and $Ar^{12}$ in the formula (10) are a substituted or unsubstituted 9-phenanthrenyl group.

(10-1)

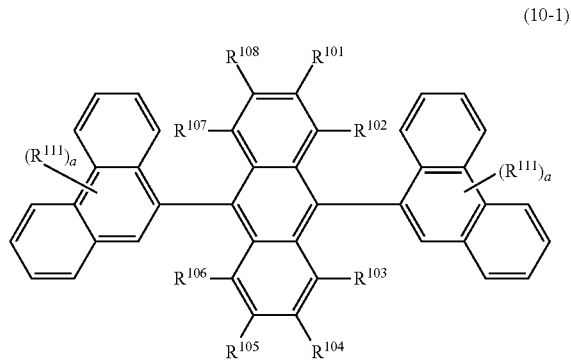

In the formula (10-1), $R^{101}$ to $R^{108}$ are the same as mentioned above.

$R^{111}$ is a substituted or unsubstituted aryl group having 6 to 30 ring carbon atoms, a substituted or unsubstituted heterocyclic group having 5 to 30 ring atoms, a substituted or unsubstituted alkyl group having 1 to 10 carbon atoms, a substituted or unsubstituted cycloalkyl group having 3 to 10 ring carbon atoms, a substituted or unsubstituted alkoxy group having 1 to 20 carbon atoms, a substituted or unsubstituted silyl group, a cyano group or a fluorine atom.

a is an integer of 0 to 9, and when a is an integer of 2 or more, plural $R^{111}$s may be the same or different on the condition that 2 substituted or unsubstituted phenanthrenyl groups are the same.

The anthracene derivative represented by the following formula (10-2) is an anthracene derivative in which $Ar^{11}$ and $Ar^{12}$ in the formula (10) are a substituted or unsubstituted 2-naphthyl group.

(10-2)

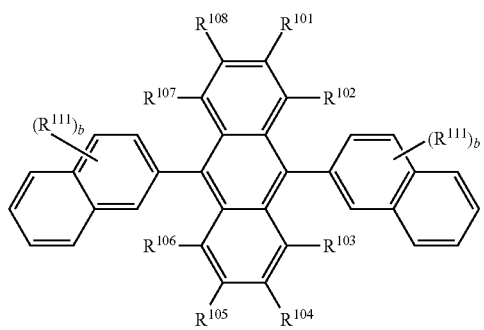

In the formula (10-2), $R^{101}$ to $R^{108}$ and $R^{111}$ are as those mentioned above, and b is an integer of 0 to 7. When b is an integer of 2 or more, plural $R^{111}$s may be the same or different on the condition that two substituted or unsubstituted 2-naphthyl groups are the same.

The anthracene derivative represented by the following formula (10-3) is an anthracene derivative in which $Ar^{11}$ and $Ar^{12}$ in the formula (10) are a substituted or unsubstituted 1-naphthyl group.

(10-3)

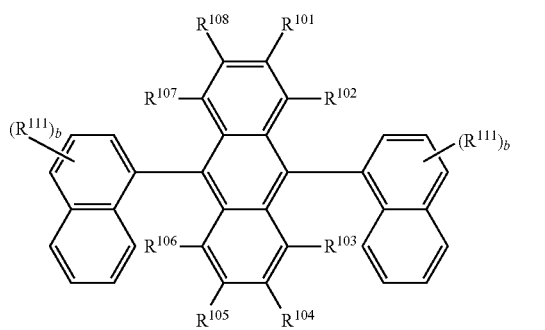

In the formula (10-3), $R^{101}$ to $R^{108}$, $R^{111}$ and b are as those mentioned above. When b is an integer of 2 or more, plural $R^{111}$s may be the same or different on the condition that two substituted or unsubstituted 1-naphthyl groups are the same.

As for the anthracene derivative in which $Ar^{11}$ and $Ar^{12}$ in the formula (10) are different substituted or unsubstituted fused aromatic ring groups, it is preferred that $Ar^{11}$ and $Ar^{12}$ be one of a substituted or unsubstituted 9-phenanthryl group, a substituted or unsubstituted 1-naphthyl group or a substituted or unsubstituted 2-naphthyl group.

Specifically, this anthracene derivative is divided into one in which $Ar^{11}$ is a 1-naphthyl group and $Ar^{12}$ is a 2-naphthyl group, one in which $Ar^{11}$ is a 1-naphthyl group and $Ar^{12}$ is a 9-phenanthryl group, and one in which $Ar^{11}$ is a 2-naphthyl group and $Ar^{12}$ is a 9-phenanthryl group.

(Anthracene Derivative (B))

This anthracene derivative is an anthracene derivative in which one of $Ar^{11}$ and $Ar^{12}$ in the formula (10) is a substituted or unsubstituted phenyl group, and the other is a substituted or unsubstituted fused aromatic ring group having 10 to 50 ring carbon atoms. Specific examples of the anthracene derivative include anthracene derivatives represented by the following formulas (10-4) and (10-5).

In the anthracene derivative represented by the following formula (10-4), $Ar^{11}$ in the formula (10) is a substituted or unsubstituted 1-naphthyl group and $Ar^{12}$ in the formula (10) is a substituted or unsubstituted phenyl group.

(10-4)

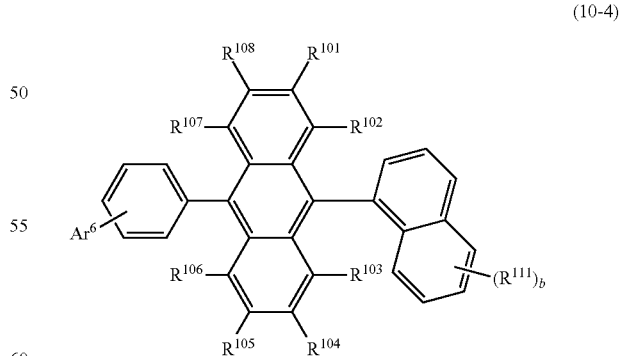

In the formula (10-4), $R^{101}$ to $R^{108}$ and $R^{111}$ are as those in the formulas (10) and (10-1).

b is an integer of 0 to 7, and when b is an integer of 2 or more, plural $R^{111}$s may be the same or different.

$Ar^6$ is a substituted or unsubstituted aryl group having 6 to 30 ring carbon atoms, a substituted or unsubstituted alkyl group having 1 to 10 carbon atoms, a substituted or unsubstituted cycloalkyl group having 3 to 10 ring carbon atoms or a substituted or unsubstituted heterocyclic group having 5 to 30 ring atoms. Ar⁶ may form a bond with a benzene ring to which it bonds. For example, Ar⁶ may form a ring such as a substituted or unsubstituted fluorenyl group or a substituted or unsubstituted dibenzofuranyl group. Preferable examples of Ar⁶ include a 9,9-dimethylfluorene-1-yl group, a 9,9-dimethylfluorene-2-yl group, a 9,9-dimethylfluorene-3-yl group, a 9,9-dimethylfluorene-4-yl group, a dibenzofuran-1-yl group, a dibenzofuran-2-yl group, a dibenzofuran-3-yl group or a dibenzofuran-4-yl group.

The anthracene derivative represented by the following formula (10-5) is an anthracene derivative in which $Ar^{11}$ in the formula (10) is a substituted or unsubstituted 2-naphthyl group and $Ar^{12}$ in the formula (10) is a substituted or unsubstituted phenyl group.

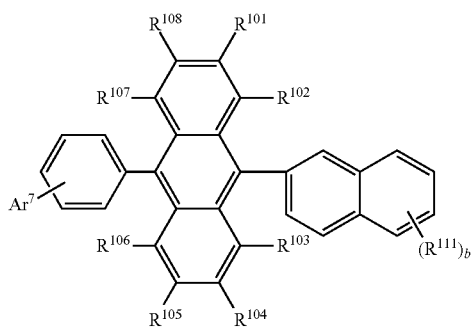

(10-5)

In the formula (10-5), $R^{101}$ to $R^{108}$, $R^{111}$ and b are as those mentioned above.

Ar⁷ is a substituted or unsubstituted aryl group having 6 to 30 ring carbon atoms, a substituted or unsubstituted alkyl group having 1 to 10 carbon atoms, a substituted or unsubstituted cycloalkyl group having 3 to 10 ring carbon atoms or a substituted or unsubstituted heterocyclic group having 5 to 30 ring atoms. Ar⁷ may form a ring with a benzene ring to which it bonds.

Preferable examples of Ar⁷ include a dibenzofuran-1-yl group, a dibenzofuran-2-yl group, a dibenzofuran-3-yl group and a dibenzofuran-4-yl group.

Ar⁷ may form a ring such as a substituted or unsubstituted fluorenyl group or a substituted or unsubstituted dibenzofuranyl group with a benzene ring to which it bonds. If b is an integer of 2 or more, plural $R^{111}$s may be the same or different.

(Anthracene Derivative (C))

This anthracene derivative is represented by the following formula (10-6). Specifically, it is preferred that the anthracene derivative be a derivative represented by one of the following formulas (10-6-1), (10-6-2) and (10-6-3).

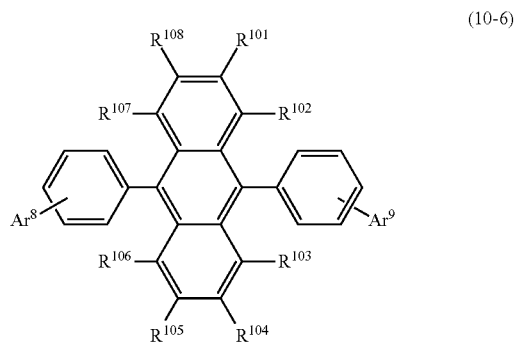

(10-6)

In the formula (10-6), $R^{101}$ to $R^{108}$ are the same as those mentioned above. Ar⁸ is the same as Ar⁶.

Ar⁸ is a substituted or unsubstituted aryl group having 6 to 30 ring carbon atoms, a substituted or unsubstituted alkyl group having 1 to 10 carbon atoms, a substituted or unsubstituted cycloalkyl group having 3 to 10 ring carbon atoms or a substituted or unsubstituted heterocyclic group having 5 to 50 ring atoms.

Ar⁸ and Ar⁹ are independently selected.

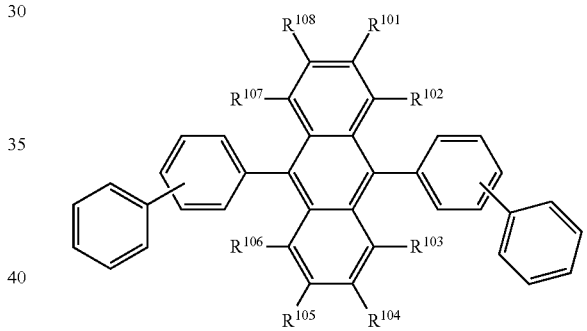

(10-6-1)

In the formula (10-6-1), $R^{101}$ to $R^{108}$ are the same as those defined above.

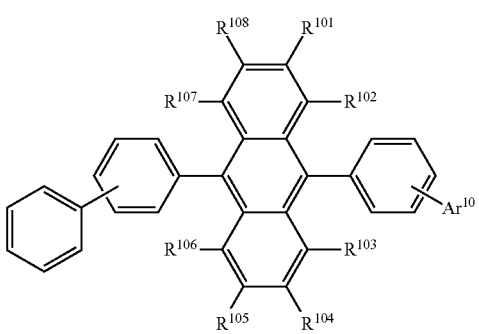

(10-6-2)

In the formula (10-6-2), $R^{101}$ to $R^{108}$ are the same as those defined above. $Ar^{10}$ is a substituted or unsubstituted fused aromatic ring group having 10 to 20 ring carbon atoms.

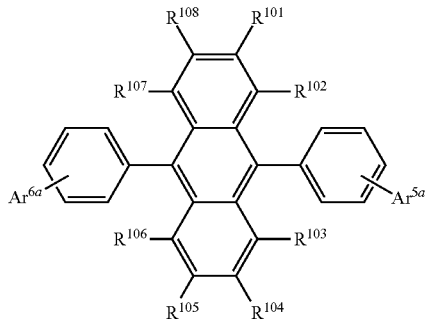

(10-6-3)

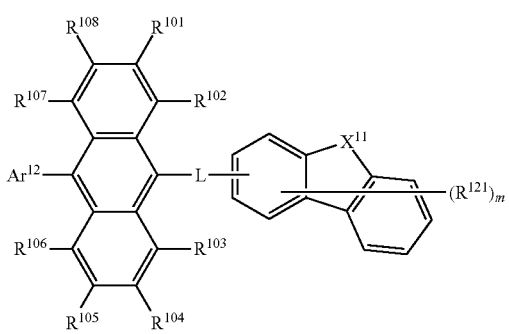

(10-8)

In the formula (10-6-3), $R^{101}$ to $R^{106}$ are the same as those in the formula (10).

$Ar^{5a}$ and $Ar^{6a}$ are independently a substituted or unsubstituted fused aromatic ring group having 10 to 20 ring carbon atoms.

Further, the following anthracene derivatives (10-7) to (10-8) are preferable.

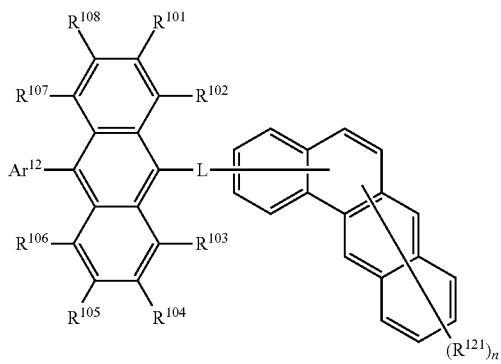

(10-7)

In the formula (10-7), $R^{101}$ to $R^{108}$ and $Ar^{12}$ are the same as those in the formula (10).

L is a single bond, a substituted or unsubstituted arylene group having 6 to 30 ring carbon atoms or a divalent substituted or unsubstituted heterocyclic group having 5 to 30 ring atoms.

$R^{121}$ is a substituted or unsubstituted aryl group having 6 to 30 ring carbon atoms, a substituted or unsubstituted heterocyclic group having 5 to 30 ring atoms, a substituted or unsubstituted alkyl group having 1 to 10 carbon atoms, a substituted or unsubstituted cycloalkyl group having 3 to 10 ring carbon atoms, a substituted or unsubstituted alkoxy group having 1 to 20 carbon atoms, a substituted or unsubstituted silyl group, a cyano group or a fluorine atom.

n is an integer of 0 to 11. If n is an integer of 2 or more, plural $R^{121}$s may be the same or different. Preferably, n is 1 to 2.

In the formula (10-8), $R^{101}$ to $R^{108}$ and $Ar^{12}$ are the same as those in the formula (10). L and $R^{121}$ are the same as those in the formula (10-7).

$X^{11}$ is an oxygen atom, a sulfur atom or —NR—. R is the same as $R^{101}$ to $R^{108}$.

m is an integer of 0 to 7. If m is an integer of 2 or more, plural $R^{121}$s may be the same or different. Preferably, m is 1 to 2.

Further, as in the anthracene derivative (10-9) shown below, it is preferred that, in the anthracene derivative (10), $Ar^{11}$ be an unsubstituted phenyl group and $Ar^{12}$ be a substituted or unsubstituted aryl group having 6 to 30 ring carbon atoms or a substituted or unsubstituted heterocyclic group having 5 to 30 ring atoms.

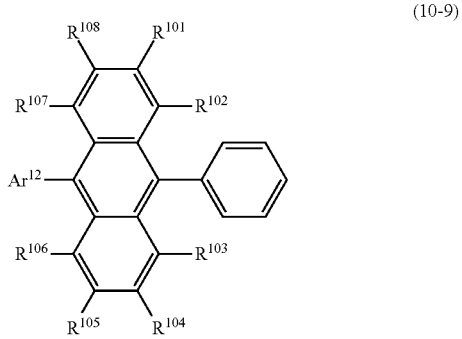

(10-9)

In the formula (10-9), $R^{101}$ to $R^{108}$ and $Ar^{12}$ are the same as those in the formula (10).

Similarly, as in the anthracene derivative (10-10) shown below, it is preferred that, in the anthracene derivative (10), it is preferred that $Ar^{11}$ be an unsubstituted phenanthrenyl group, and $Ar^{12}$ be a substituted or unsubstituted aryl group having 6 to 30 ring carbon atoms or a substituted or unsubstituted heterocyclic group having 5 to 30 ring atoms.

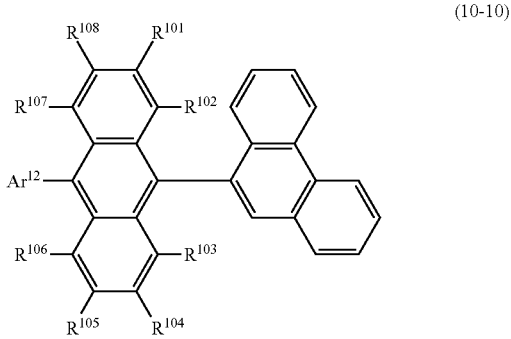

(10-10)

In the formula (10-10), $R^{101}$ to $R^{108}$ and $Ar^{12}$ are the same as those in the formula (10).

As examples of the aryl group having 6 to 30 ring carbon atoms represented by $R^{101}$ to $R^{108}$, $R^{111}$, $R^{121}$, $Ar^5$ to $Ar^9$, $Ar^{11}$ and $Ar^{12}$, a phenyl group, a naphthyl group, an anthryl group, a phenanthryl group, a naphthacenyl group, a pyrenyl group, a chrysenyl group, a benzo[c]phenanthryl group, a benzo[g]chrysenyl group, a triphenylenyl group, a fluorenyl group, a 9,9-dimethylfluorene-2-yl group, a benzofluorenyl group, a dibenzofluorenyl group, a benzo[a]anthryl group, a biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group or the like can be given. The fused aromatic ring group having 10 to 30 ring carbon atoms means a group, of the above-mentioned aryl groups, in which two or more ring structures are fused. Examples thereof include a naphthyl group, a phenanthryl group, an anthryl group, a chrysenyl group, a benzoanthryl group, a benzophenanthryl group, a triphenylenyl group, a benzochrysenyl group, an indenyl group, a fluorenyl group, a 9,9-dimethylfluorenyl group, a benzofluorenyl group, a dibenzofluorenyl group, a fluoranthenyl group and a benzofluoranthenyl group.

The fused aromatic ring group is preferably an unsubstituted phenyl group, a substituted phenyl group and a substituted or unsubstituted aryl group having 10 to 14 ring carbon atoms (for example, a 1-naphthyl group, a 2-naphthyl group and a 9-phenanthryl group), a substituted or unsubstituted fluorenyl group (2-fluorenyl group) and a substituted or unsubstituted pyrenyl group (1-pyrenyl group, 2-pyrenyl group and 4-pyrenyl group).

The aryl group having 6 to 30 ring carbon atoms may be substituted by a substituent such as an alkyl group, a cycloalkyl group, an aryl group and a heterocyclic group. Examples of the substituents are the same as the substituents mentioned above. As the substituent, an aryl group and a heterocyclic group are preferable.

As the fused aromatic ring group having 10 to 20 ring carbon atoms represented by $Ar^{5a}$, $Ar^{6a}$ and $Ar^{10}$, a naphthyl group, an anthryl group, a phenanthryl group, a naphthacenyl group, a pyrenyl group, a fluorenyl group or the like can be given. In particular, a 1-naphthyl group, a 2-naphthyl group, a 9-phenanthryl group and a fluorenyl group (2-fluorenyl group) are preferable. The fused aromatic ring group having 10 to 20 ring carbon atoms may be substituted by a substituent such as an alkyl group, a cycloalkyl group, an aryl group or a heterocyclic group. Examples of the substituents are the same as the substituents mentioned above. As the substituent, an aryl group and a heterocyclic group are preferable.

Examples of the heterocyclic group having 5 to 30 ring atoms of $R^{101}$ to $R^{108}$, $R^{111}$, $Ar^5$ to $Ar^6$ and $Ar^{11}$ to $Ar^{12}$ include a pyrrolyl group, pyrazinyl group, pyridinyl group, indolyl group, isoindolyl group, furyl group, benzofuranyl group, isobenzofuranyl group, dibenzofuranyl group, dibenzothiophenyl group, quinolyl group, isoquinolyl group, quinoxalinyl group, carbazolyl group, phenanthrydinyl group, acridinyl group, phenanthronyl group, phenazinyl group, phenothiazinyl group, phenoxazinyl group, oxazolyl group, oxadiazolyl group, furazanyl group, thienyl group, methylpyrrolyl group, 2-t-butylpyrrolyl group, 3-(2-phenylpropyl)pyrrolyl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group. Of these, a 1-benzofuranyl group, 2-benzofuranyl group, 3-benzofuranyl group, 4-benzofuranyl group, 1-dibenzothiophenyl group, 2-group, 3-dibenzothiophenyl group, 4-dibenzothiophenyl group, 1-carbazolyl group, 2-carbazolyl group, 3-carbazolyl group, 4-carbazolyl group and 9-carbozolyl group are preferable.

The heterocyclic group having 5 to 30 ring atoms may be substituted by a substituent such as an alkyl group, cycloalkyl group, aryl group and heterocyclic group, and examples of the substituent include the same groups as the above-mentioned substituents. As the substituent, an aryl group and a heterocyclic group are preferable.

Examples of the alkyl group having 1 to 10 carbon atoms of $R^{101}$ to $R^{108}$, $R^{111}$, $R^{121}$, and $Ar^5$ to $Ar^9$ include a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group and 1,2,3-tricyanopropyl group.

Of these, a methyl group, ethyl group, propyl group, isopropyl group, n-butyl group, s-butyl group, isobutyl group and t-butyl group are preferable. The alkyl group having 1 to 10 carbon atoms may be substituted by a substituent such as an alkyl group, cycloalkyl group, aryl group and heterocyclic group, and examples of the substituent include the same groups as the above-mentioned substituents. As the substituent, an aryl group and a heterocyclic group are preferable.

Examples of the cycloalkyl group having 3 to 10 ring carbon atoms of $R^{101}$ to $R^{108}$, $R^{111}$, $R^{121}$, and $Ar^5$ to $Ar^9$ include a cyclopropyl group, cyclobutyl group, cyclopentyl group, cyclohexyl group, 4-methylcyclohexyl group, 1-adamantyl group, 2-adamantyl group, 1-norbornyl group and 2-norbornyl group. Of these, cyclopentyl and cyclohexyl are preferable. The cycloalkyl group having 3 to 8 ring carbon atoms may be substituted by a substituent such as an alkyl group, cycloalkyl group, aryl group and heterocyclic group, and examples of the substituent include the same groups as the above-mentioned substituents. As the substituent, an aryl group and heterocyclic group are preferable.

Examples of the alkylsilyl group and arylsilyl group of $R^{101}$ to $R^{108}$, $R^{111}$, and $R^{121}$ include a trimethylsilyl group, triethylsilyl group, t-butyldimethylsilyl group, vinyldimethylsilyl group, propyldimethylsilyl group and triphenylsilyl group. The silyl group may be substituted by a substituent such as an alkyl group, cycloalkyl group, aryl group and heterocyclic group, and examples of the substituent include the same groups as the above-mentioned substituents. As the substituent, an aryl group and a heterocyclic group are preferable.

The alkoxy group having 1 to 20 carbon atoms of $R^{101}$ to $R^{108}$, $R^{111}$ and $R^{121}$ is represented by —OZ, and Z is selected from the substituted or unsubstituted alkyl group of $R^{101}$ to $R^{108}$. The alkyl group may be substituted by a substituent such as an alkyl group, cycloalkyl group, aryl group and heterocyclic group, and examples of the substituent include the same groups as the above-mentioned substituents. As the substituent, an aryl group and heterocyclic group are preferable.

The aryloxy group having 6 to 20 carbon atoms of $R^{101}$ to $R^{108}$, $R^{111}$ and $R^{121}$ is represented by —OZ, and Z is selected from the substituted or unsubstituted aryl group of $R^{101}$ to $R^{108}$. The aryl group may be substituted by a substituent such as an alkyl group, cycloalkyl group, aryl group and heterocyclic group, and examples of the substituent include the same groups as the above-mentioned substituents. As the substituent, an aryl group and a heterocyclic group are preferable.

As the substituted or unsubstituted arylene group having 6 to 30 ring carbon atoms or the substituted or unsubstituted divalent heterocyclic group having 5 to 30 ring atoms of L in formulas (10-7) and (10-8), divalent groups of the aryl group and heterocyclic group described above can be given.

Specific examples of the anthracene derivative represented by the formula (10) can be given as follows:

EM1
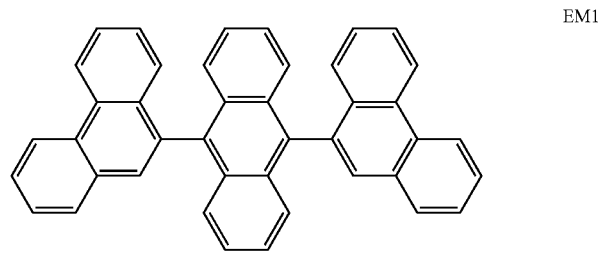

EM2
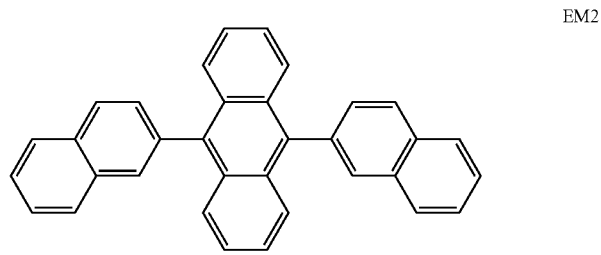

EM3
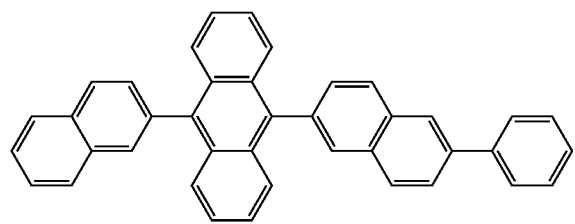

EM4
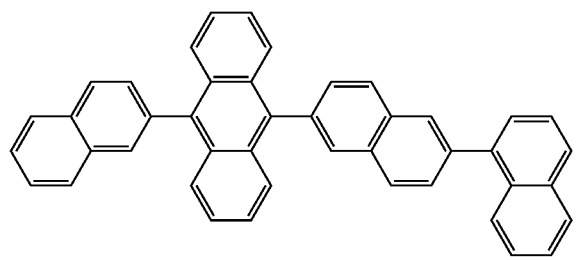

EM5
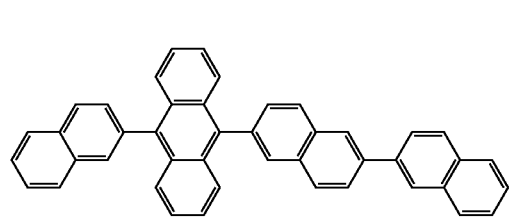

EM6
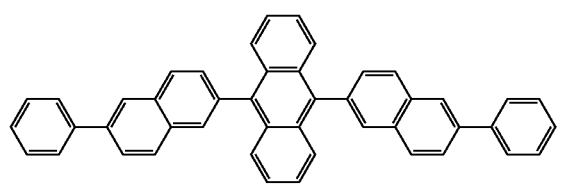

EM7
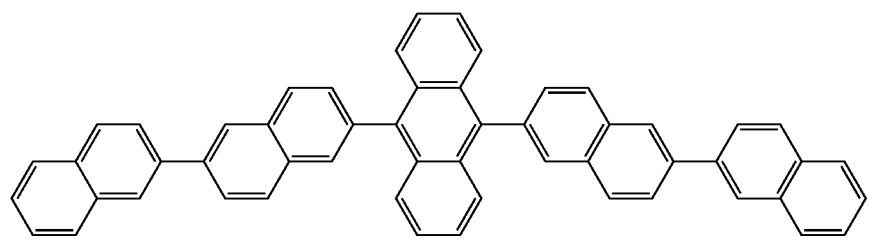

-continued
EM8
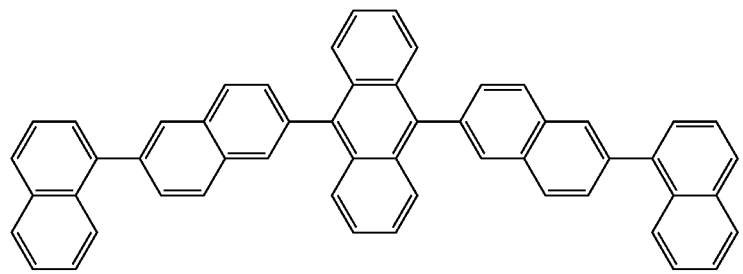
EM9
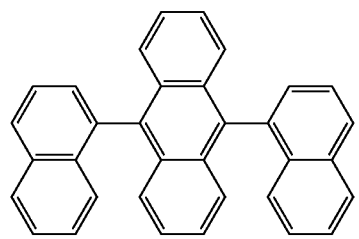
EM10
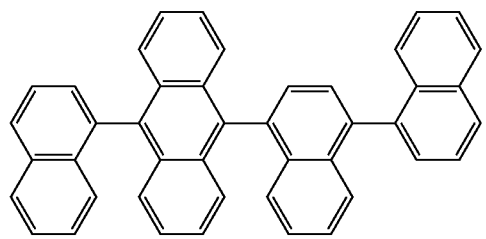
EM11
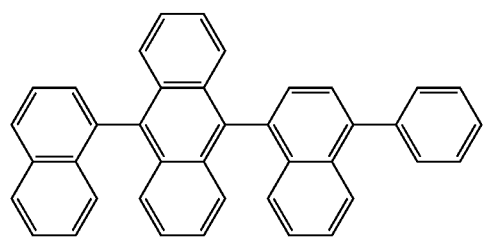
EM12
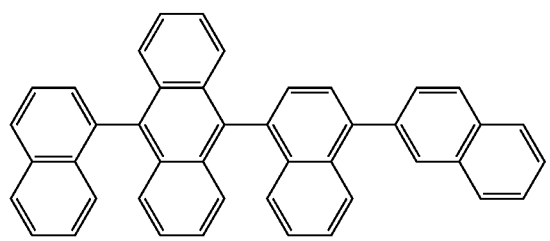
EM13
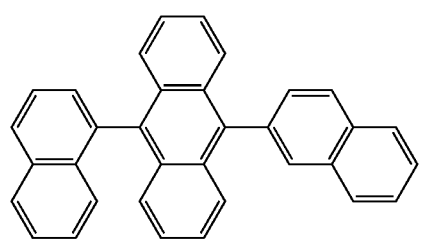
EM14
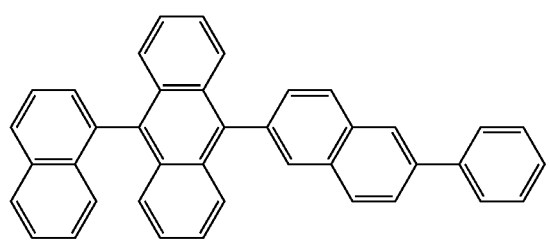
EM15
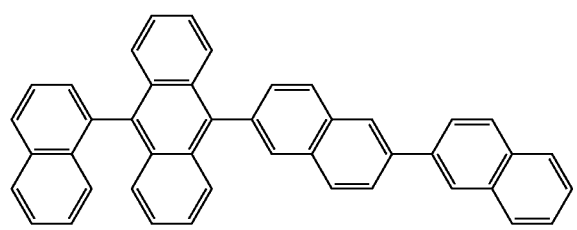
EM16
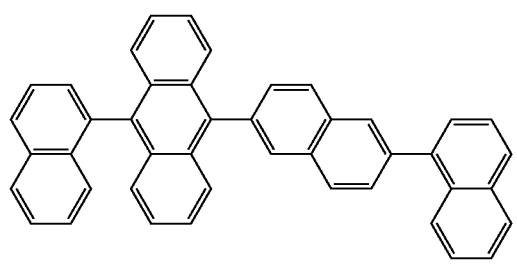
EM17
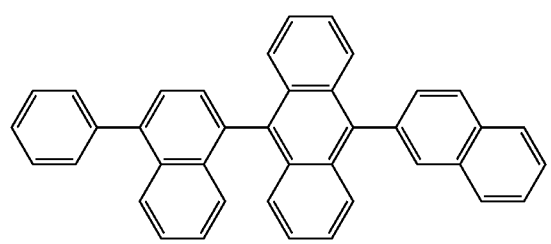
EM18
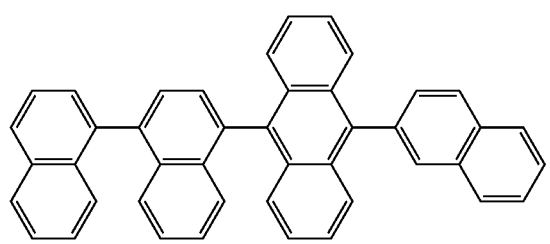

-continued
EM19
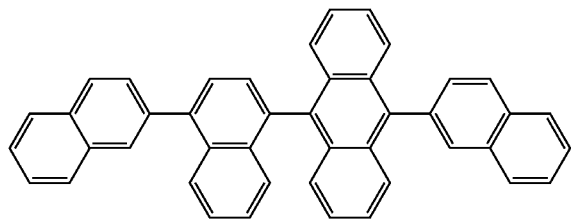
EM20
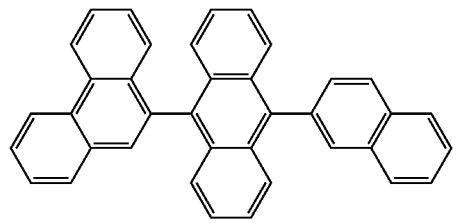
EM21
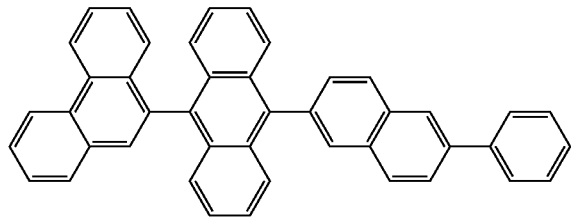
EM22
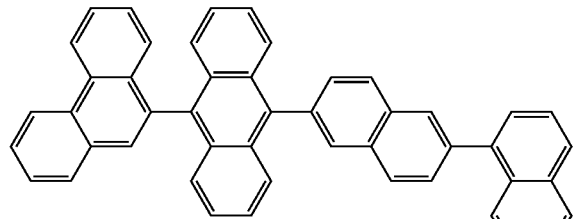
EM23
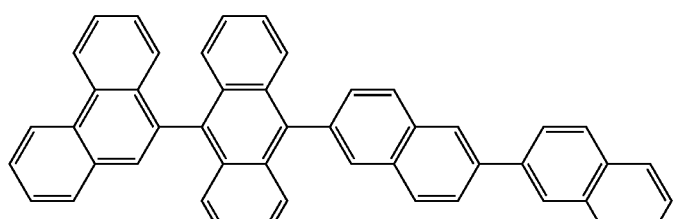
EM24
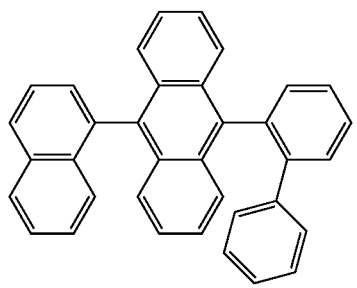
EM25
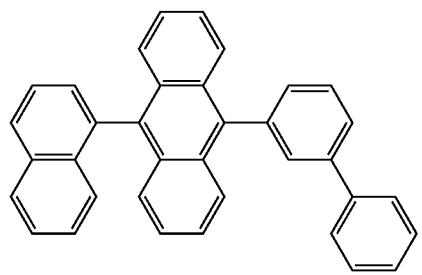
EM26
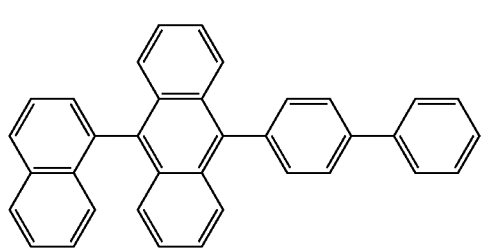
EM27
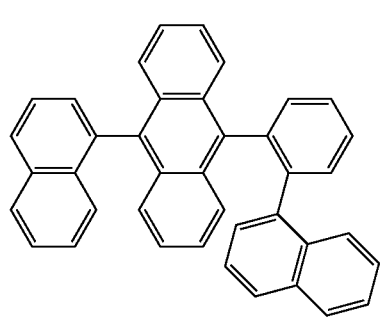
EM28
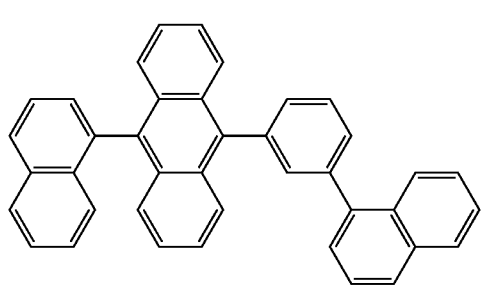
EM29
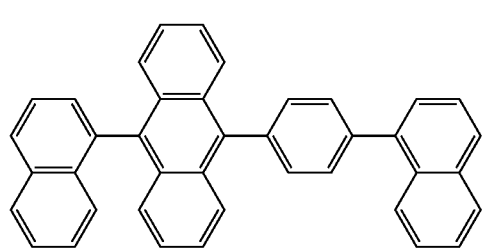

-continued
EM30
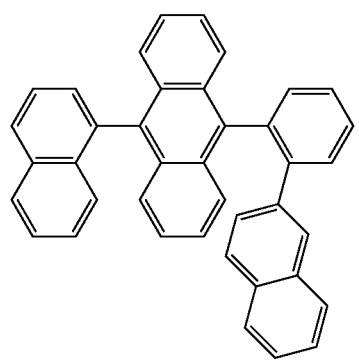
EM31
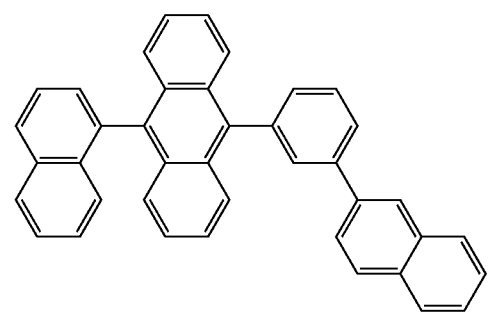
EM32
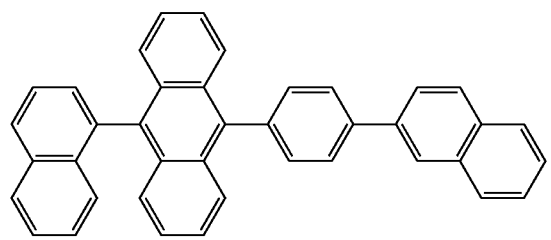
EM33
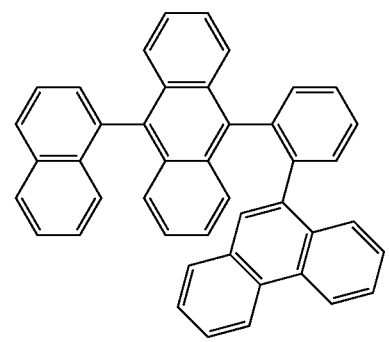
EM34
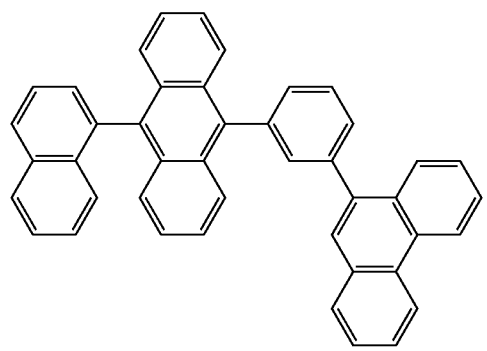
EM35
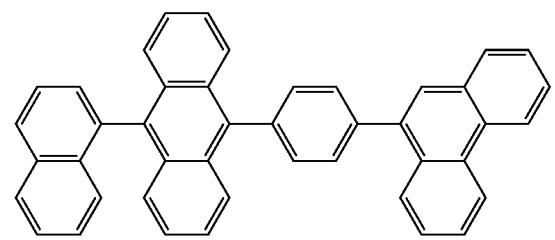
EM36
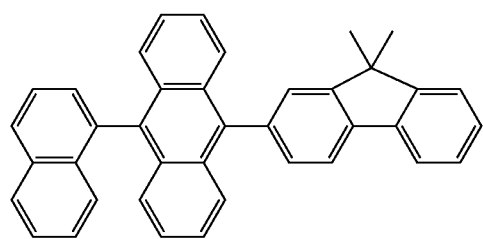
EM37
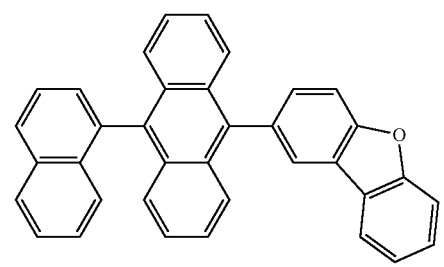

-continued
EM38
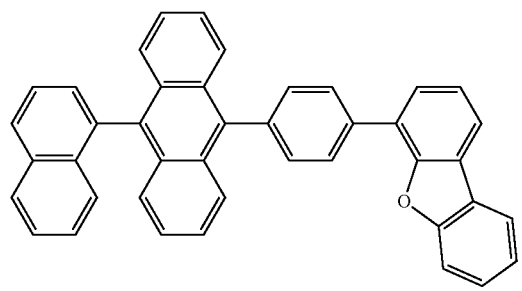
EM39
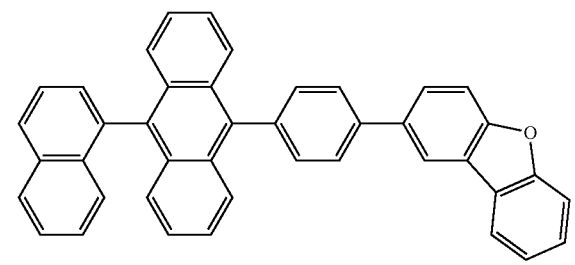
EM40
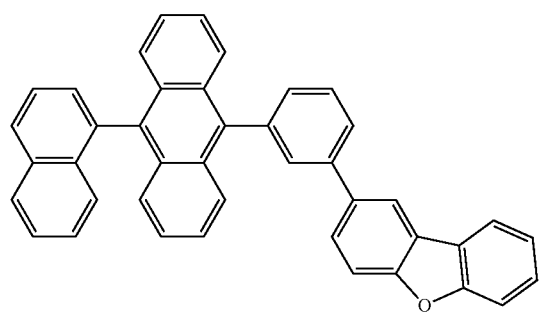
EM41
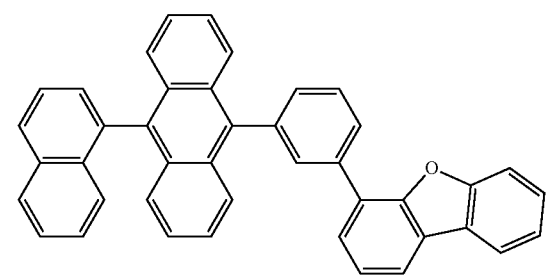
EM42
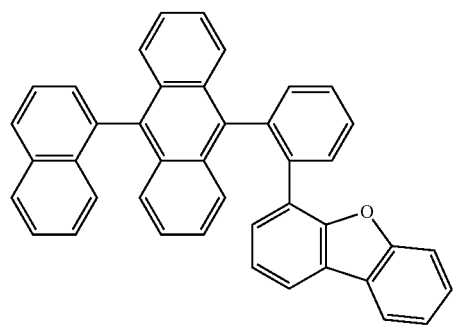
EM43
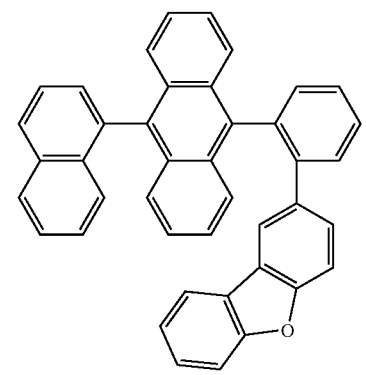
EM44
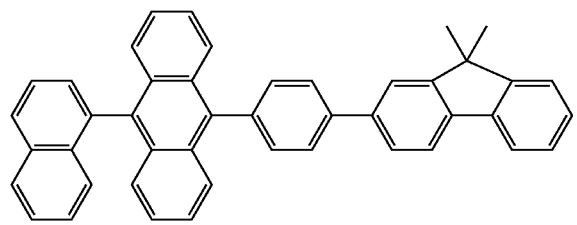
EM45
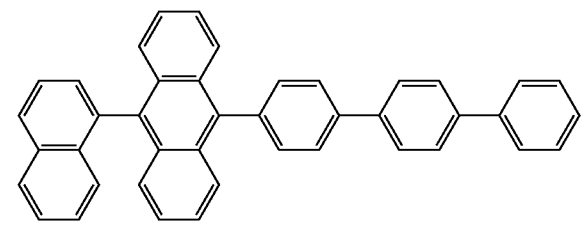

-continued
EM46
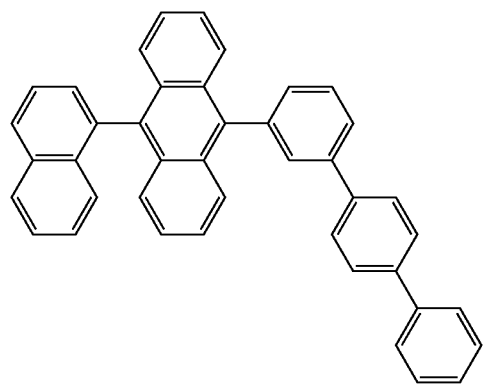
EM47
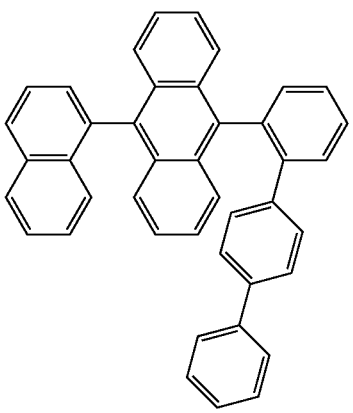
EM48
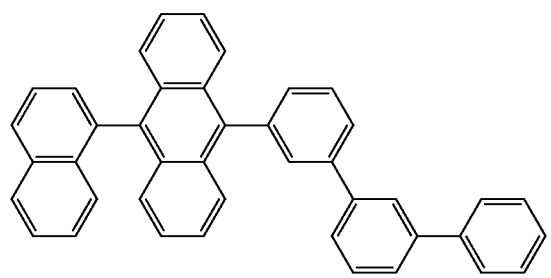
EM49
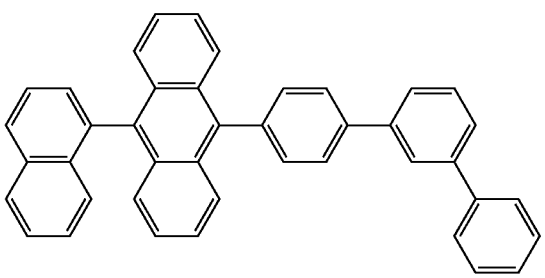
EM50
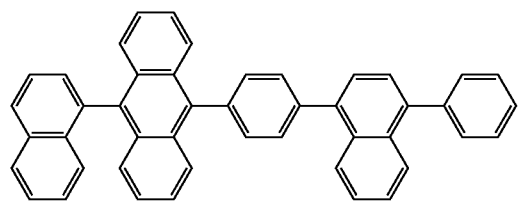
EM51
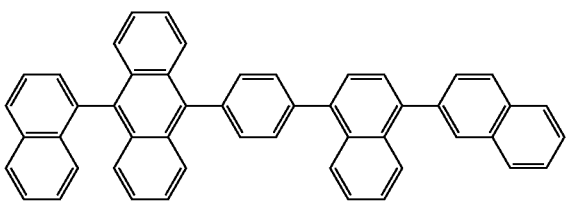
EM52
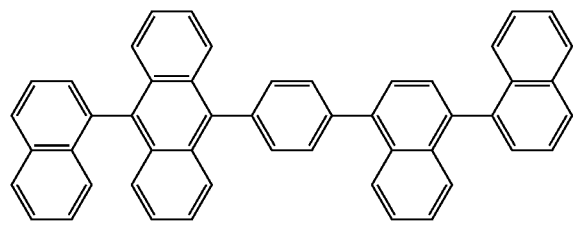
EM53
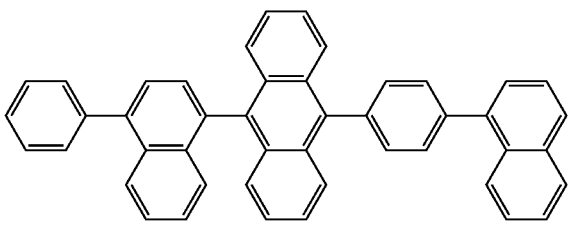
EM54
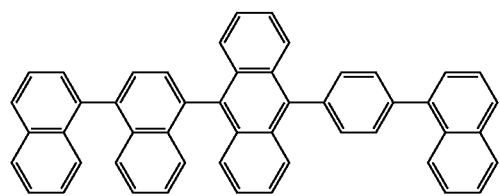
EM55
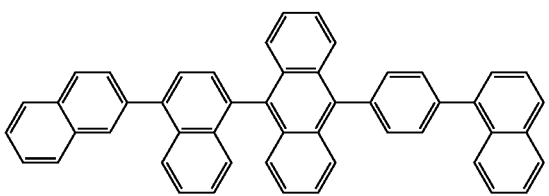

-continued
EM56
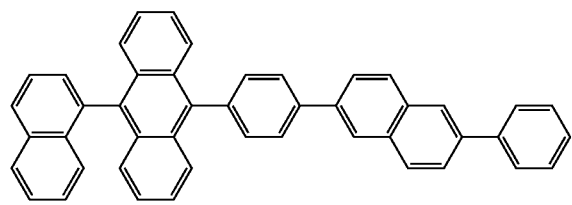
EM57
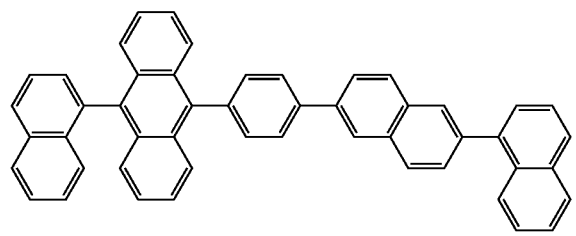
EM58
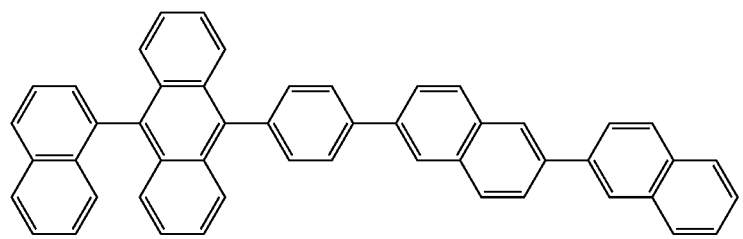
EM59
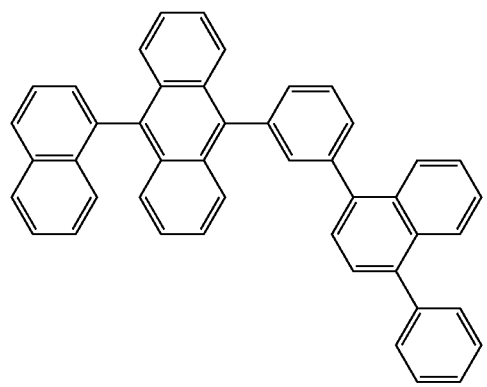
EM60
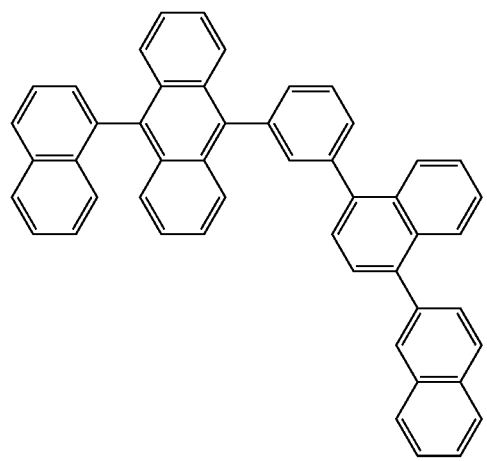
EM61
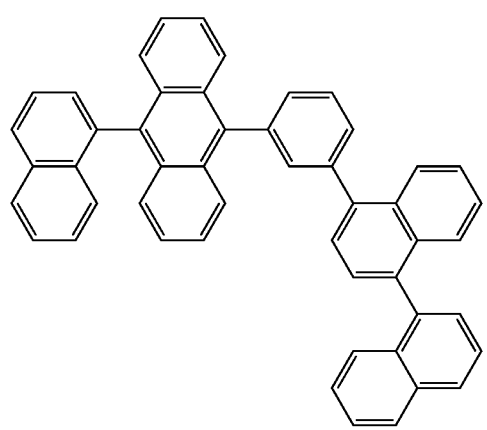
EM62
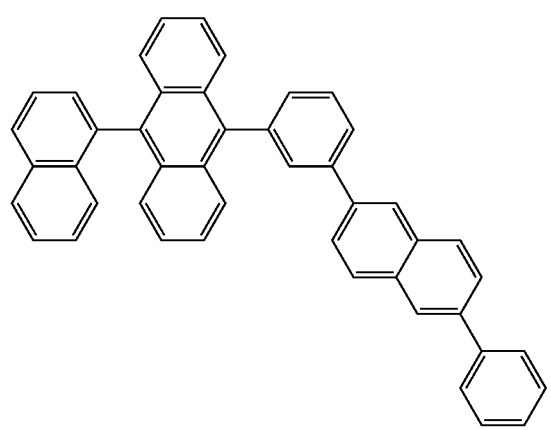

-continued
EM63
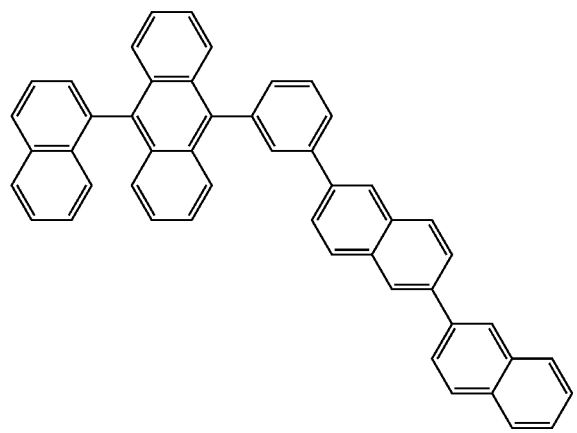
EM64
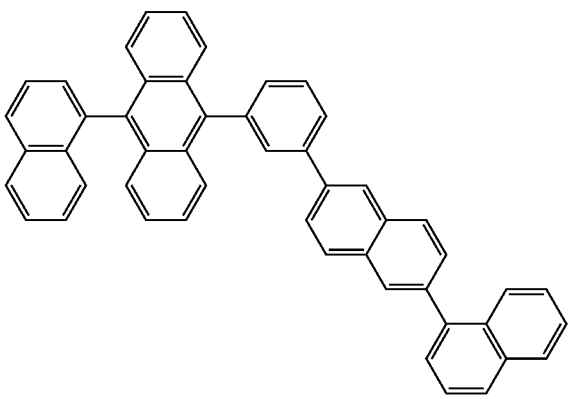
EM65
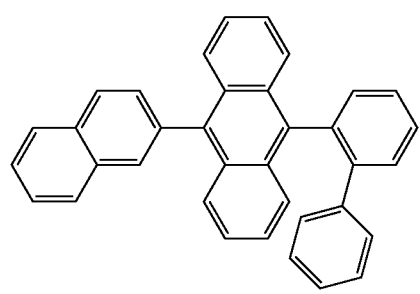
EM66
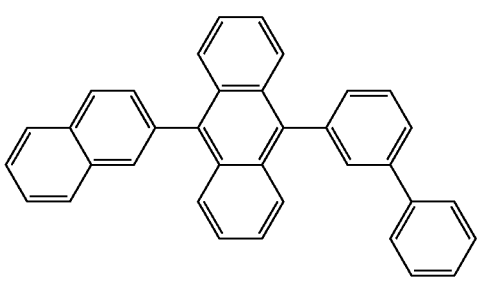
EM67
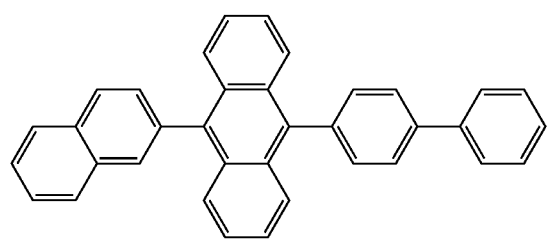
EM68
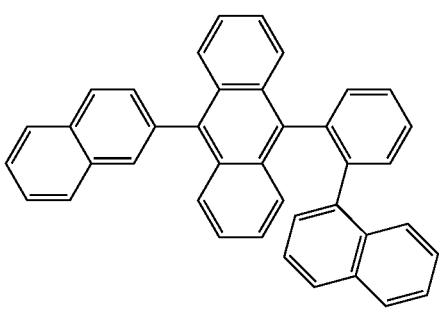
EM69
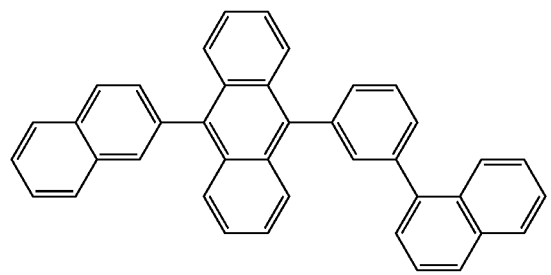
EM70
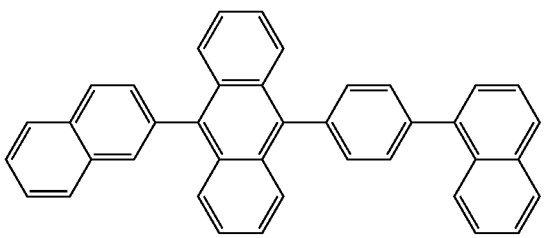

-continued
EM71
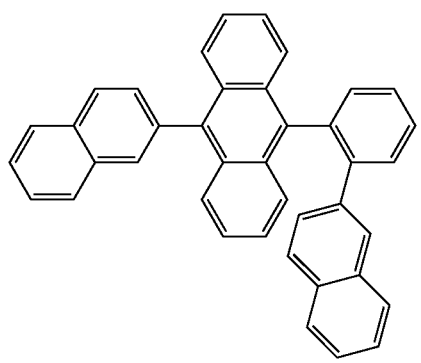
EM72
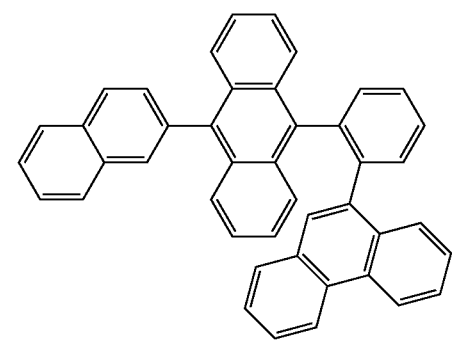
EM73
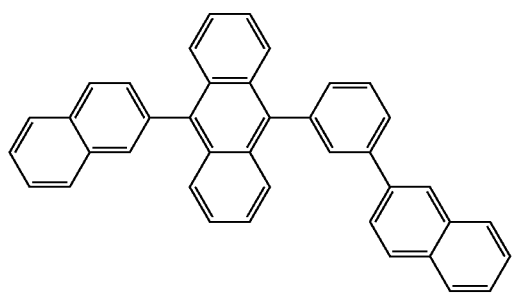
EM74
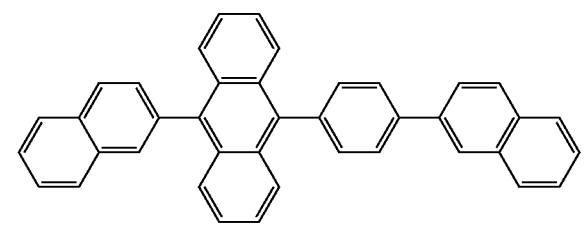
EM75
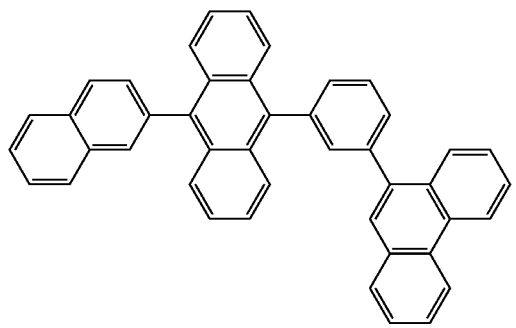
EM76
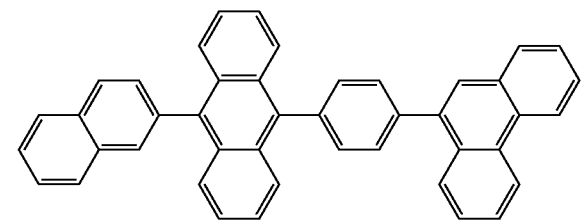
EM77
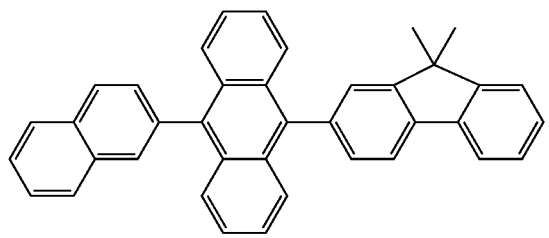
EM78
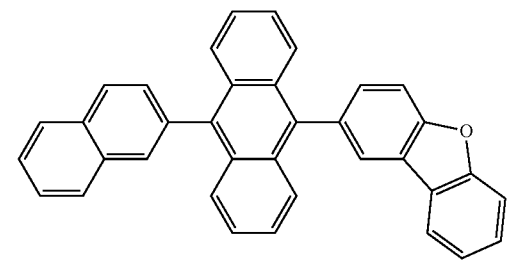
EM79
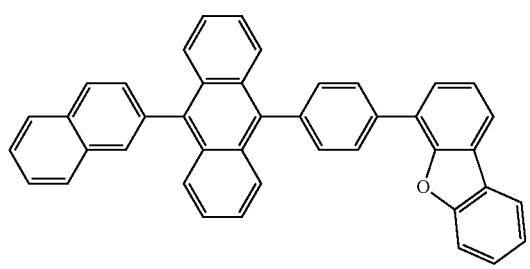
EM80
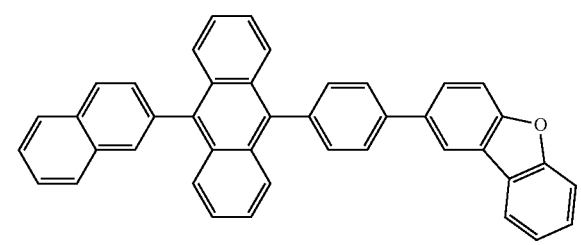

-continued
EM81
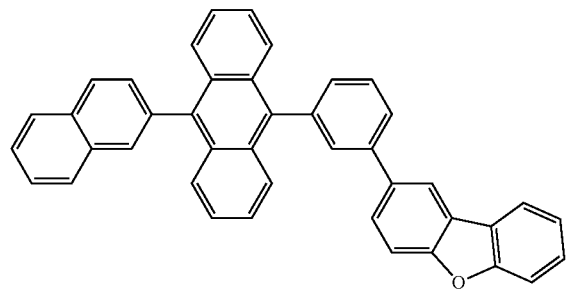
EM82
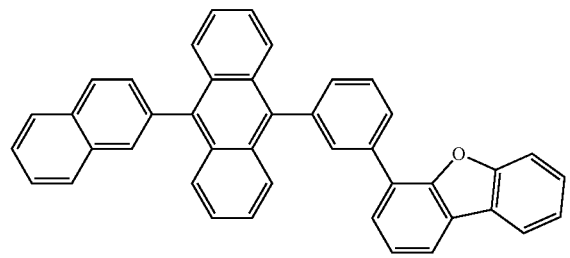
EM83
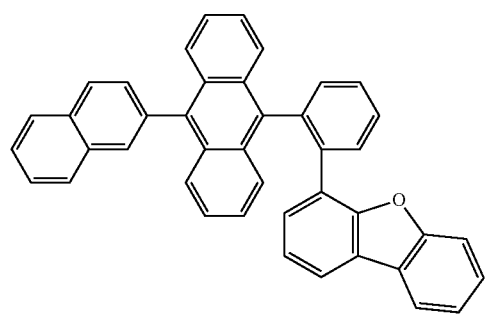
EM84
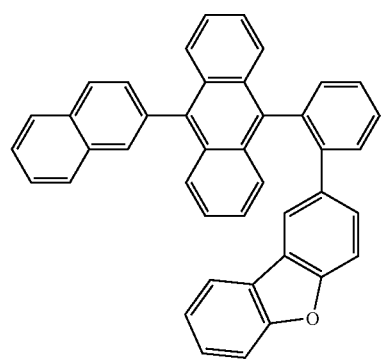
EM85
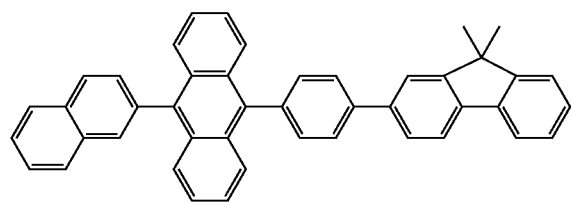
EM86
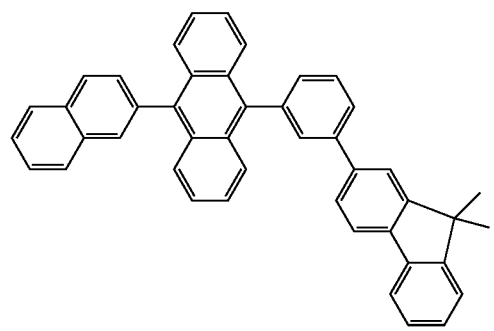
EM87
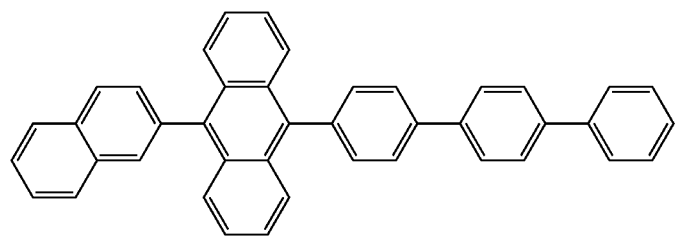

-continued
EM88
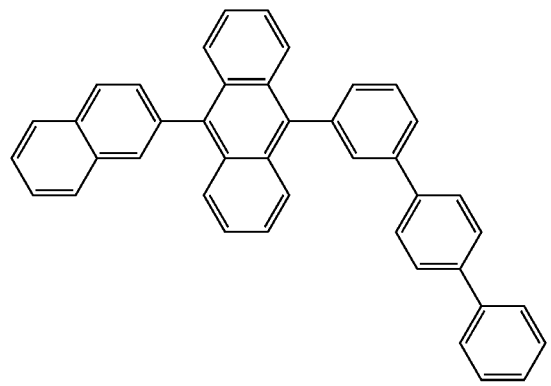
EM89
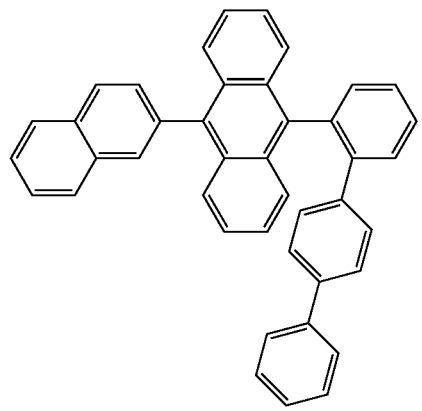
EM90
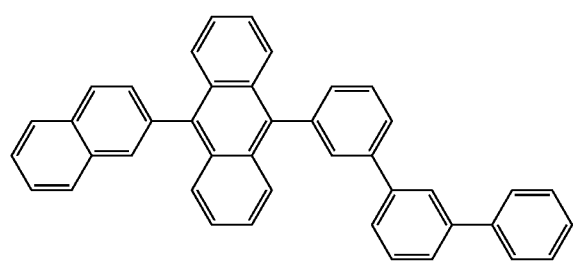
EM91
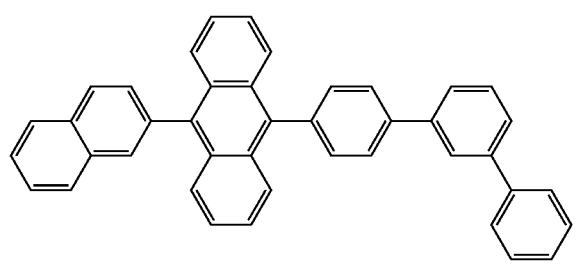
EM92
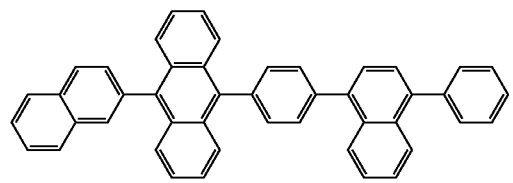
EM93
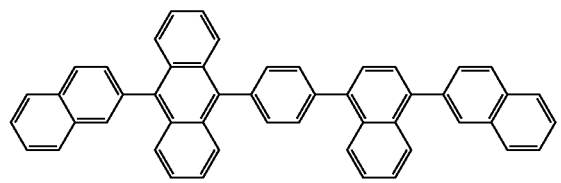
EM94
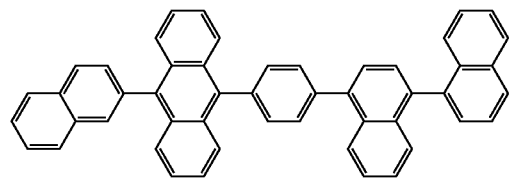
EM95
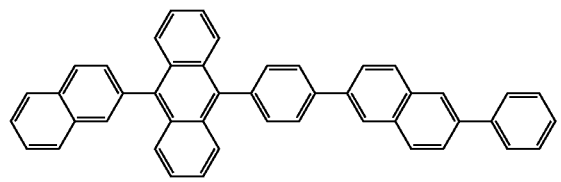
EM96
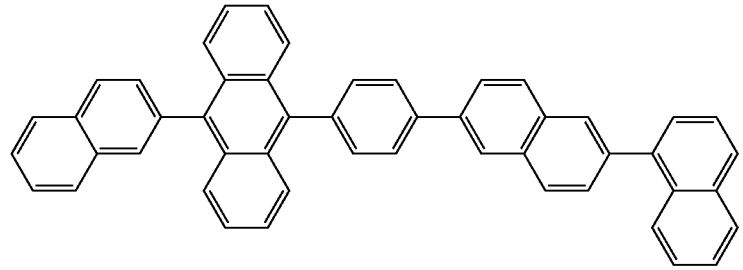
EM97
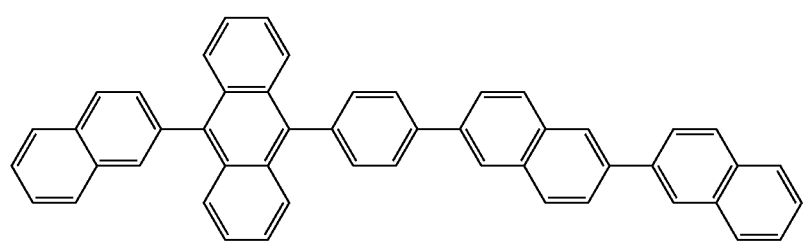

-continued
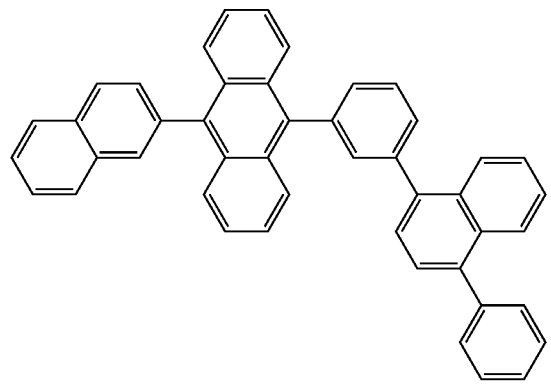

-continued
EM106
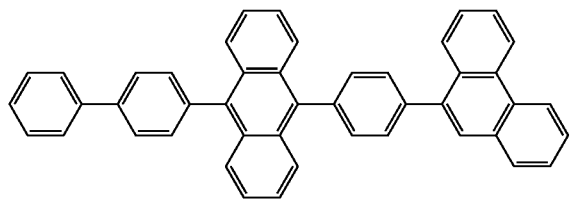
EM107
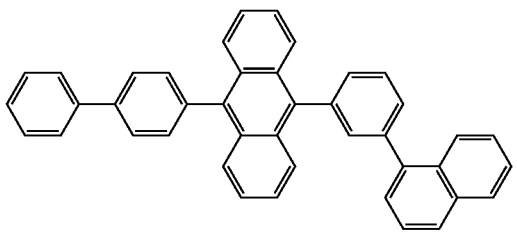
EM108
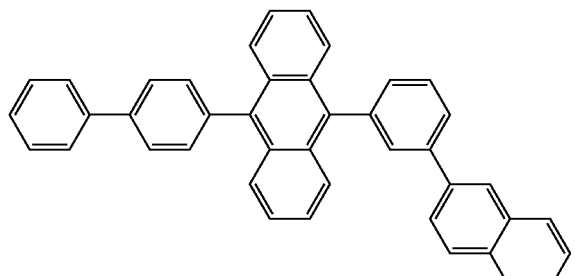
EM109
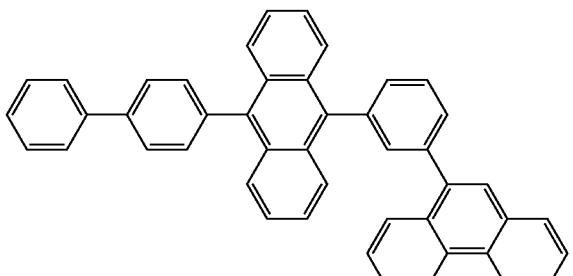
EM110
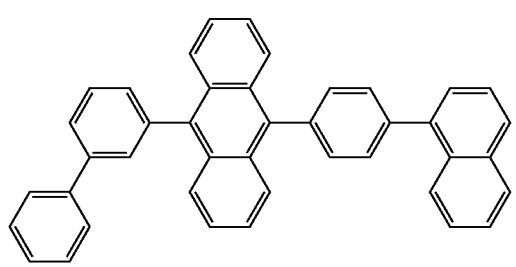
EM111
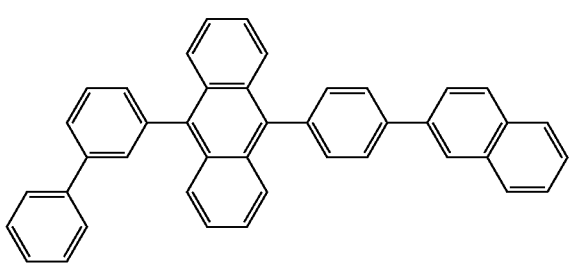
EM112
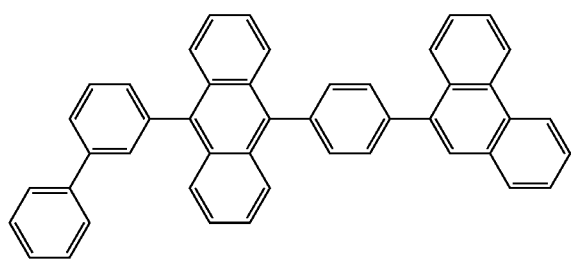
EM113
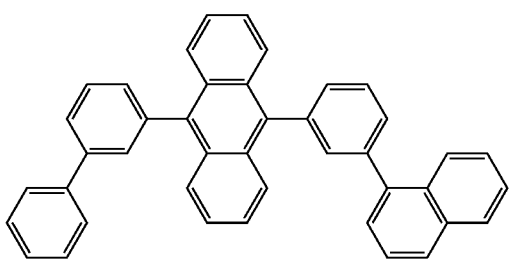
EM114
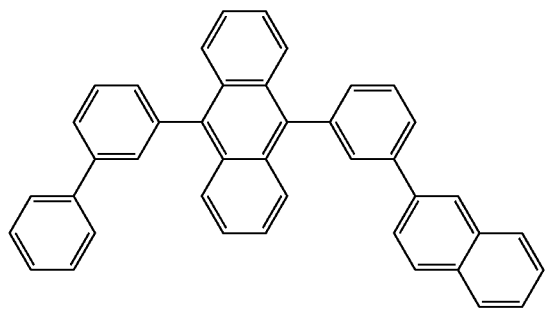
EM115
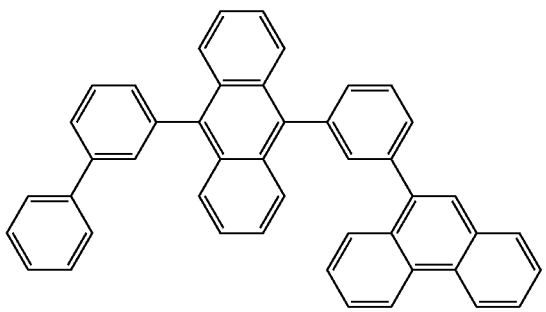

-continued
EM116
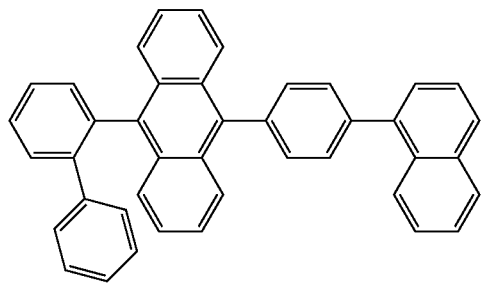
EM117
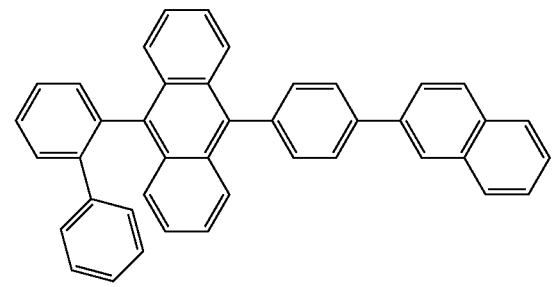
EM118
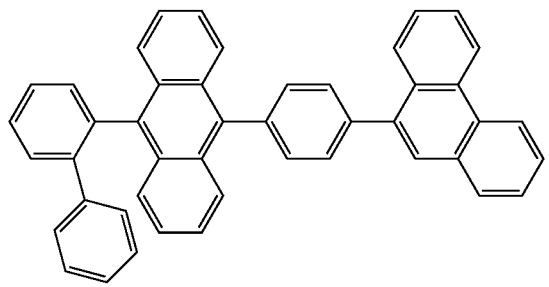
EM119
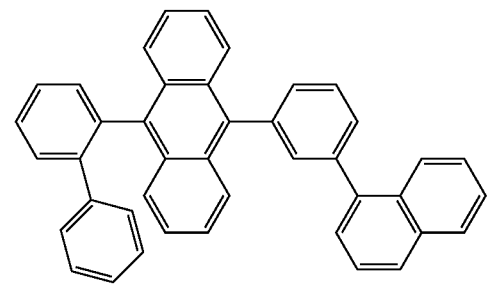
EM120
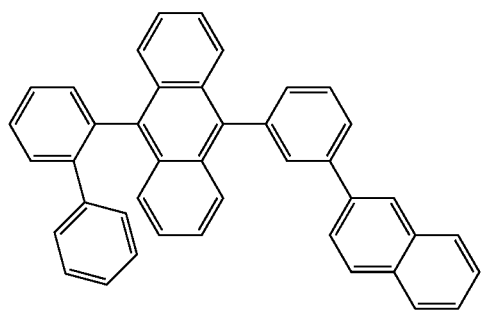
EM121
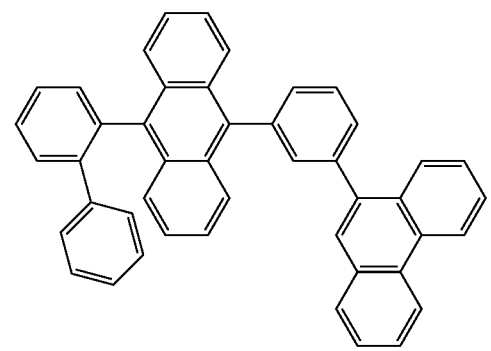
EM122
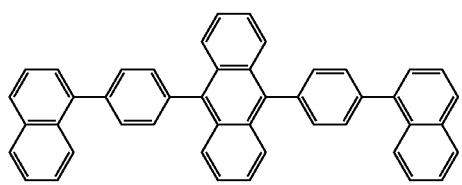
EM123
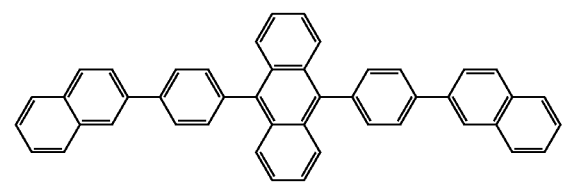
EM124
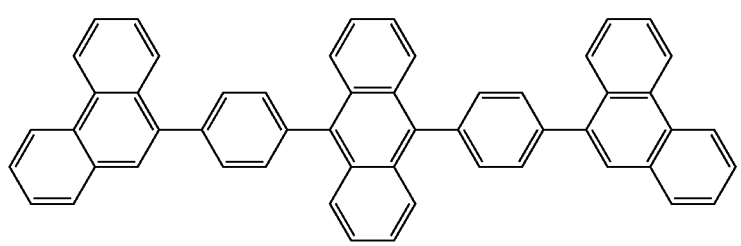

-continued
EM125
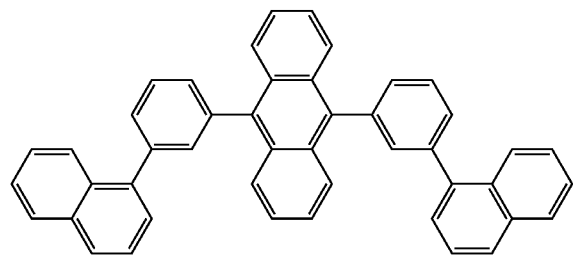
EM126
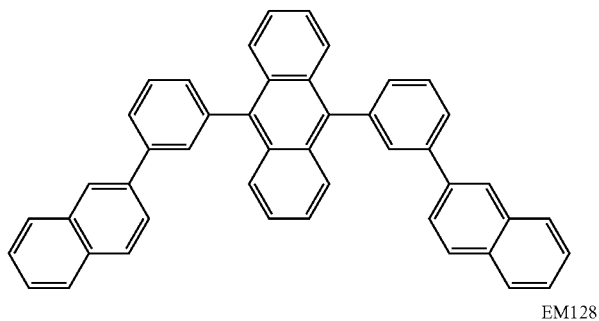
EM127
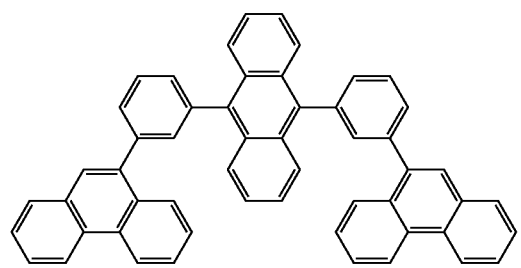
EM128
EM129
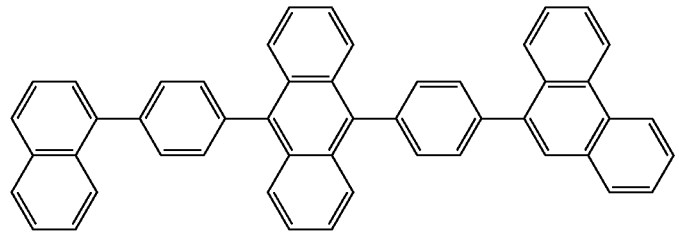
EM130
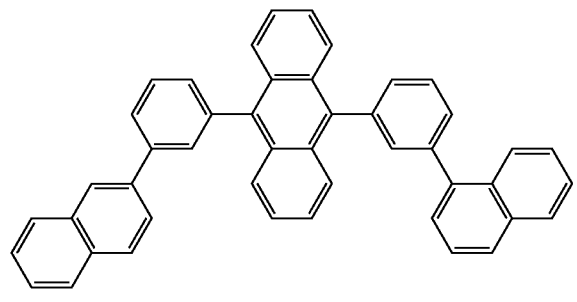
EM131
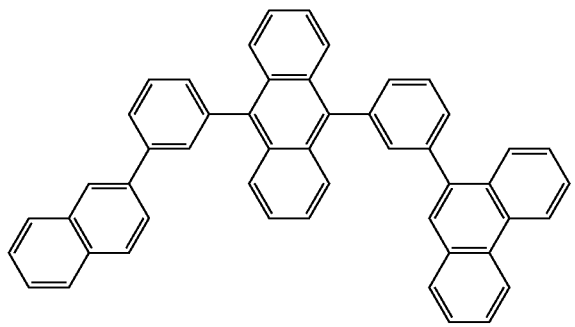
EM132
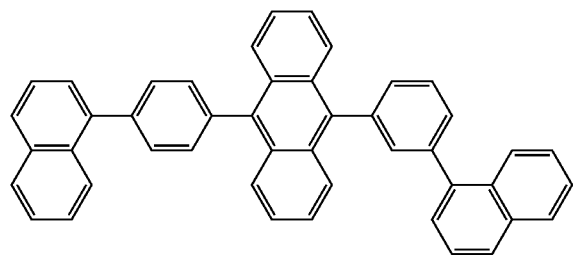
EM133
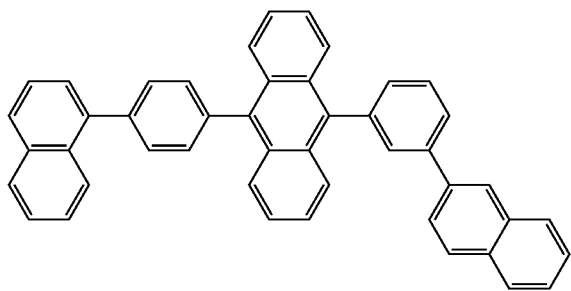

-continued
EM134
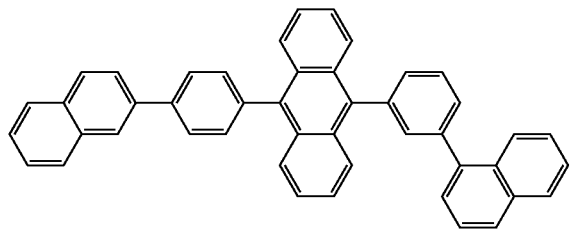
EM135
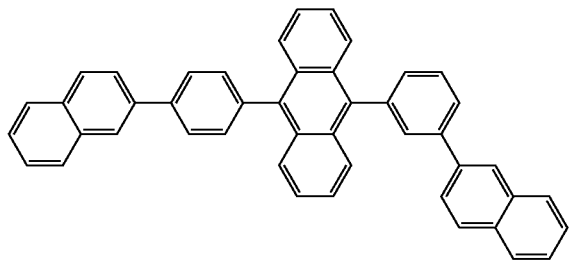
EM136
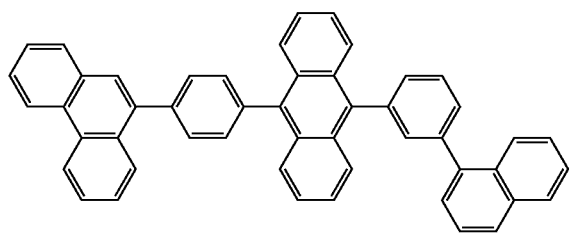
EM137
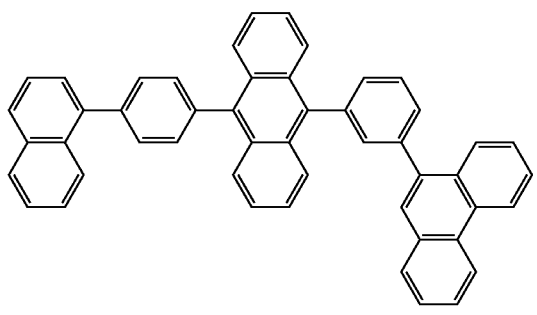
EM138
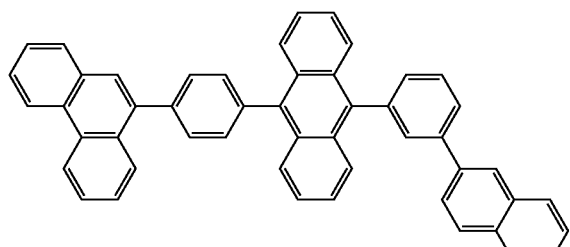
EM139
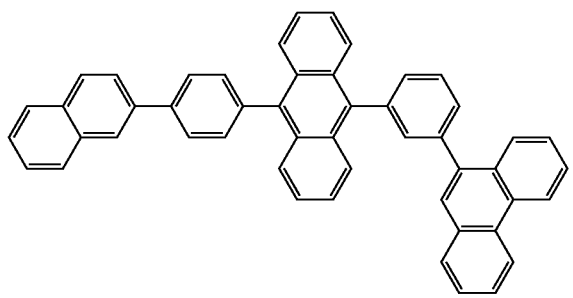
EM140
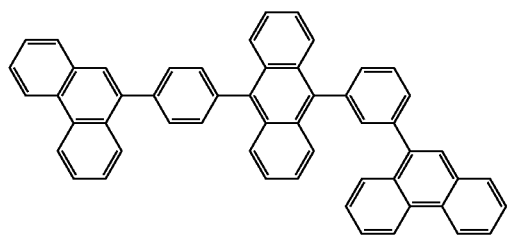
EM141
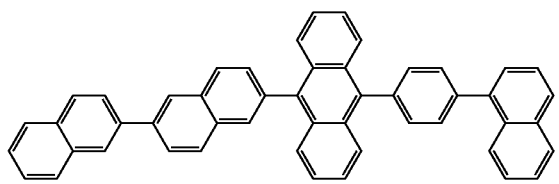
EM142
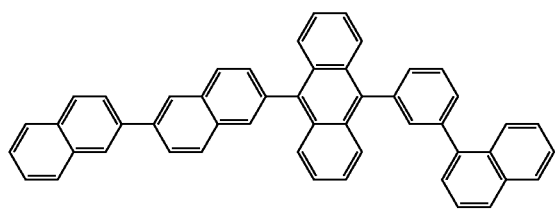
EM143
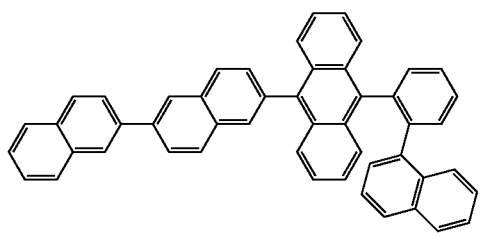

-continued
EM144
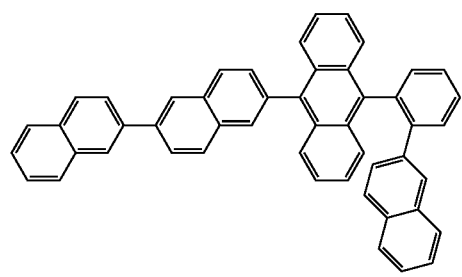
EM145
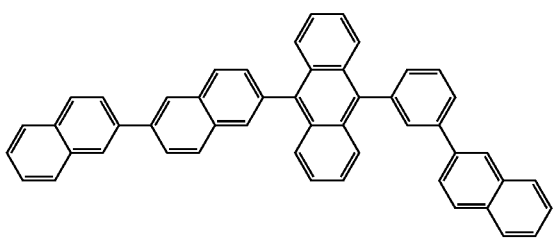
EM146
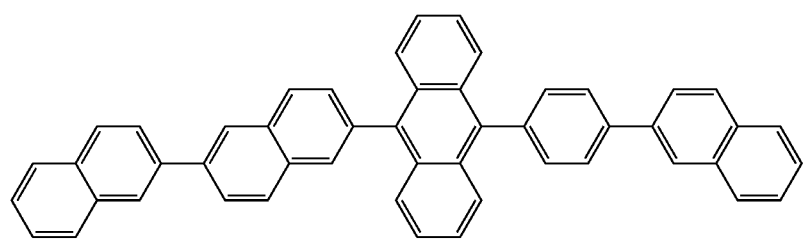
EM147
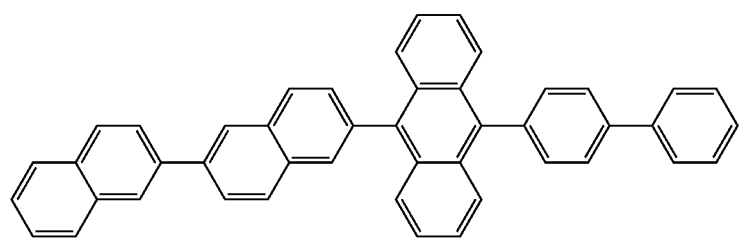
EM148
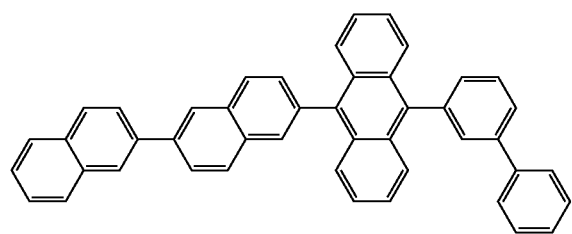
EM149
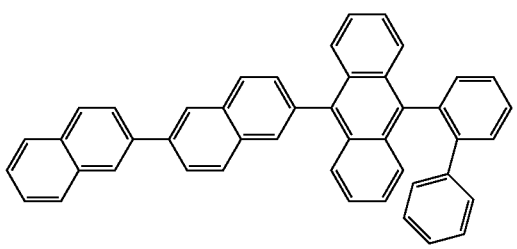
EM150
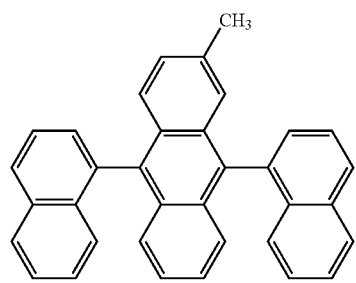
EM151
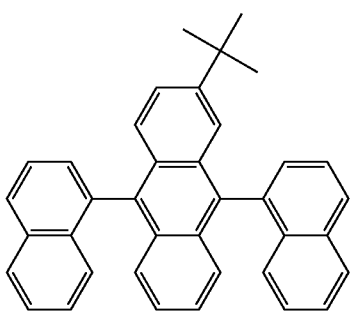

-continued
EM152
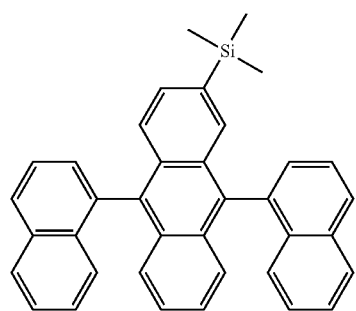
EM153
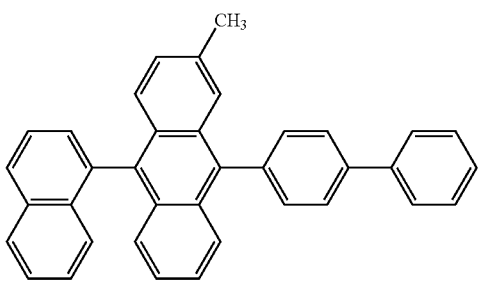
EM154
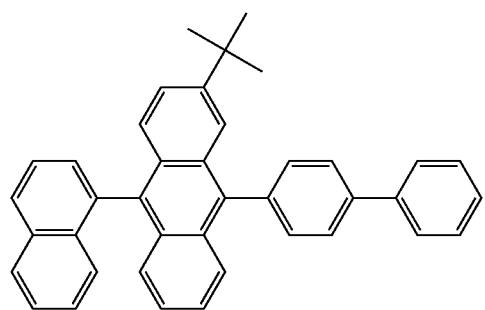
EM155
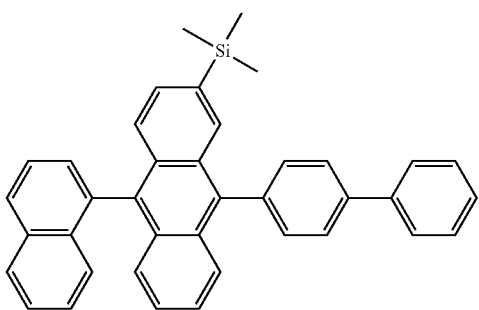
EM156
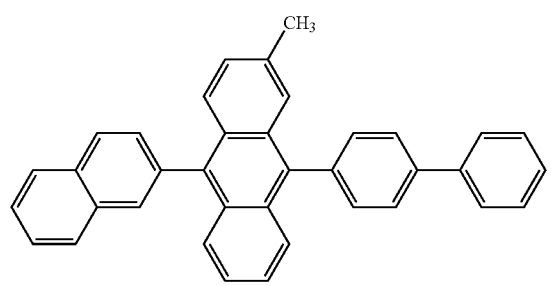
EM157
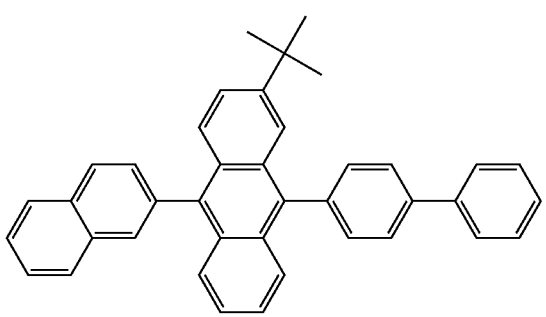
EM158
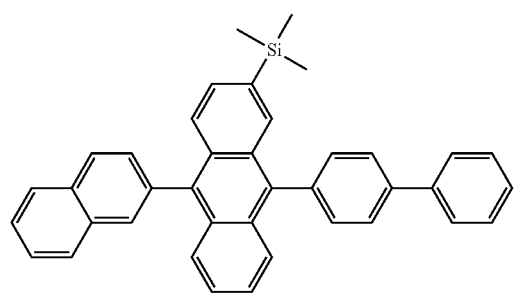
EM159
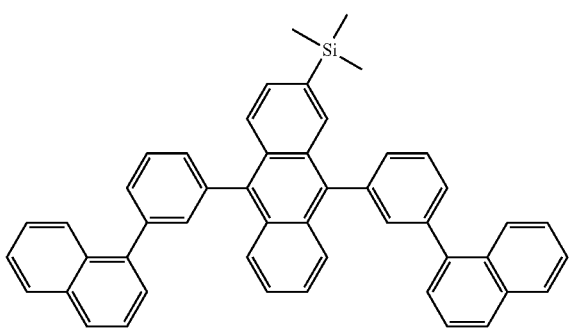
EM160
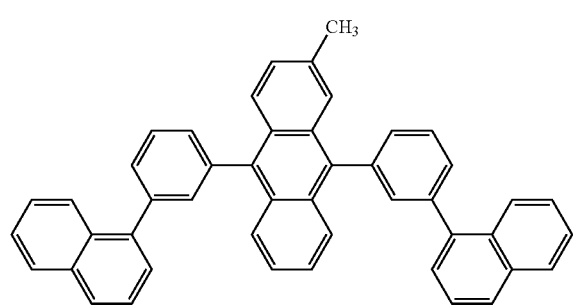
EM161
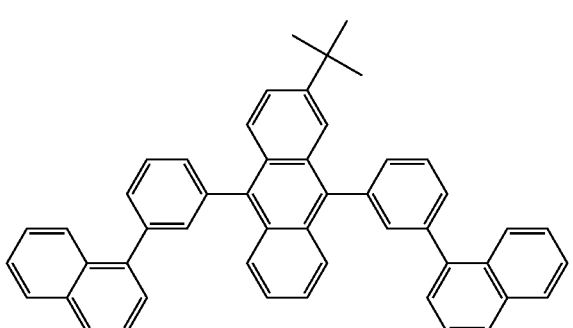

-continued
EM162
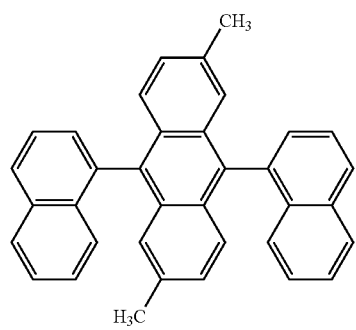
EM163
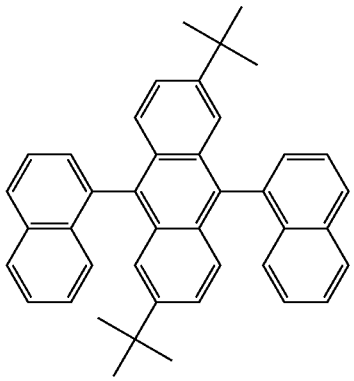
EM164
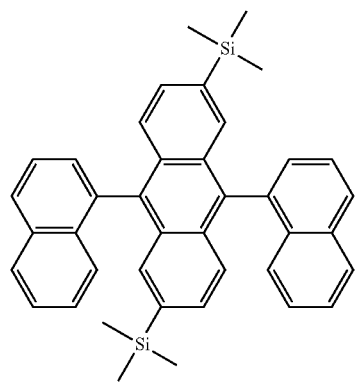
EM165
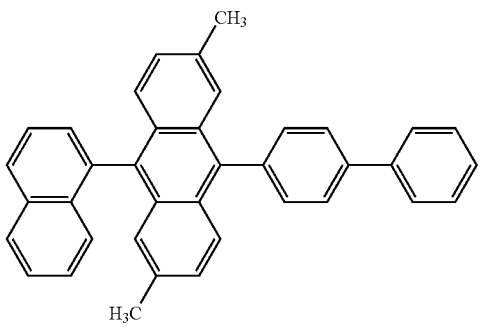
EM166
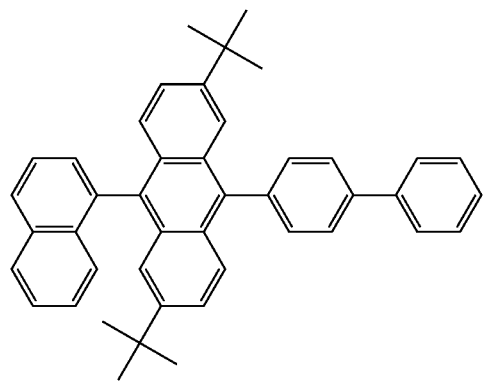
EM167
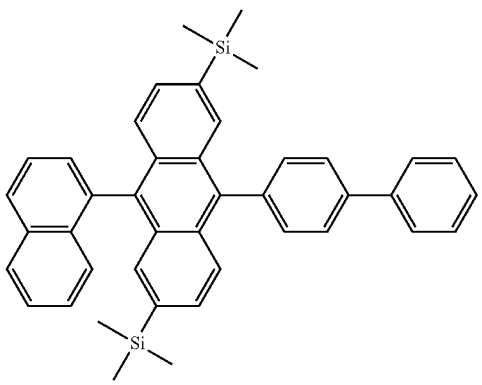
EM168
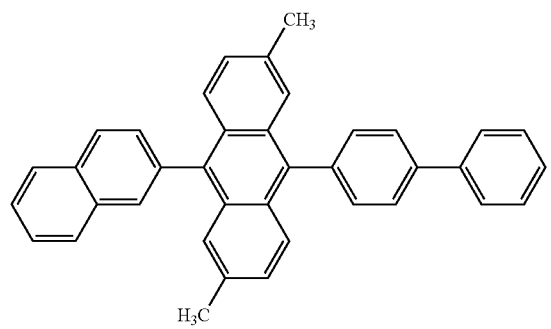
EM169
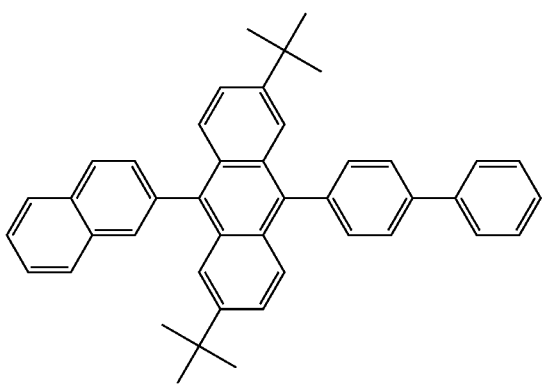

-continued
EM170
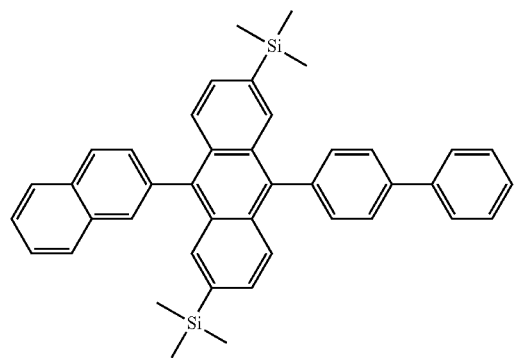
EM171
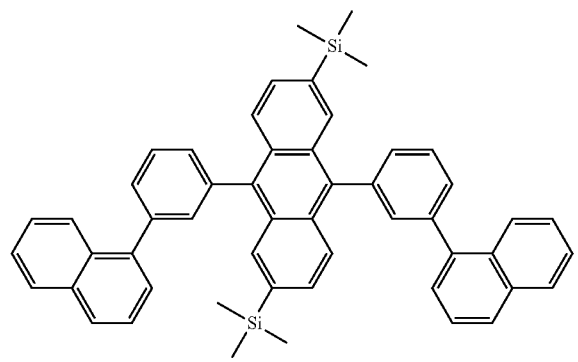
EM172
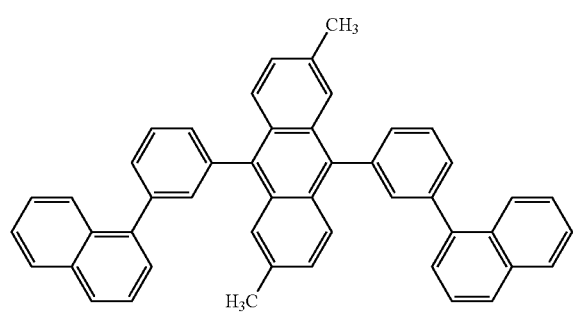
EM173
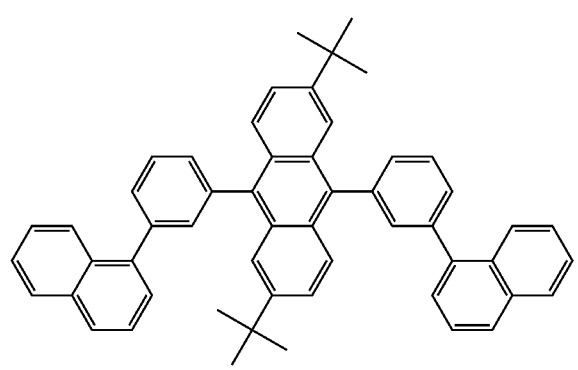
EM174
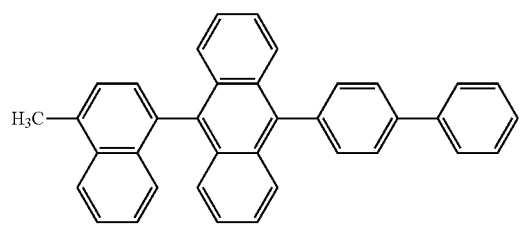
EM175
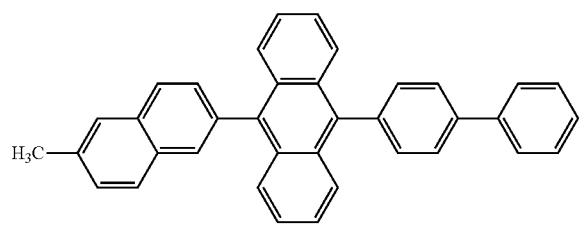
EM176
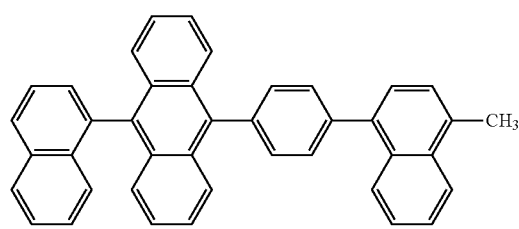
EM177
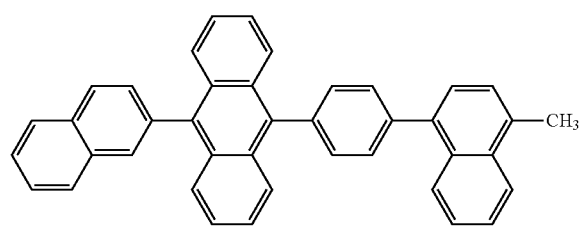
EM178
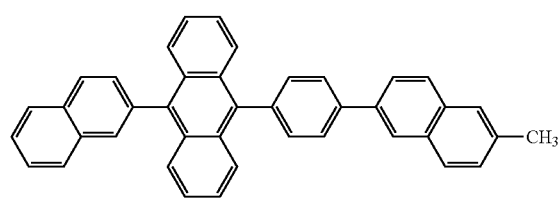
EM179
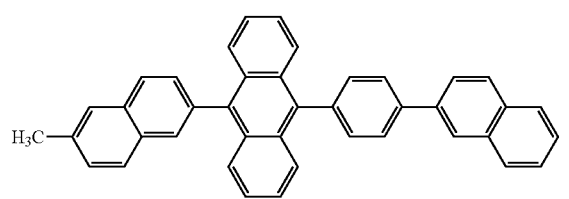

-continued
EM180
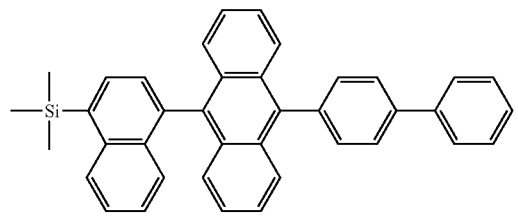
EM181
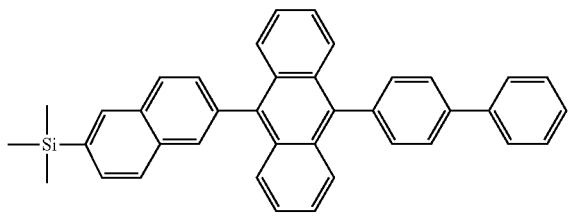
EM182
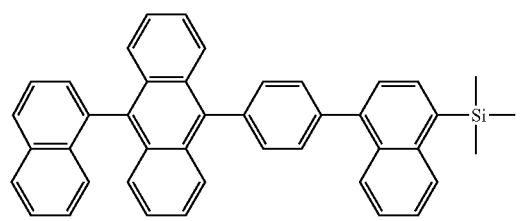
EM183
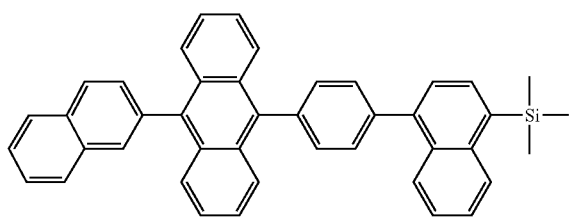
EM184
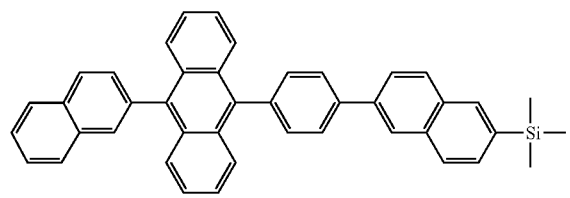
EM185
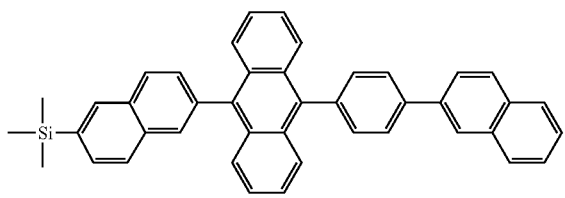
EM186
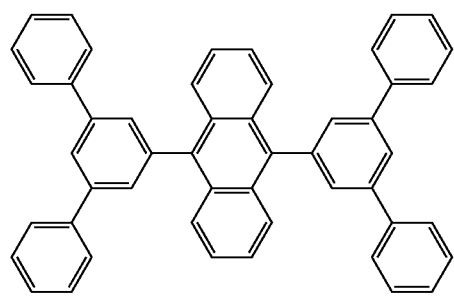
EM187
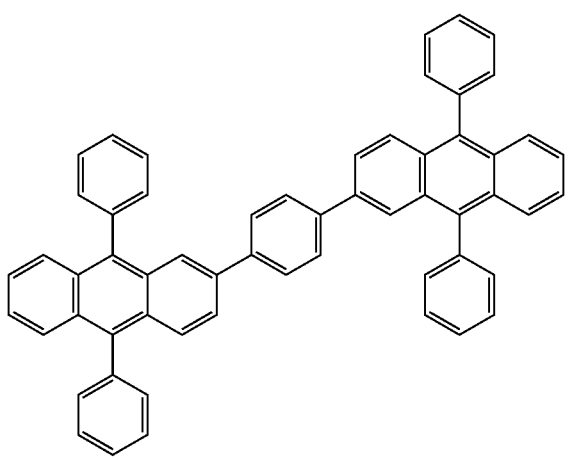
EM188
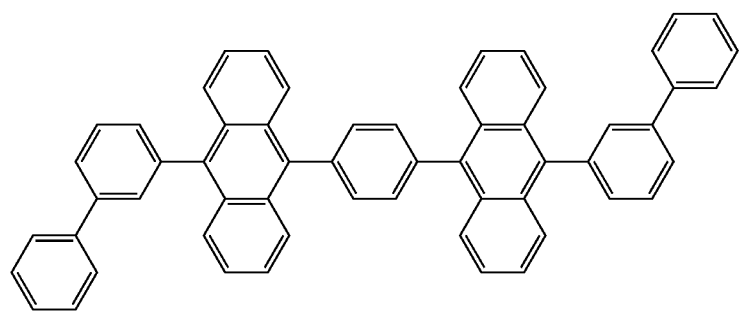

-continued
EM189
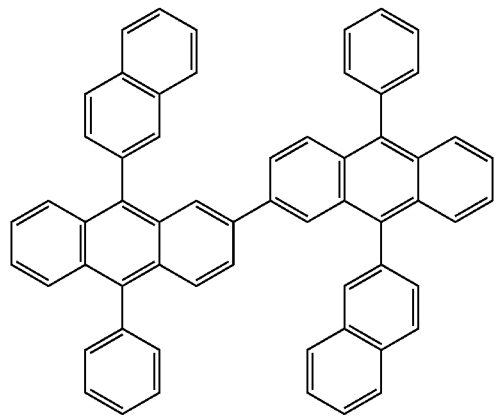
EM190
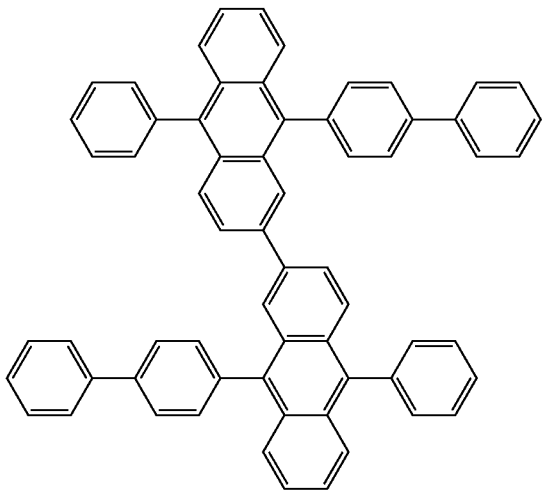
EM191
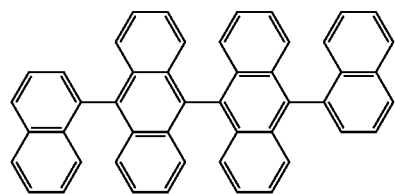
EM192
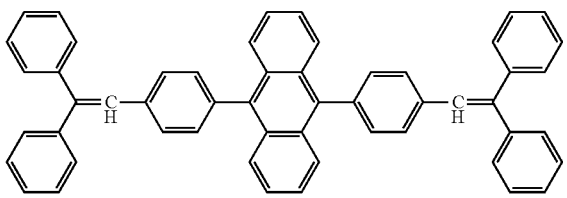
EM193
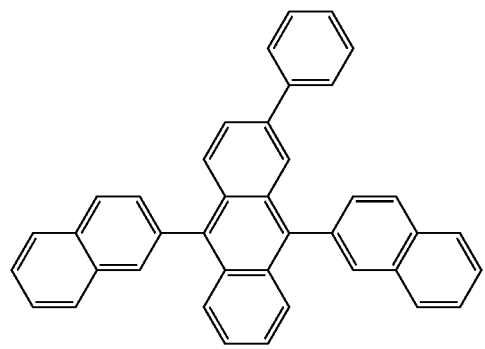
EM194
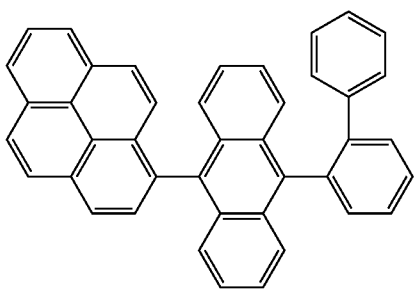
EM195
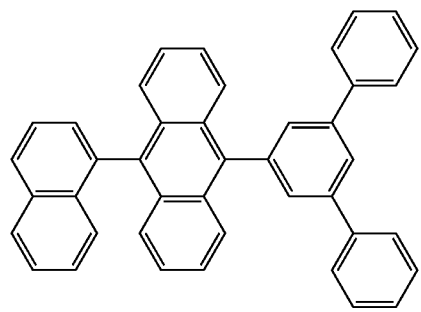
EM196
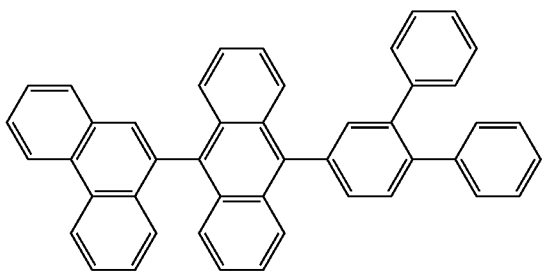

-continued
EM197
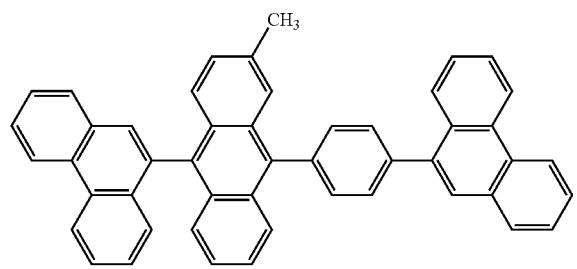
EM198
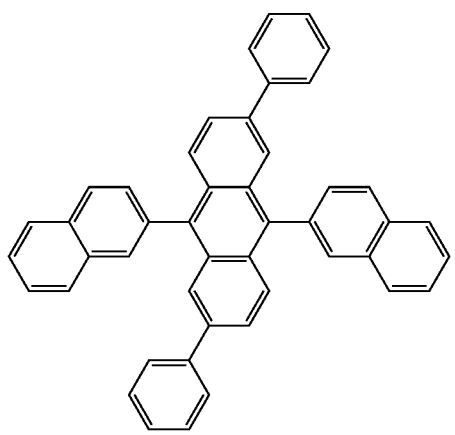
EM199
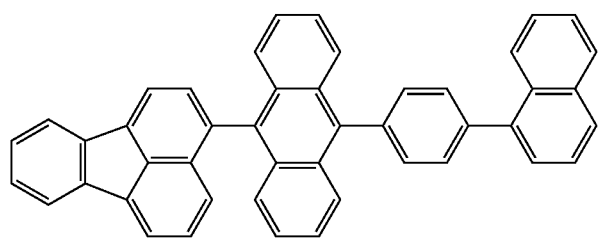
EM200
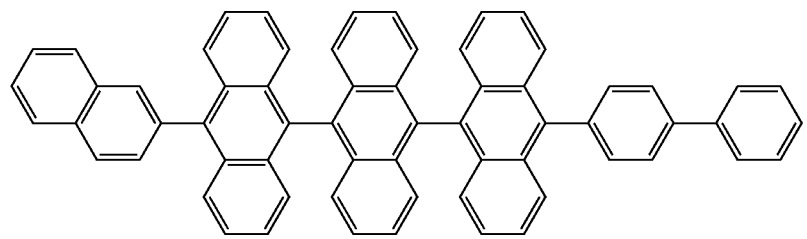
EM201
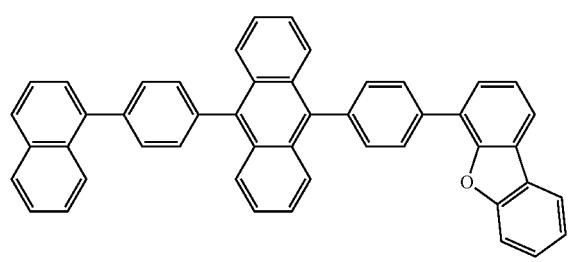
EM202
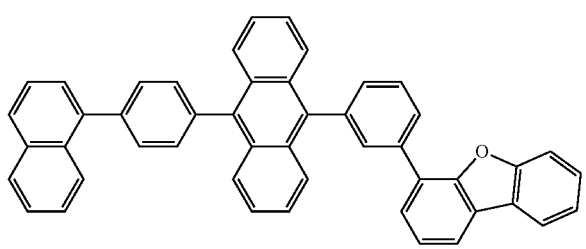
EM203
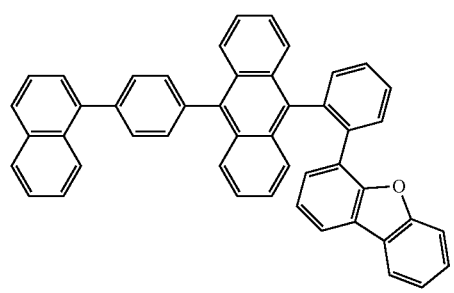
EM204
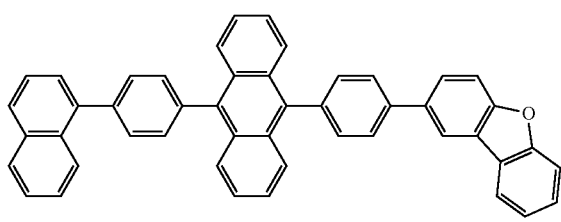

-continued
EM205
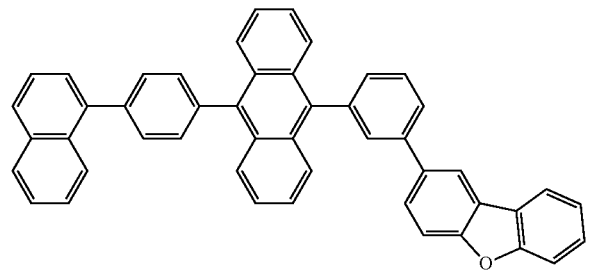
EM206
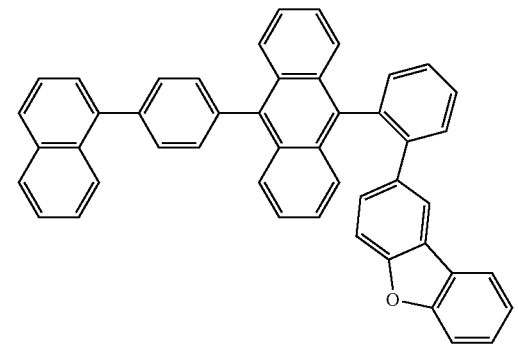
EM207
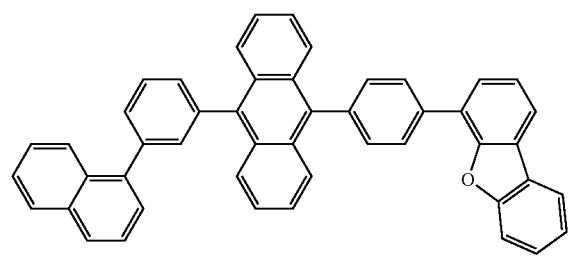
EM208
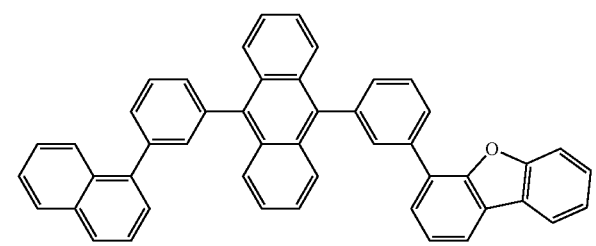
EM209
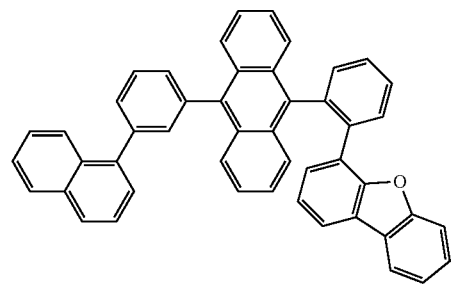
EM210
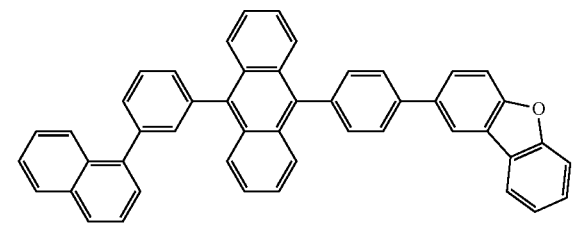
EM211
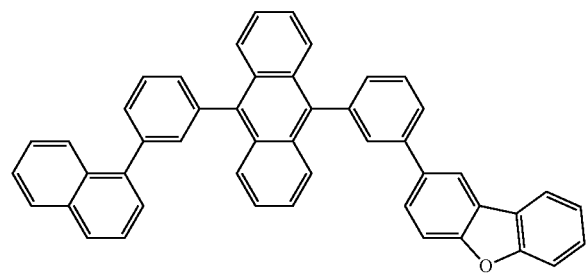
EM212
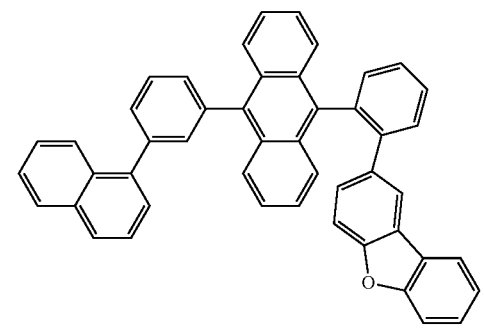
EM213
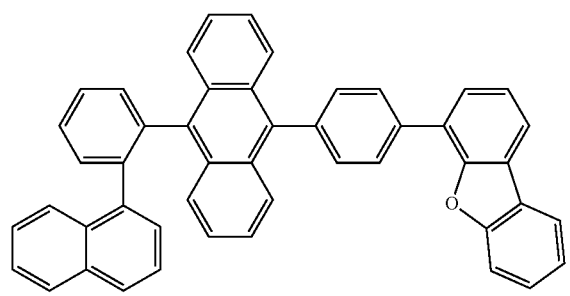
EM214
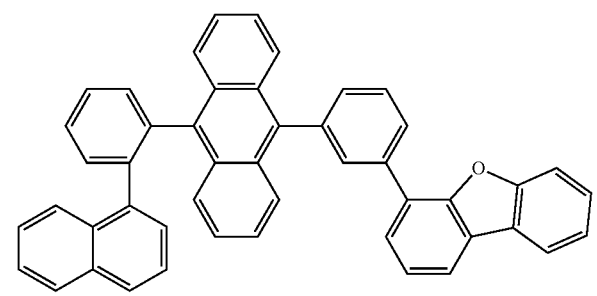

-continued
EM215
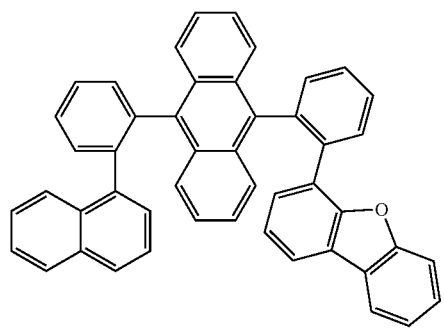
EM216
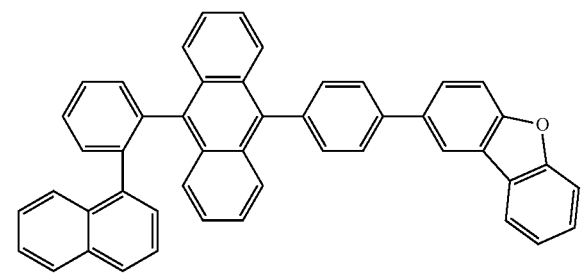
EM217
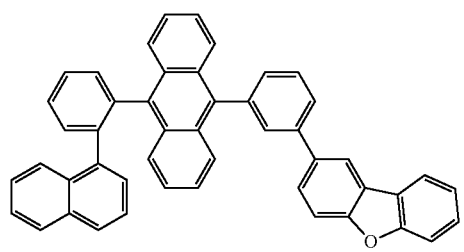
EM218
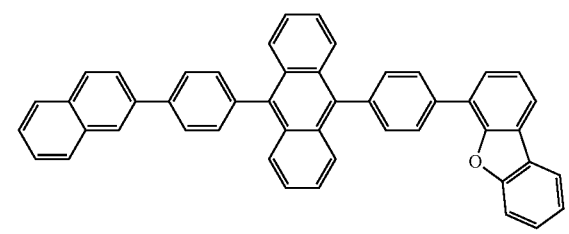
EM219
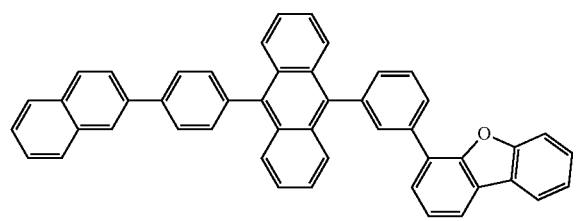
EM220
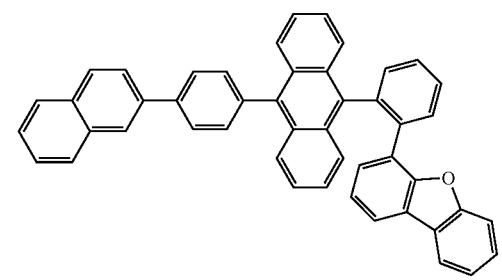
EM221
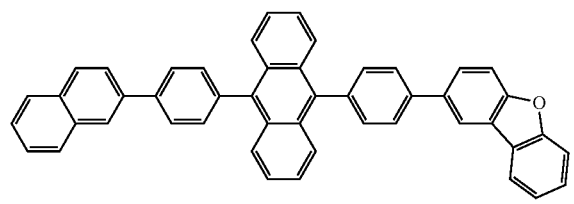
EM222
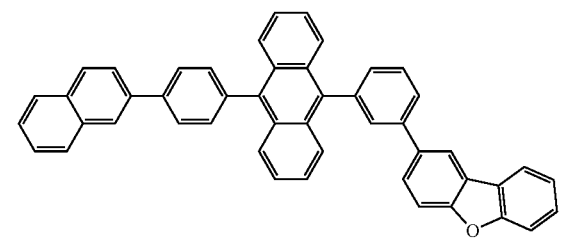
EM223
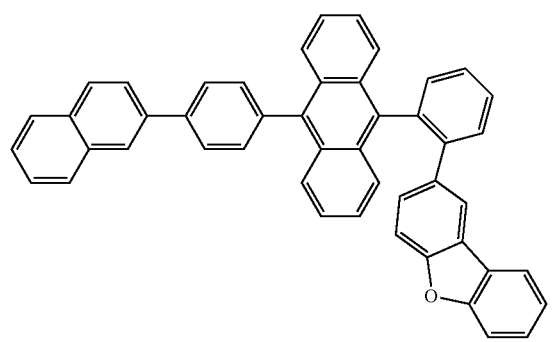
EM224
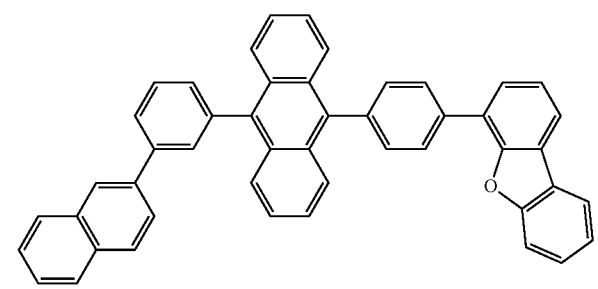

-continued
EM225
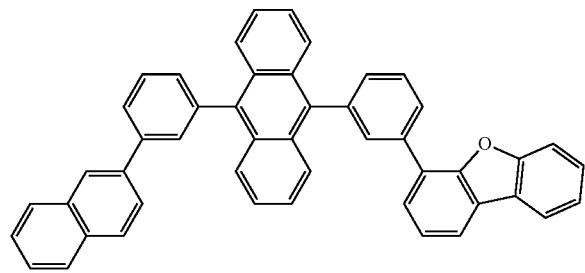
EM226
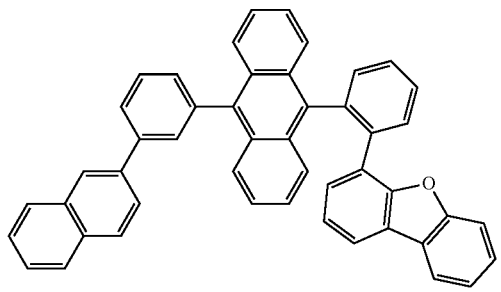
EM227
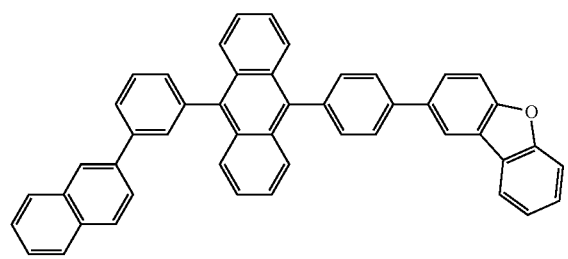
EM228
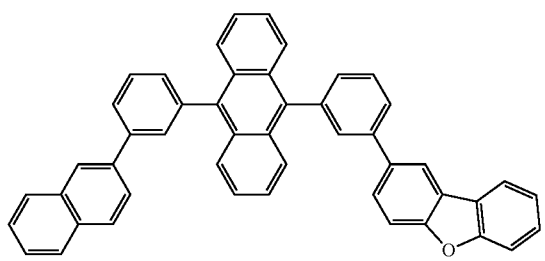
EM229
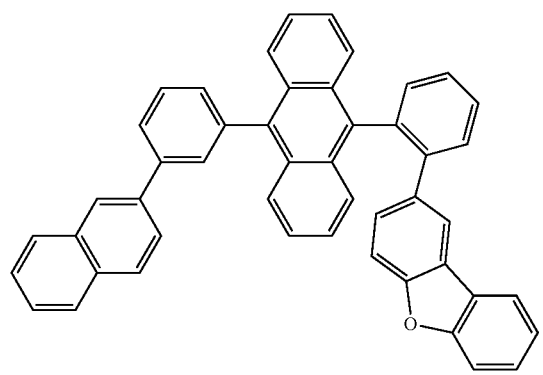
EM230
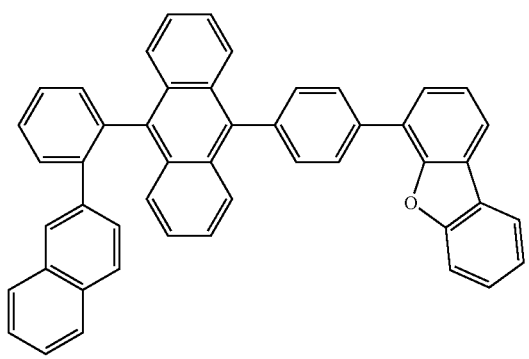
EM231
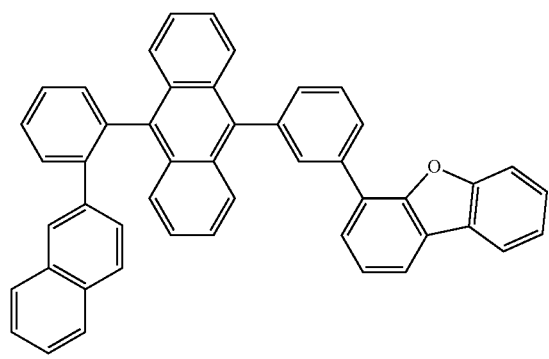
EM232
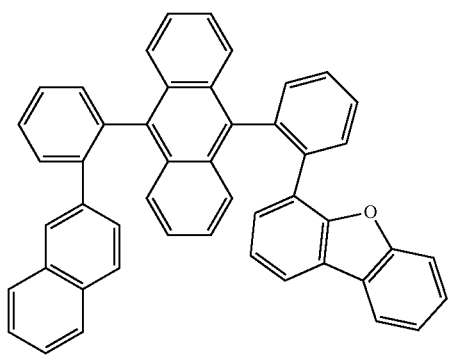

-continued
EM233
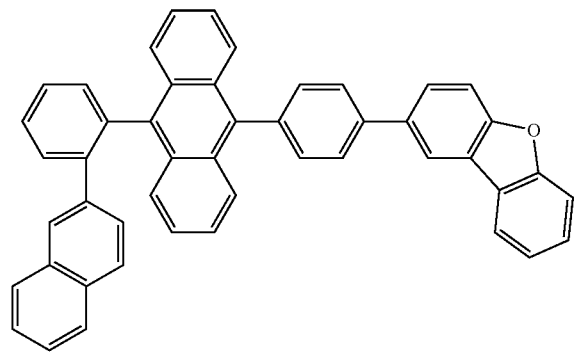
EM234
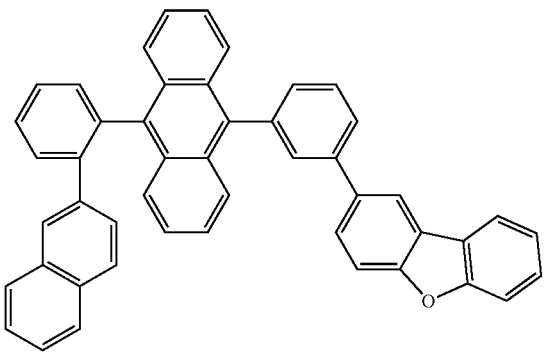
EM235
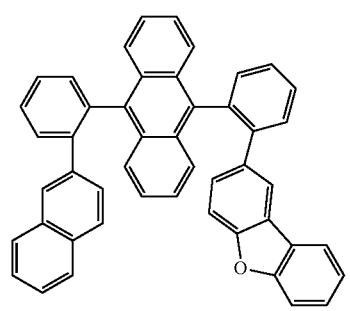
EM236
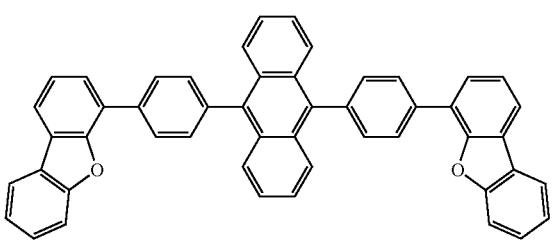
EM237
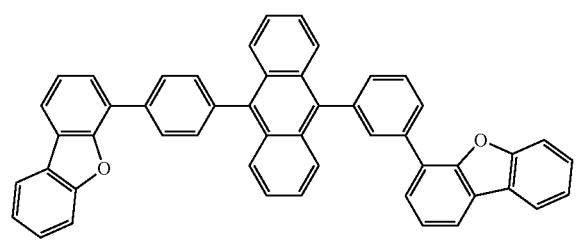
EM238
EM239
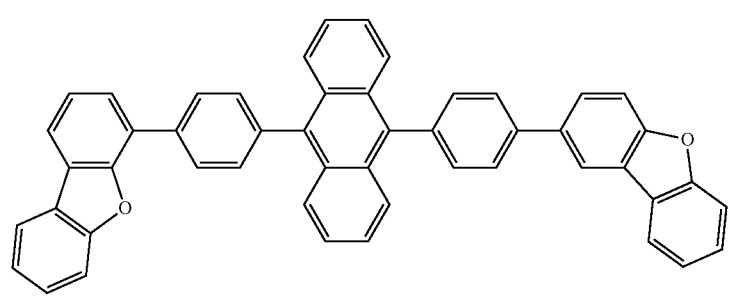
EM240
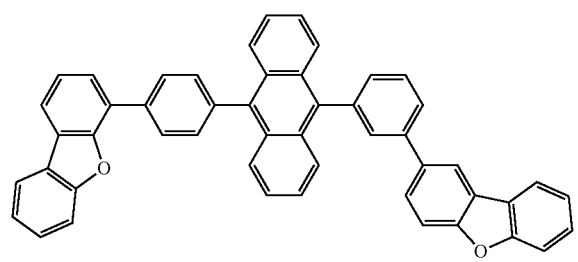
EM241
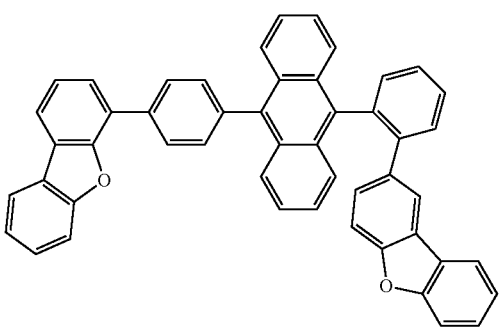

EM242
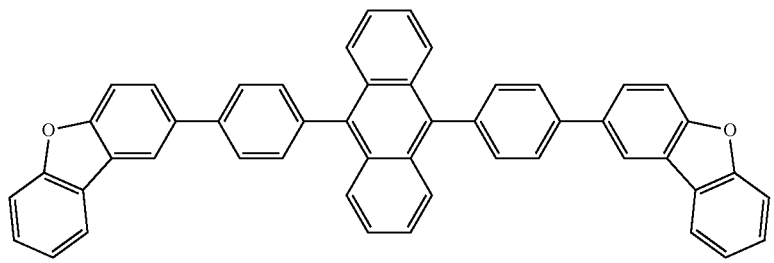
EM243
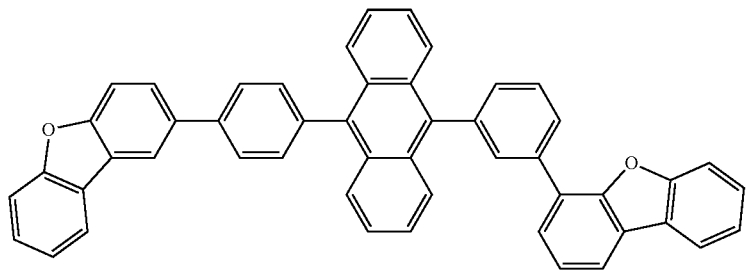
EM244
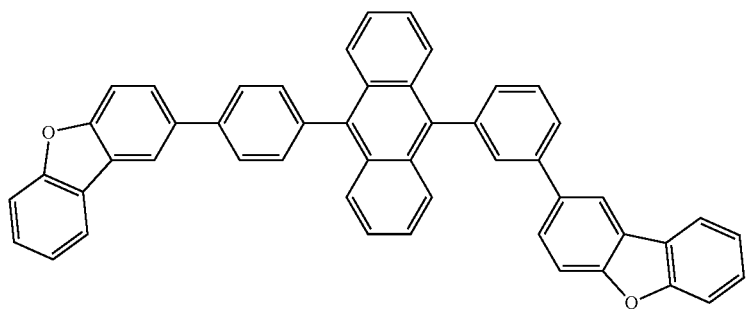
EM245
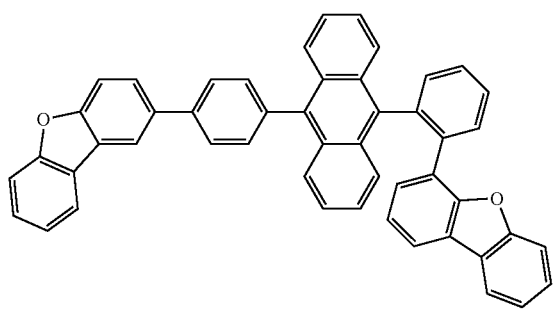
EM246
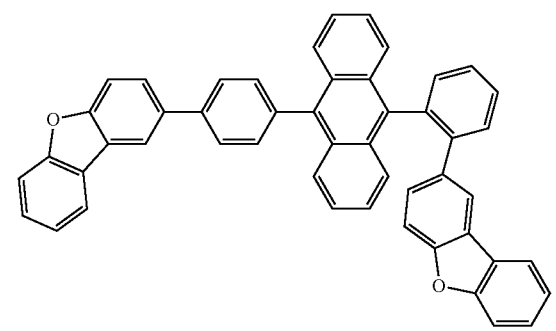
EM247
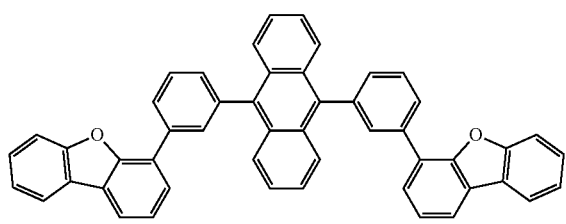
EM248
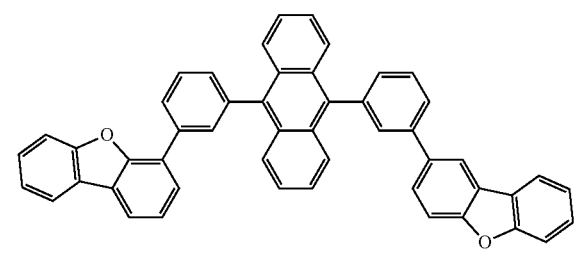

-continued
EM249
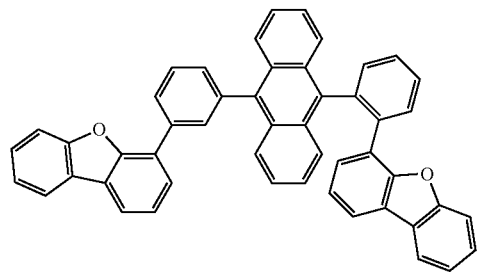
EM250
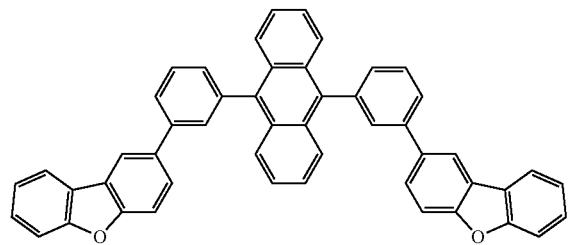
EM251
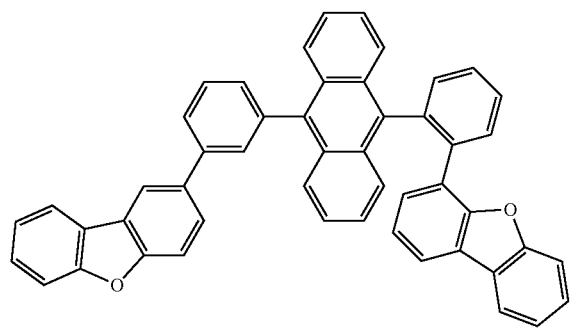
EM252
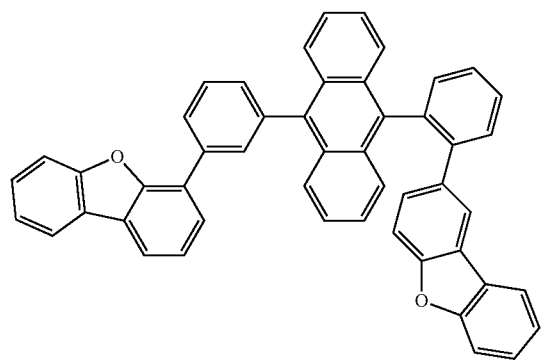
EM253
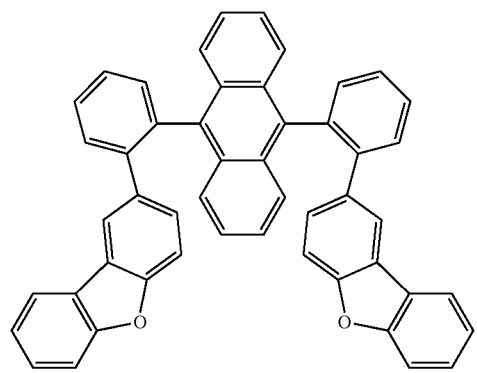
EM254
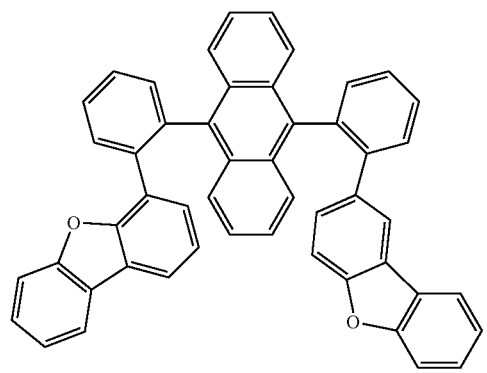
EM255
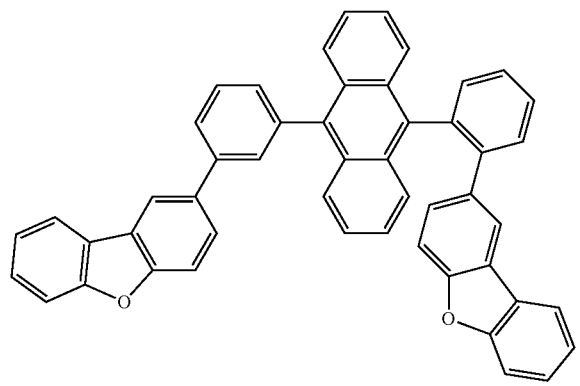
EM256
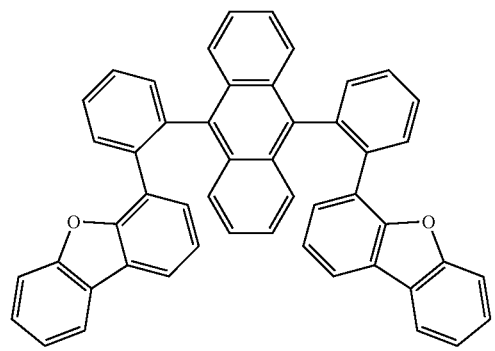

-continued
EM257
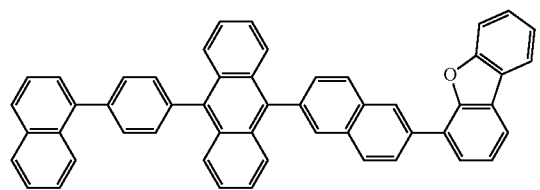
EM258
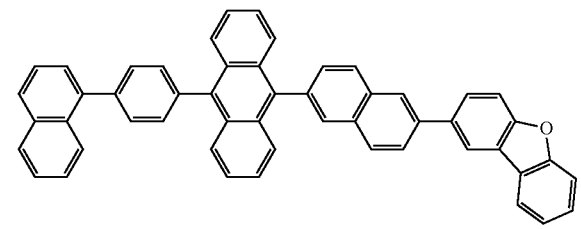
EM259
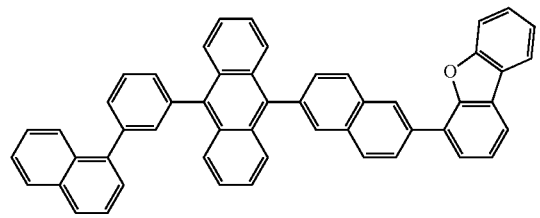
EM260
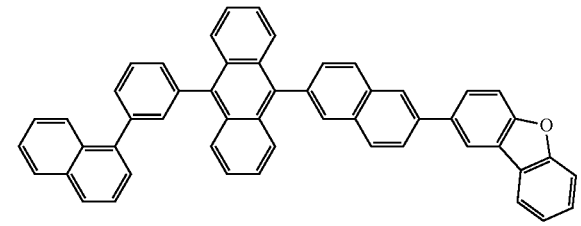
EM261
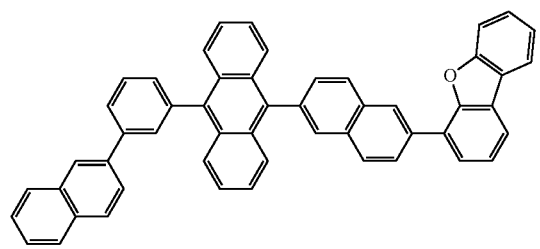
EM262
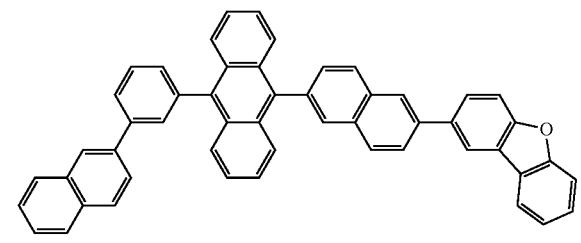
EM263
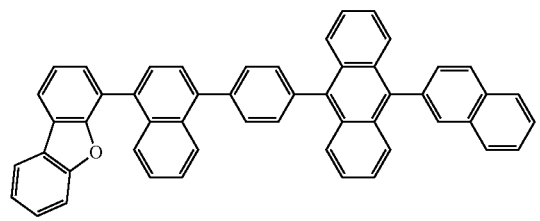
EM264
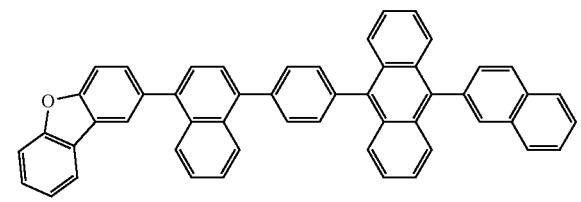
EM265
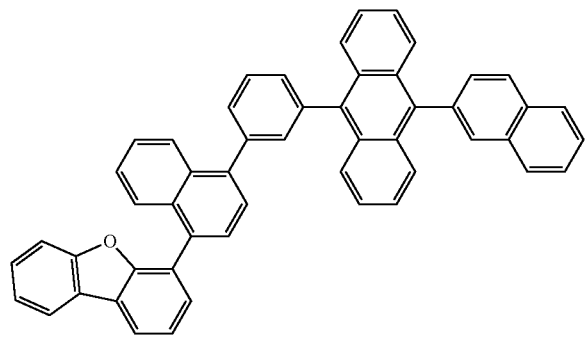
EM266
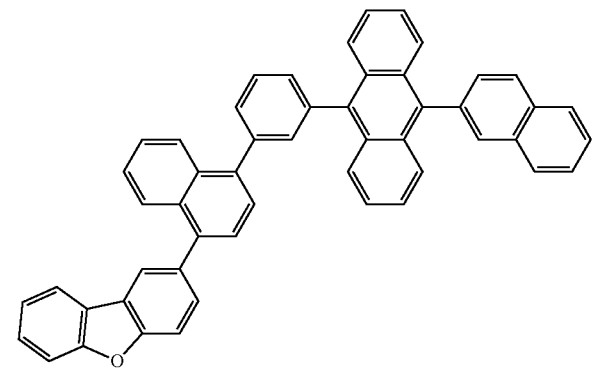

EM267
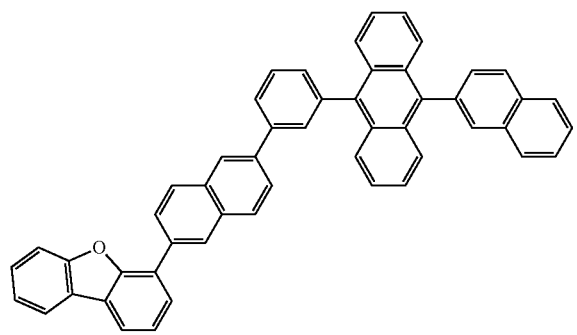
EM268
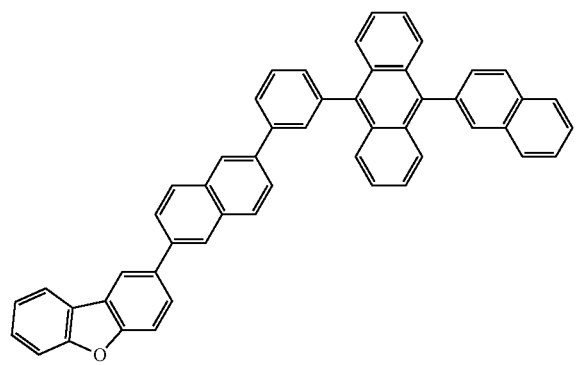
EM269
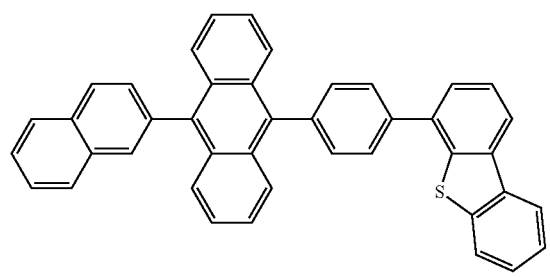
EM270
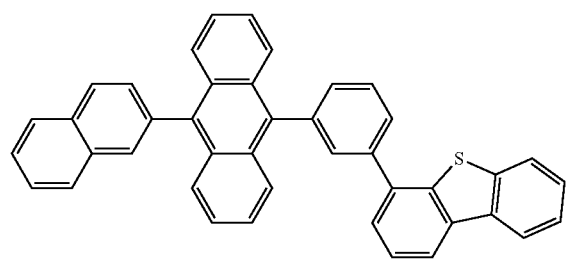
EM271
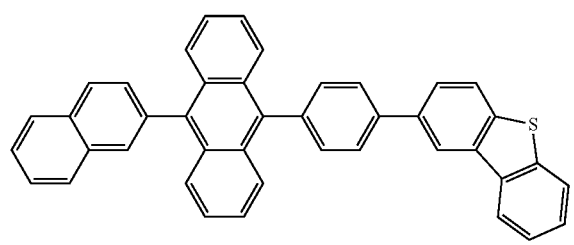
EM272
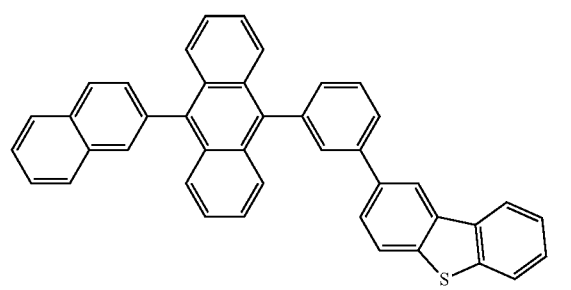
EM273
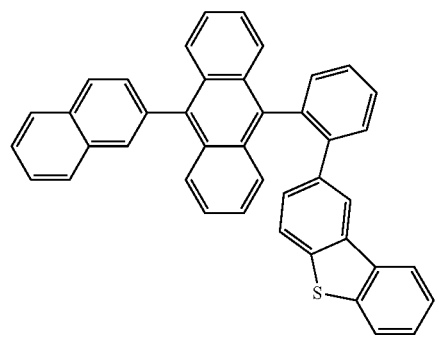
EM274
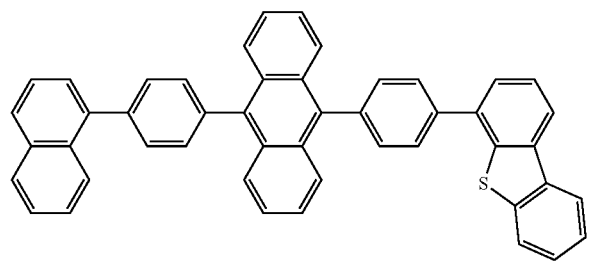
EM275
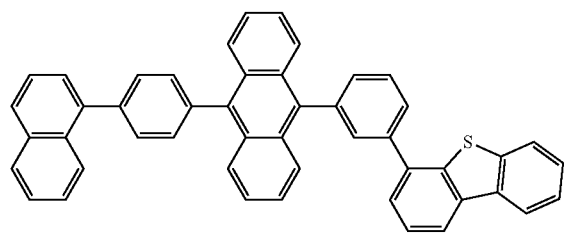
EM276
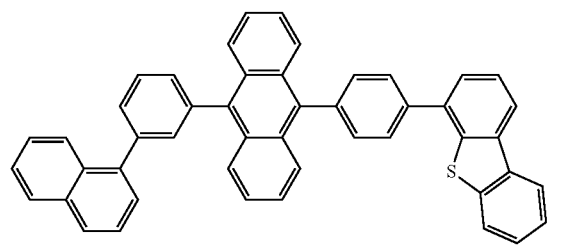

-continued
EM277
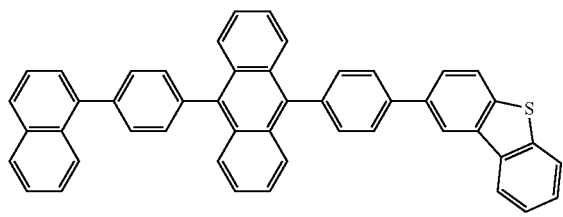
EM278
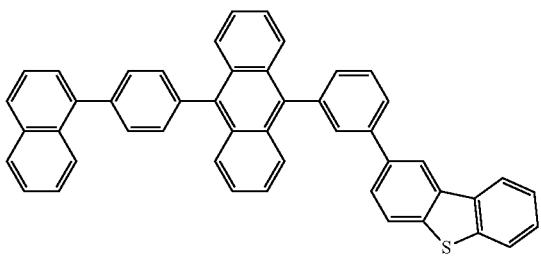
EM279
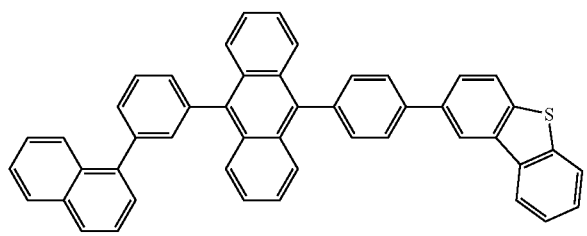
EM280
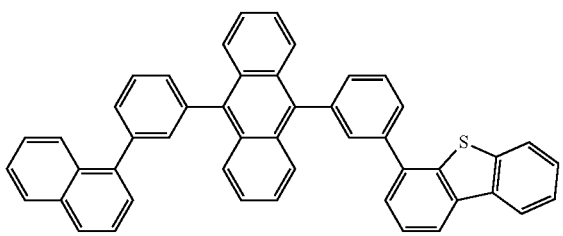
EM281
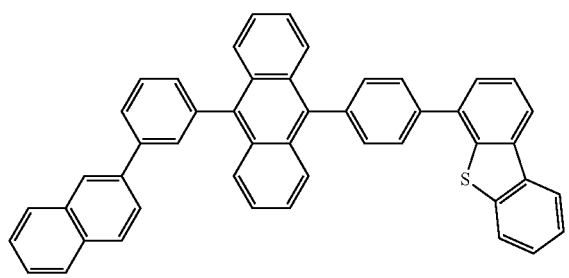
EM282
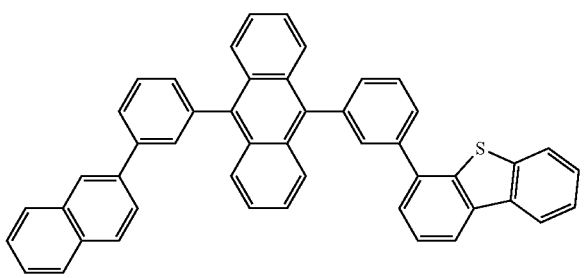
EM283
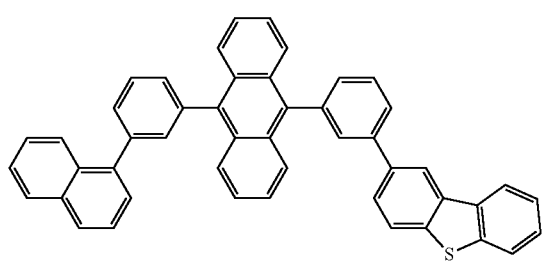
EM284
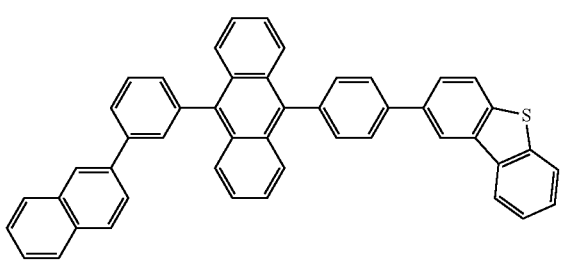
EM285
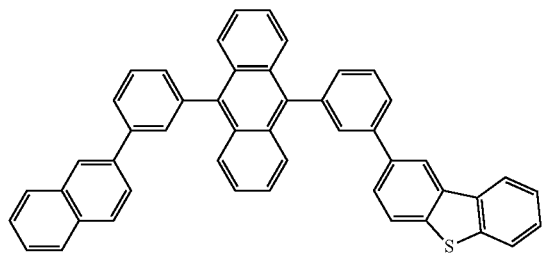
EM286
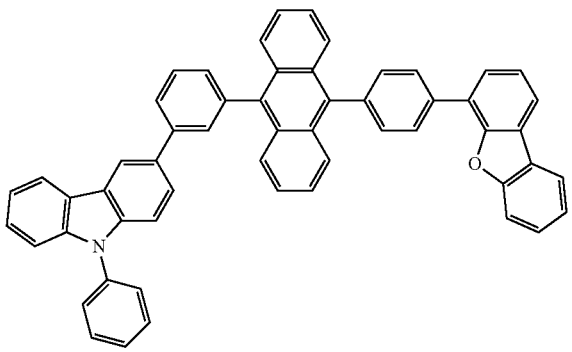

-continued
EM287
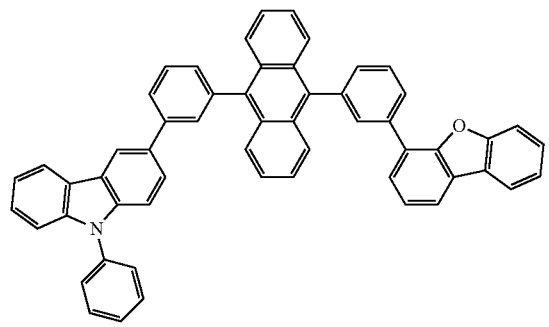
EM288
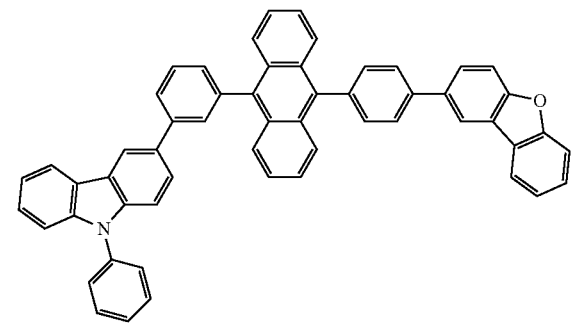
EM289
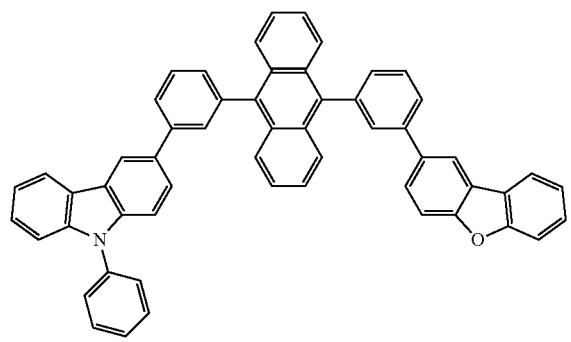
EM290
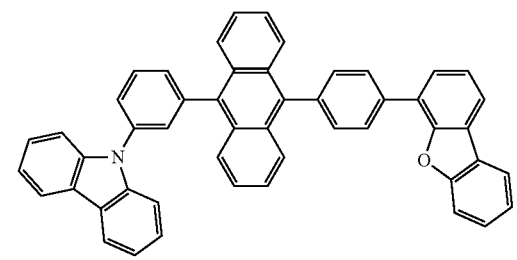
EM291
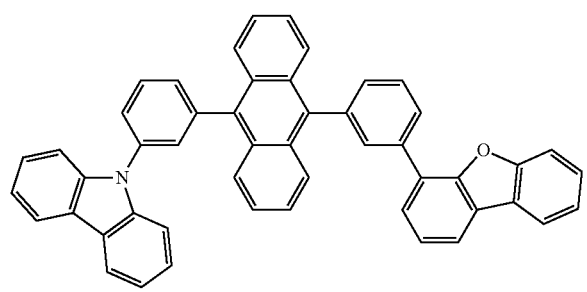
EM292
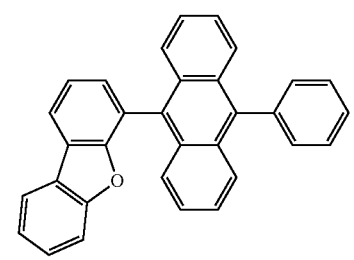
EM293
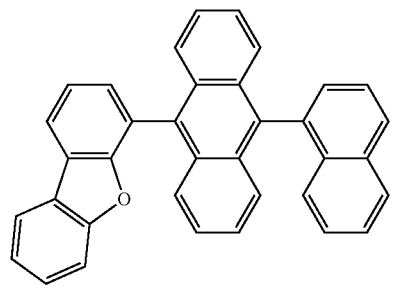
EM294
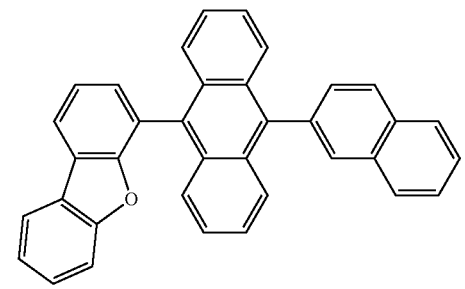
EM295
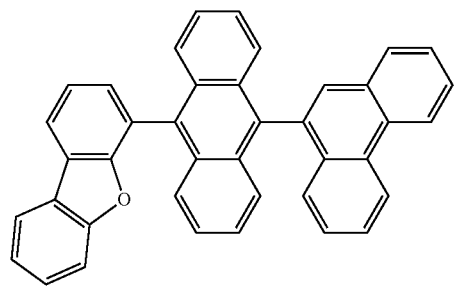
EM296
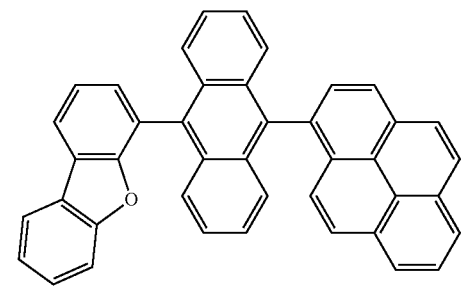

-continued
EM297
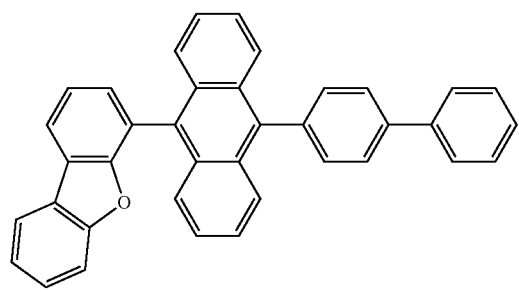
EM298
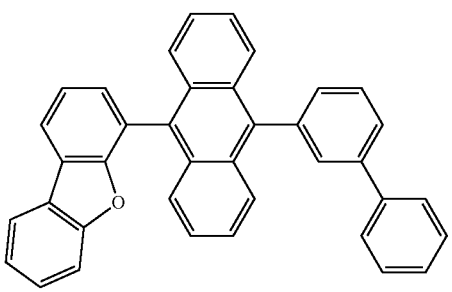
EM299
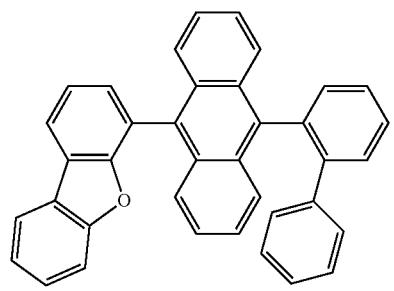
EM300
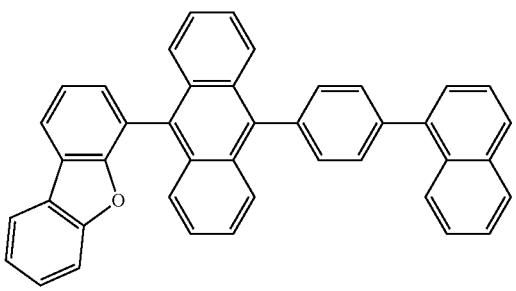
EM301
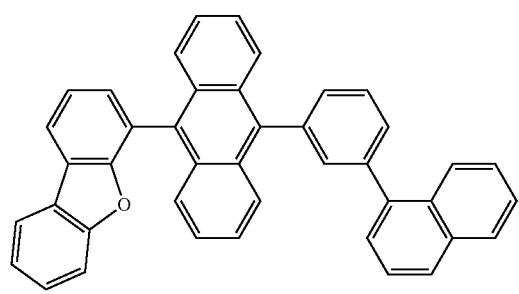
EM302
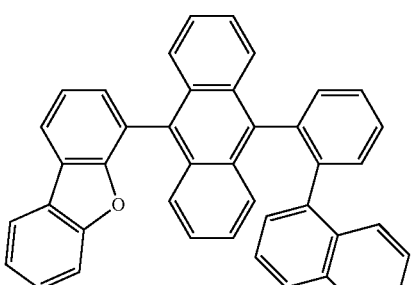
EM303
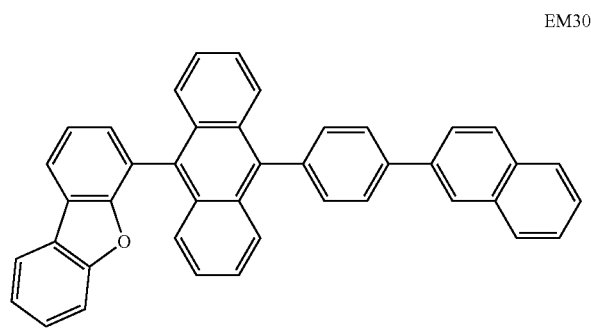
EM304
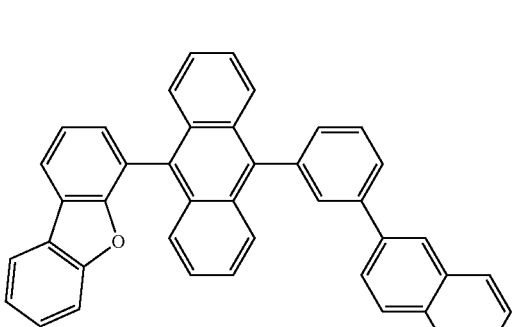
EM305
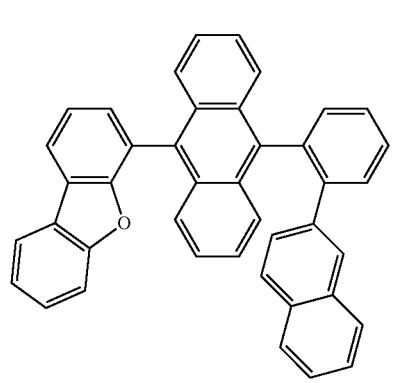
EM306
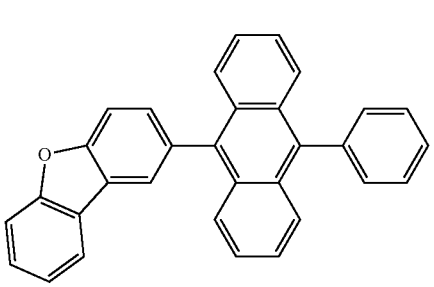

-continued
EM307
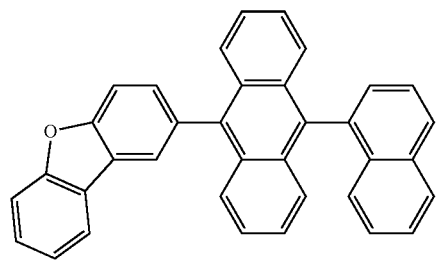
EM308
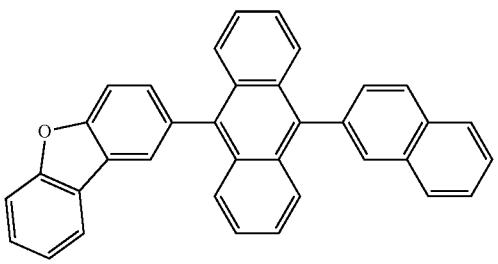
EM309
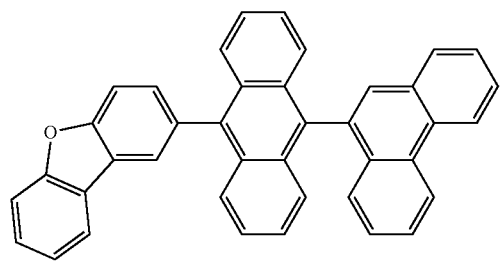
EM310
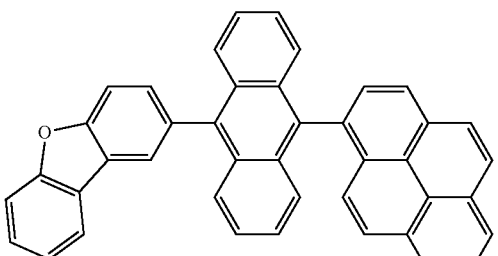
EM311
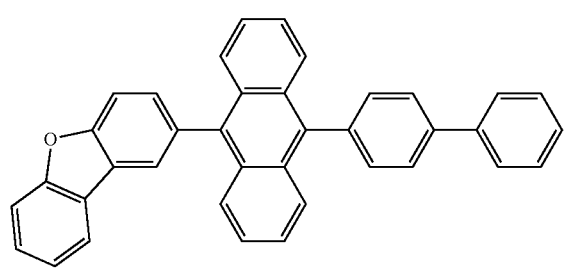
EM312
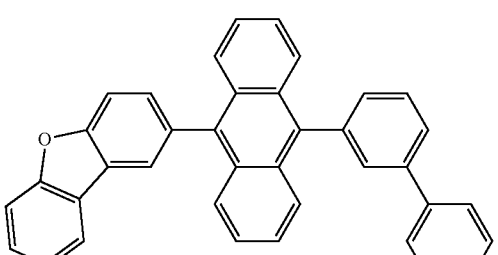
EM313
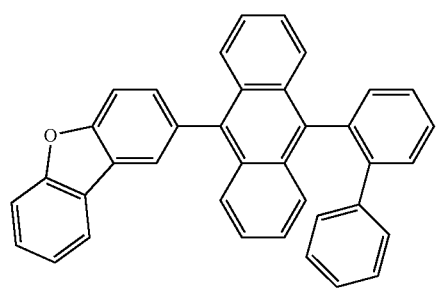
EM314
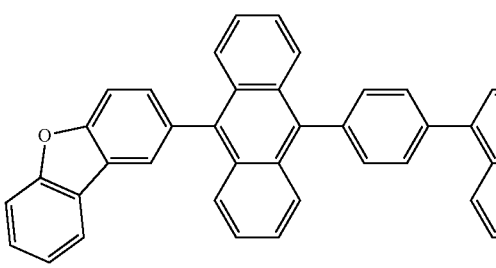
EM315
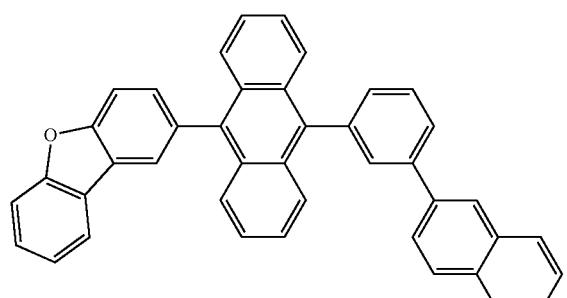
EM316
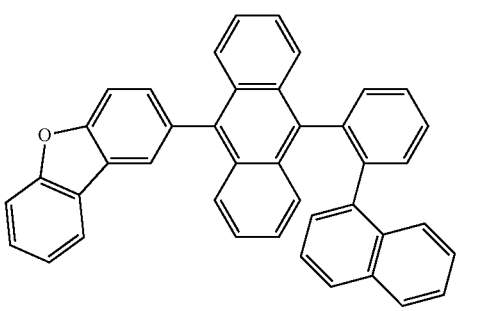

-continued
EM317
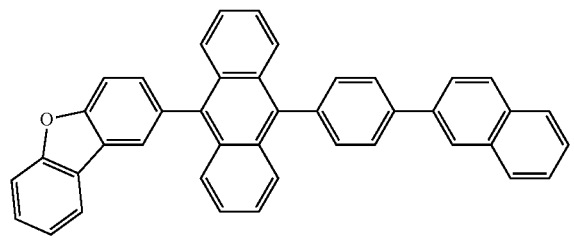
EM318
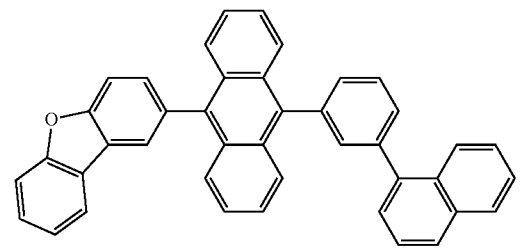
EM319
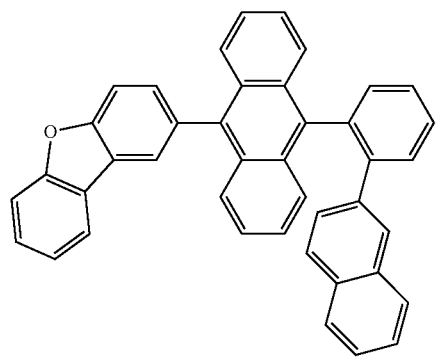
EM320
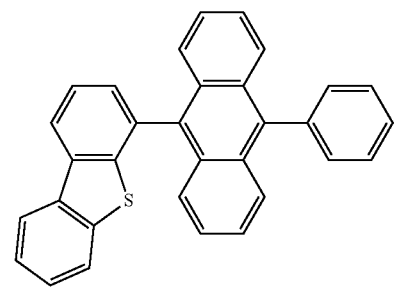
EM321
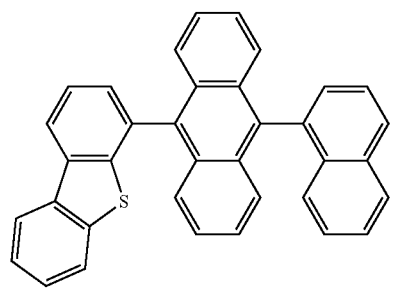
EM322
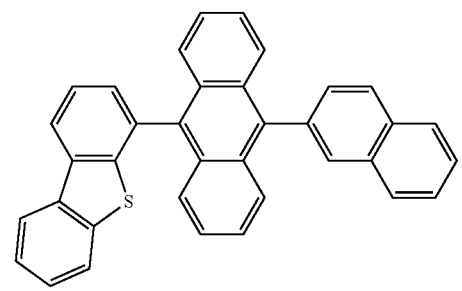
EM323
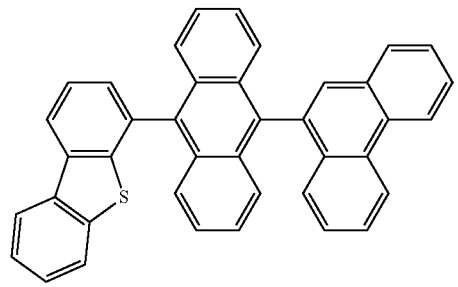
EM324
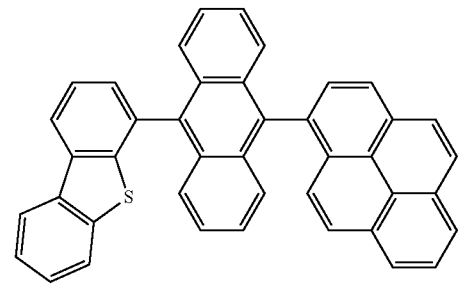
EM325
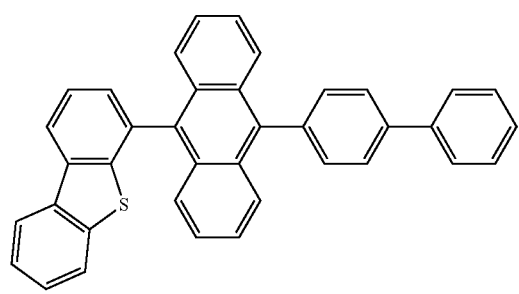
EM326
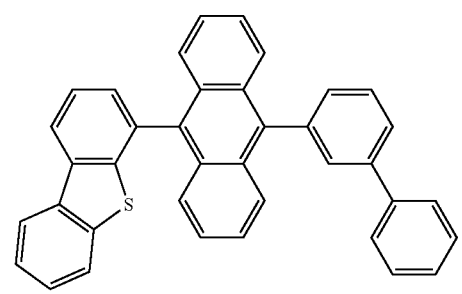

-continued
EM327
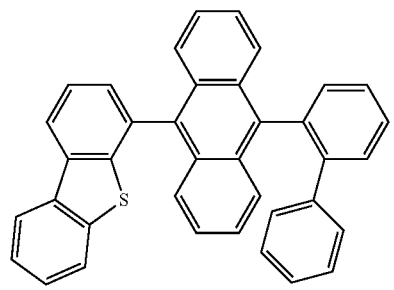
EM328
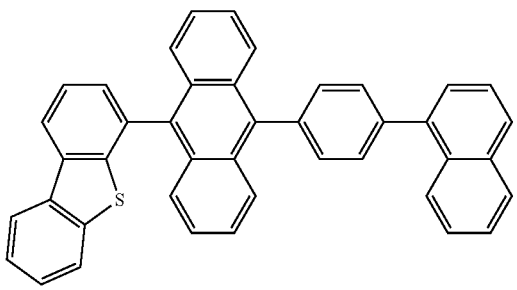
EM329
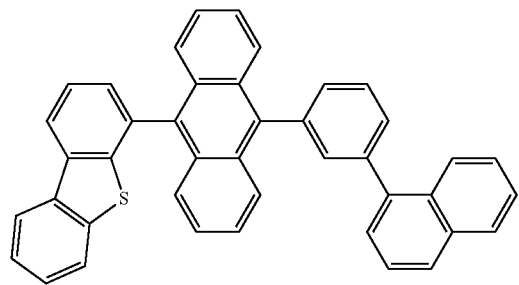
EM330
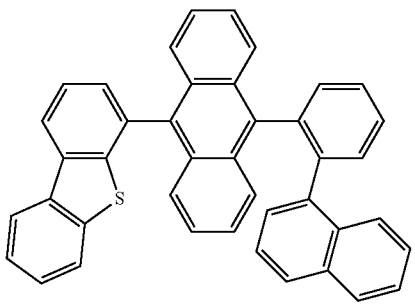
EM331
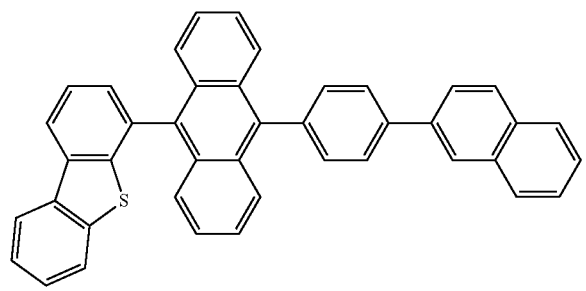
EM332
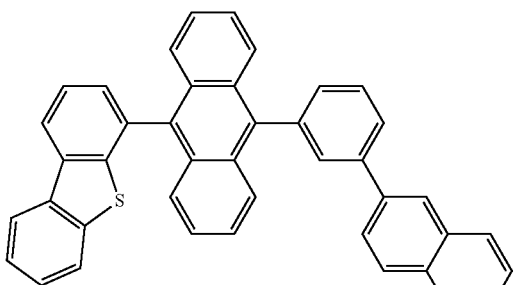
EM333
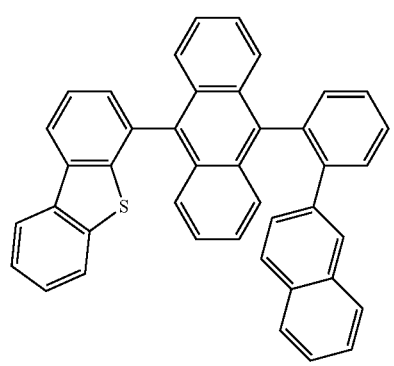
EM334
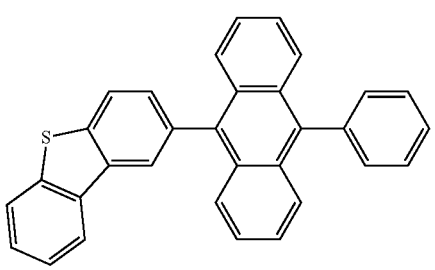
EM335
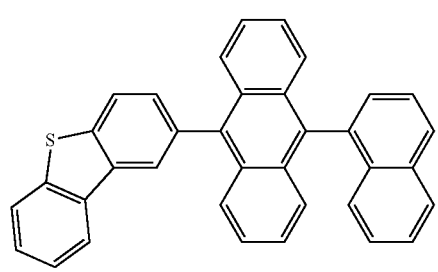
EM336
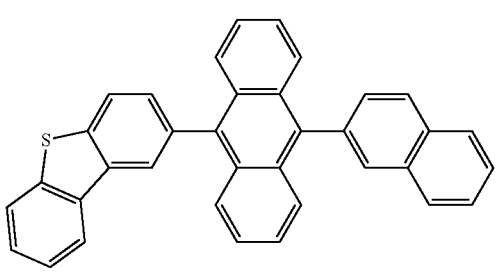

-continued
EM337
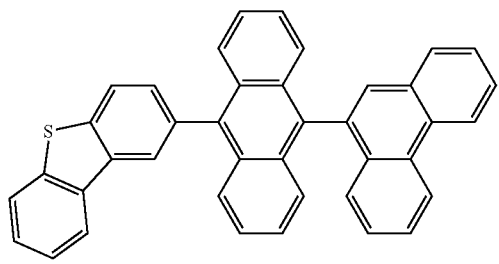
EM339
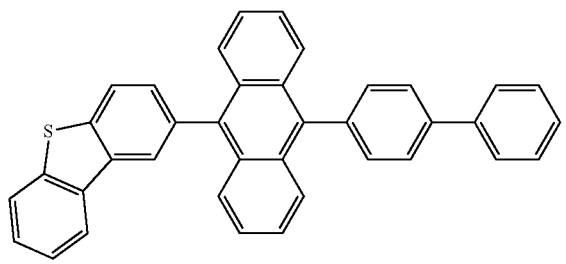
EM341
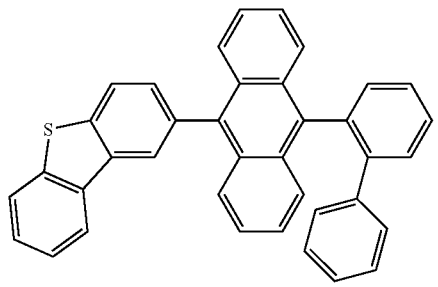
EM343
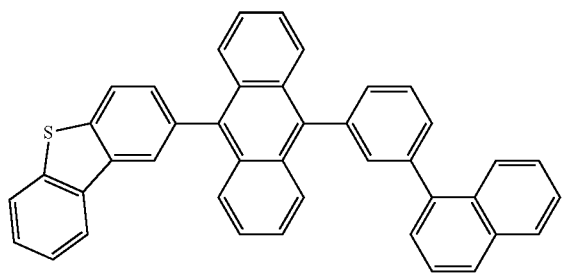
EM345
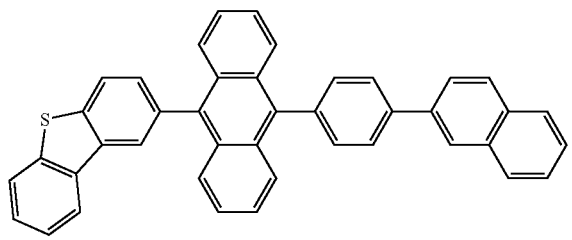
EM338
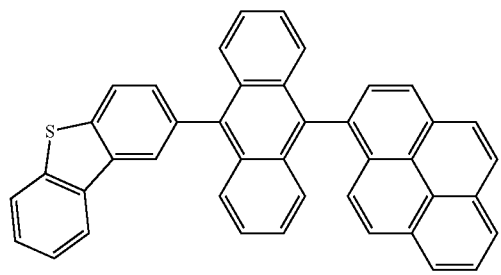
EM340
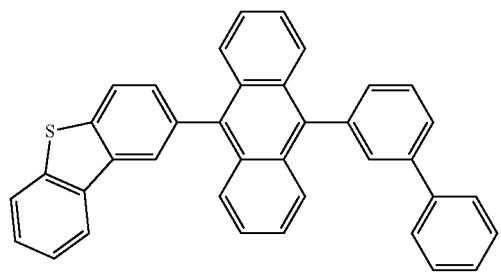
EM342
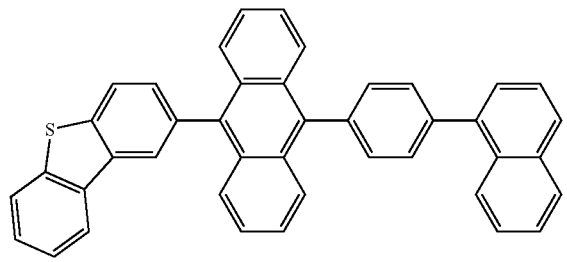
EM344
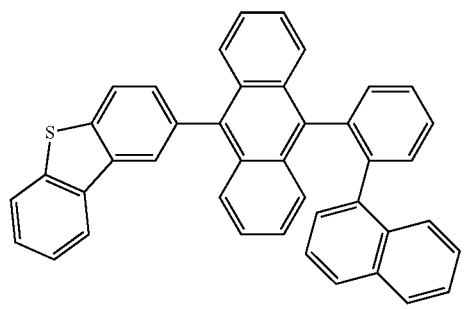
EM346
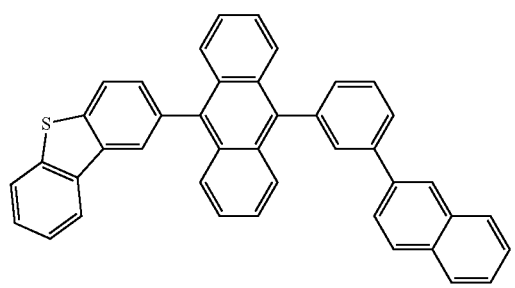

-continued
EM347
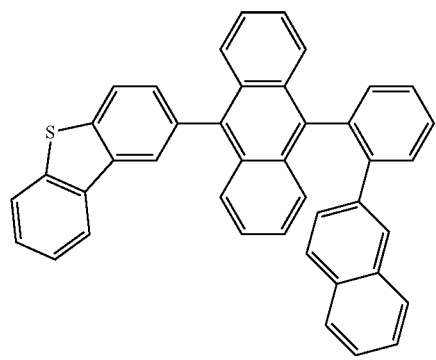
EM348
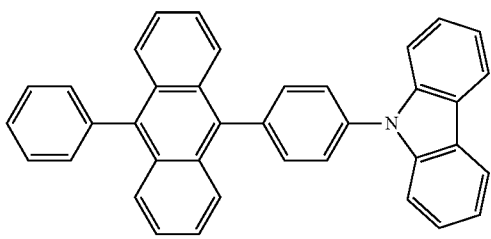
EM349
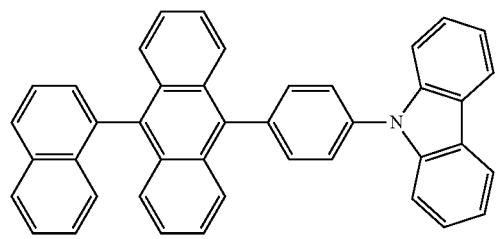
EM350
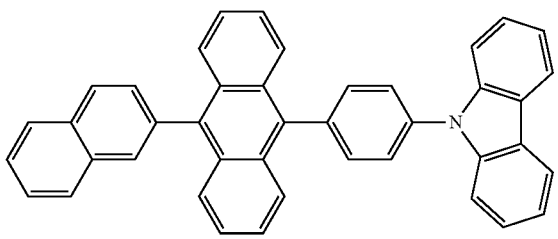
EM351
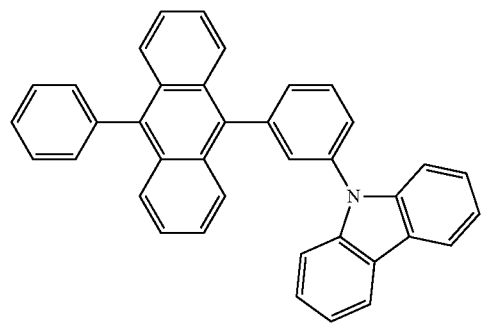
EM352
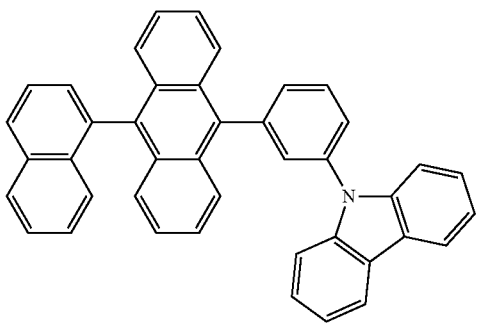
EM353
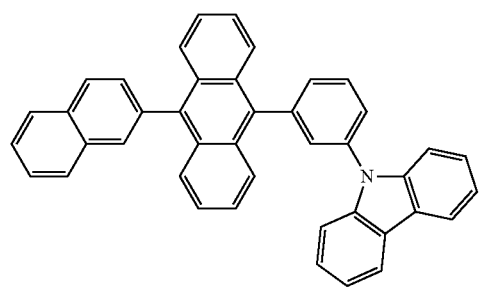
EM354
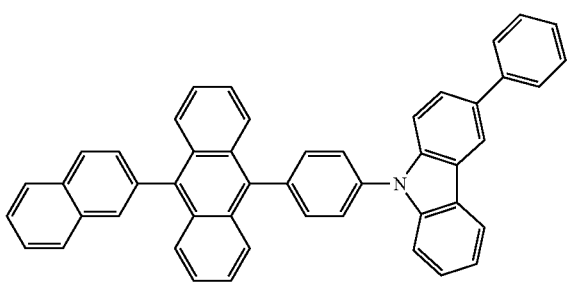
EM355
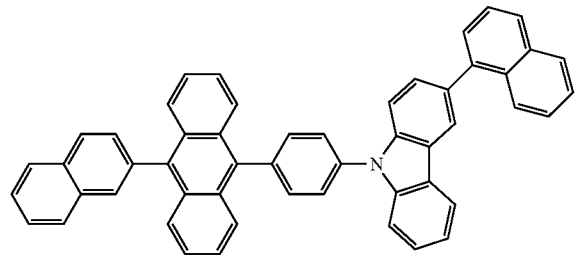
EM356
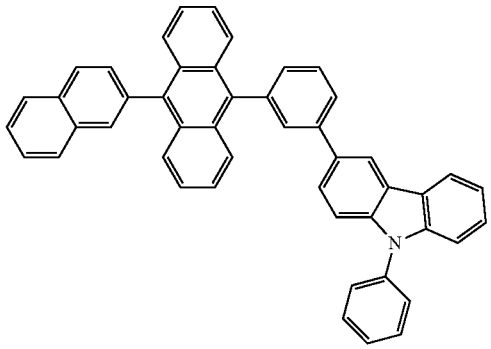

-continued
EM357
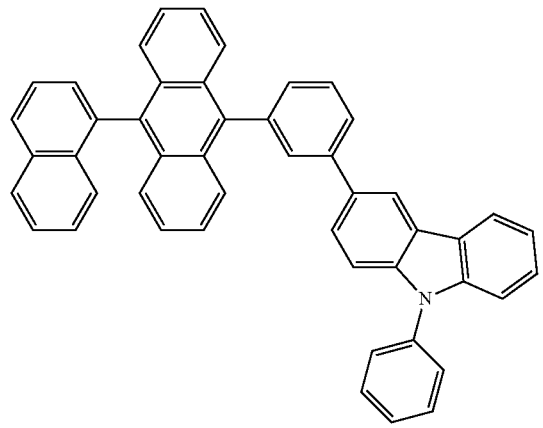
EM358
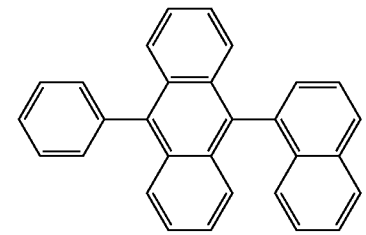
EM359
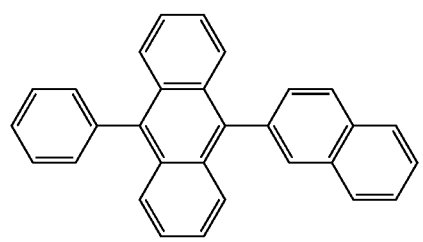
EM360
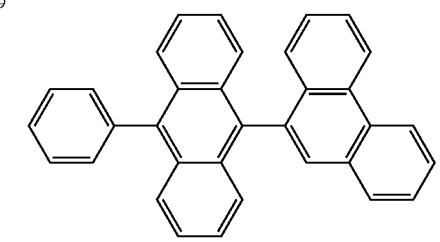
EM361
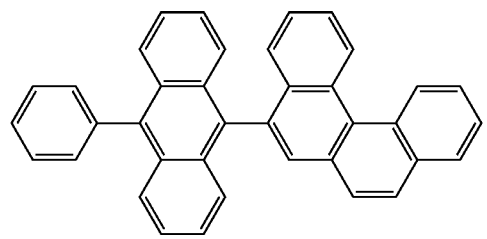
EM362
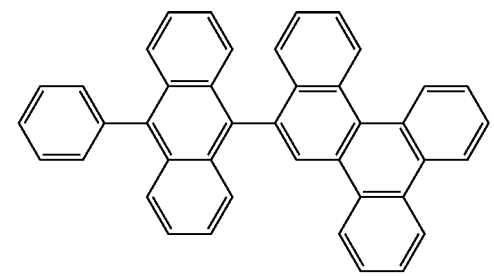
EM363
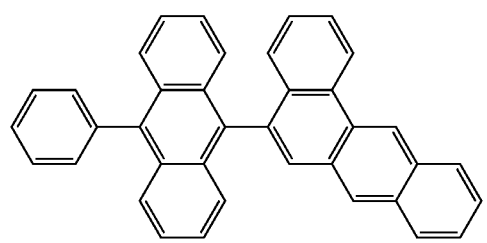
EM364
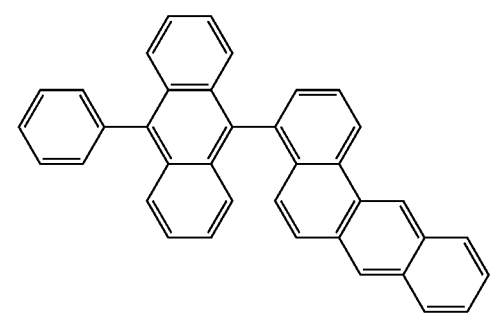
EM365
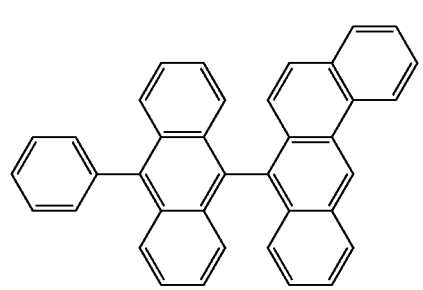
EM366
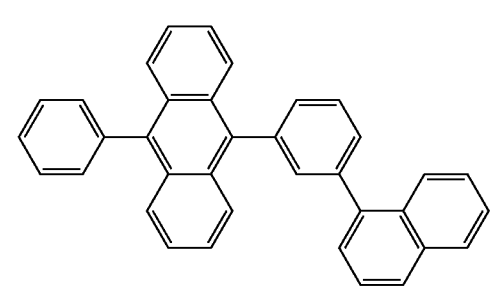

-continued
EM367
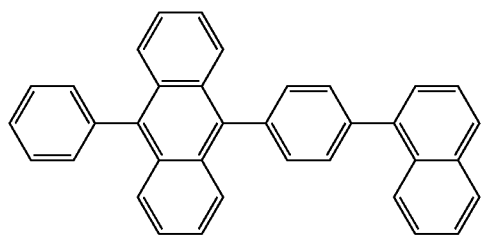
EM368
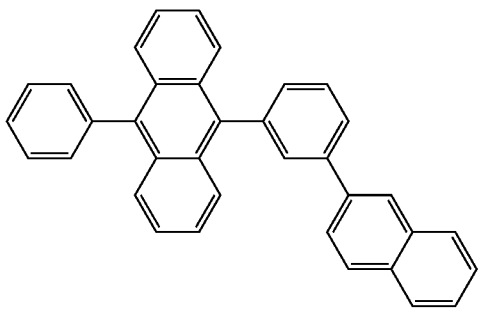
EM369
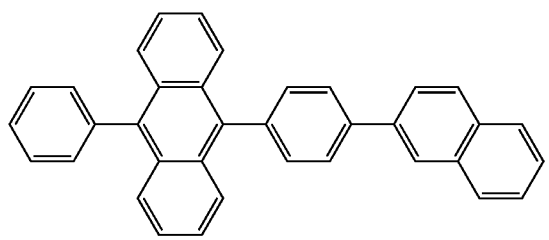
EM370
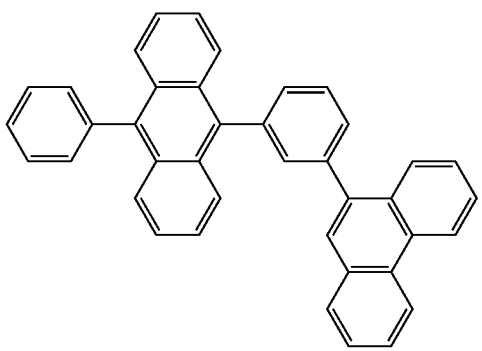
EM371
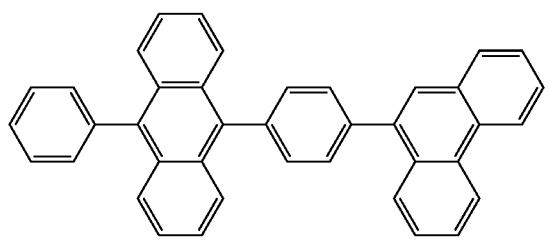
EM372
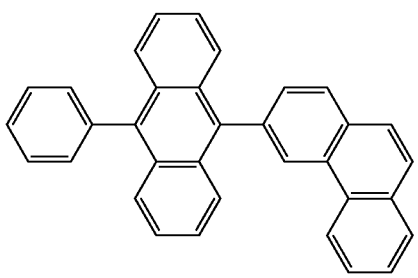
EM373
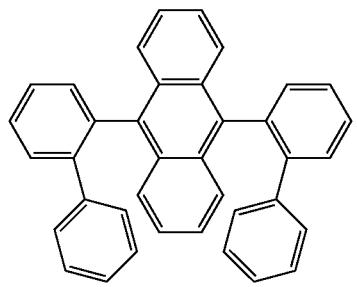
EM374
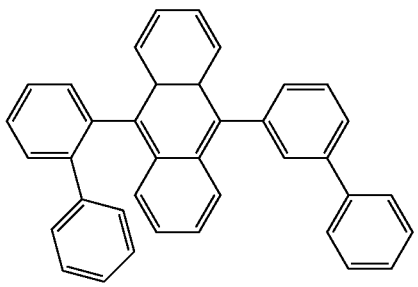

-continued

EM375
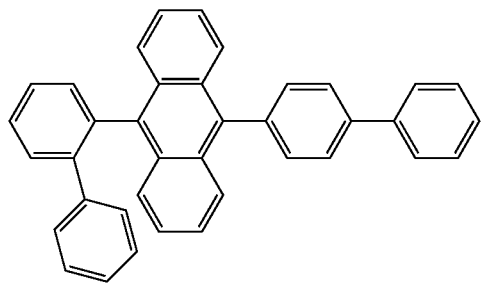

EM376
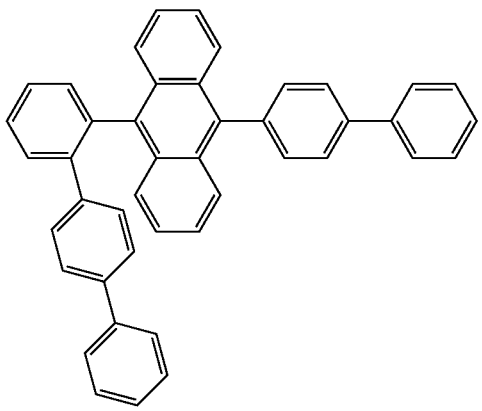

EM377
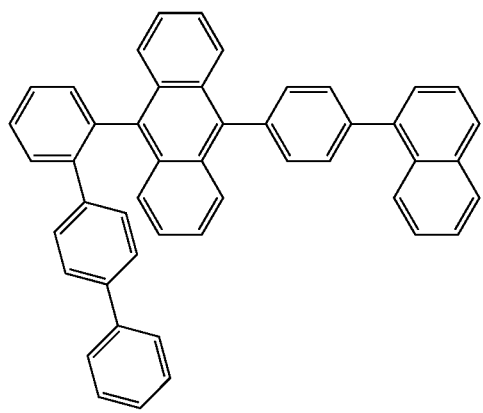

EM378
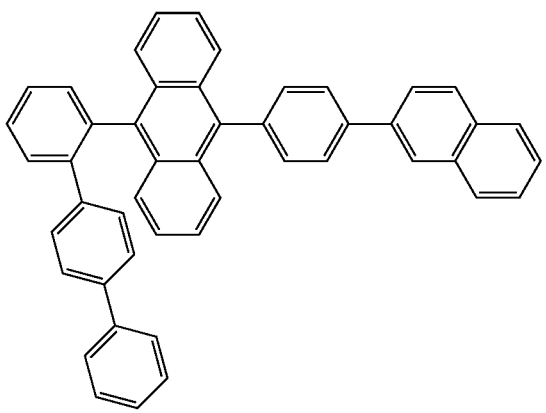

EM379
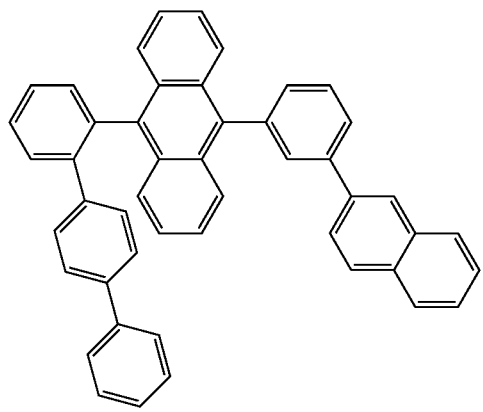

EM380
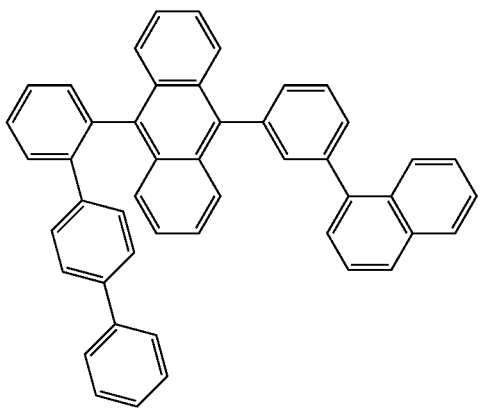

When the aromatic amine derivative of the invention is contained as a doping material (dopant), the amount thereof is preferably 0.1 to 20 mass %, more preferably 1 to 10 mass %.

To the material for an organic EL device (organic luminescent medium) of the invention, a known material for an organic EL may be added, if necessary. For example, a hole-transporting material having a bisarylamino structure or a N-arylcarbazolyl structure, or an electron-transporting compound having a benzimidazolyl structure may be added.

Specifically, materials forming a hole-injecting/transporting layer, mentioned later, or an electron-injecting material may be used.

The organic EL device of the invention comprises one or more organic thin film layers comprising an emitting layer between an anode and a cathode. At least one layer of the organic thin film layers contains the aromatic amine derivative of the invention singly or as a component of a mixture.

The aromatic amine derivative of the invention and the anthracene derivative mentioned above may be used in a hole-injecting layer, a hole-transporting layer, an electron-injecting layer, and an electron-transporting layer in addition to an emitting layer.

In the invention, as the organic EL device in which the organic thin film layer is composed of plural layers, one in which layers are sequentially stacked (anode/hole-injecting layer/emitting layer/cathode), (anode/emitting layer/electron-injecting layer/cathode), (anode/hole-injecting layer/emitting layer/electron-injecting layer/cathode), (anode/ hole-injecting layer/hole-transporting layer/emitting layer/electron-injecting layer/cathode) or the like can be given.

By allowing the organic thin film layer to be composed of plural layers, the organic EL device can be prevented from lowering of luminance or lifetime due to quenching. If necessary, an emitting material, a doping material, a hole-injecting material or an electron-injecting material can be used in combination. Further, due to the use of a doping material, luminance or luminous efficiency may be improved. The hole-injecting layer, the emitting layer and the electron-injecting layer may respectively be formed of two or more layers. In such case, in the hole-injecting layer, a layer which injects holes from an electrode is referred to as a hole-injecting layer, and a layer which receives holes from the hole-injecting layer and transports the holes to the emitting layer is referred to as a hole-transporting layer. Similarly, in the electron-injecting layer, a layer which injects electrons from an electrode is referred to as an electron-injecting layer and a layer which receives electrons from an electron-injecting layer and transports the electrons to the emitting layer is referred to as an electron-transporting layer. Each of these layers is selected and used according to each of the factors of a material, i.e. the energy level, heat resistance, adhesiveness to the organic layer or the metal electrode or the like.

Examples of the material other than the above anthracene derivative which can be used in the emitting layer together with the aromatic amine derivative of the invention include, though not limited thereto, fused polycyclic aromatic compounds such as naphthalene, phenanthrene, rubrene, tetracene, pyrene, perylene, chrysene, decacyclene, coronene, tetraphenylcyclopentadiene, pentaphenylcyclopentadiene, fluorene, spirofluorene and derivatives thereof, organic metal complexes such as tris(8-quinolinolate)aluminum, tri-arylamine derivatives, styrylamine derivatives, stilbene derivatives, coumarin derivatives, pyrane derivatives, oxazone derivatives, benzothiazole derivatives, benzoxazole derivatives, benzimidazole derivatives, pyrazine derivatives, cinnamate derivatives, diketo-pyrrolo-pyrrole derivatives, acrylidone derivatives and quinacrylidone derivatives.

As the hole-injecting material, a compound which can transport holes, exhibits hole-injecting effects from the anode and excellent hole-injection effect for the emitting layer or the emitting material, and has an excellent capability of forming a thin film is preferable. Specific examples thereof include, though not limited thereto, phthalocyanine derivatives, naphthalocyanine derivatives, porphyline derivatives, benzidine-type triphenylamine, diamine-type triphenylamine, hexacyanohexaazatriphenylene, derivatives thereof, and polymer materials such as polyvinylcarbazole, polysilane and conductive polymers.

Of the hole-injecting materials usable in the organic EL device of the invention, further effective hole-injecting materials are phthalocyanine derivatives.

Examples of the phthalocyanine (Pc) derivative include, though not limited thereto, phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc and GaPc-O-GaPc, and naphthalocyanine derivatives.

In addition, it is also possible to sensitize carriers by adding to the hole-injecting material an electron-accepting substance such as a TCNQ derivative.

Preferable hole-transporting materials usable in the organic EL device of the invention are aromatic tertiary amine derivatives.

Examples of the aromatic tertiary amine derivative include, though not limited thereto, N,N'-diphenyl-N,N'-dinaphthyl-1,1'-biphenyl-4,4'-diamine, N,N,N',N'-tetrabiphenyl-1,1'-biphenyl-4,4'-diamine or an oligomer or a polymer having these aromatic tertiary amine skeletons.

As the electron-injecting material, a compound which can transport electrons, exhibits electron-injecting effects from the cathode and excellent electron-injection effect for the emitting layer or the emitting material, and has an excellent capability of forming a thin film is preferable.

In the organic EL device of the invention, further effective electron-injecting materials are a metal complex compound and a nitrogen-containing heterocyclic derivative.

Examples of the metal complex compound include, though not limited thereto, 8-hydroxyquinolinate lithium, bis(8-hydroxyquinolinate)zinc, tris(8-hydroxyquinolinate)aluminum, tris(8-hydroxyquinolinate)gallium, bis(10-hydroxybenzo[h]quinolinate)beryllium and bis(10-hydroxybenzo[h]quinolinate)zinc.

As examples of the nitrogen-containing heterocyclic derivative, oxazole, thiazole, oxadiazole, thiadiazole, triazole, pyridine, pyrimidine, triazine, phenanthroline, benzimidazole, imidazopyridine or the like are preferable, for example. Of these, a benzimidazole derivative, a phenanthroline derivative and an imidazopyridine derivative are preferable.

As a preferred embodiment, a dopant is further contained in these electron-injecting materials, and in order to facilitate receiving electrons from the cathode, it is further preferable to dope the vicinity of the cathode interface of the second organic layer with a dopant, the representative example of which is an alkali metal.

As the dopant, a donating metal, a donating metal compound and a donating metal complex can be given. These reducing dopants may be used singly or in combination of two or more.

In the organic EL device of the invention, the emitting layer may contain, in addition to at least one of the above-mentioned aromatic amine derivatives represented by the formulas (1) to (4), at least one of an emitting material, doping material, hole-injecting material, hole-transporting material and electron-injecting material in the same layer. Moreover, for improving stability of the organic. EL device obtained by the invention to temperature, humidity, atmosphere, etc. it is also possible to prepare a protective layer on the surface of the device, and it is also possible to protect the entire device by applying silicone oil, resin, etc.

As the conductive material used in the anode of the organic EL device of the invention, a conductive material having a work function of more than 4 eV is suitable. Carbon, aluminum, vanadium, iron, cobalt, nickel, tungsten, silver, gold, platinum, palladium or the like, alloys thereof, oxidized metals which are used in an ITO substrate and a NESA substrate such as tin oxide and indium oxide and organic conductive resins such as polythiophene and polypyrrole are used. As the conductive material used in the cathode, a conductive material having a work function of smaller than 4 eV is suitable. Magnesium, calcium, tin, lead, titanium, yttrium, lithium, ruthenium, manganese, aluminum, and lithium fluoride or the like, and alloys thereof are used, but not limited thereto. Representative examples of the alloys include, though not limited thereto, magnesium/silver alloys, magnesium/indium alloys and lithium/aluminum alloys. The amount ratio of the alloy is controlled by the temperature of the deposition source, atmosphere, vacuum degree or the like, and an appropriate ratio is selected. If necessary, the anode and the cathode each may be composed of two or more layers.

In the organic EL device of the invention, in order to allow it to emit light efficiently, it is preferred that at least one of the surfaces be fully transparent in the emission wavelength region of the device. In addition, it is preferred that the substrate also be transparent. The transparent electrode is set such that predetermined transparency can be ensured by a method such as deposition or sputtering by using the above-mentioned conductive materials. It is preferred that the electrode on the emitting surface have a light transmittance of 10% or more. Although no specific restrictions are imposed on the substrate as long as it has mechanical and thermal strength and transparency, a glass substrate and a transparent resin film can be given.

Each layer of the organic EL device of the invention can be formed by a dry film-forming method such as vacuum vapor deposition, sputtering, plasma, ion plating or the like or a wet film-forming method such as spin coating, dipping, flow coating or the like. Although the film thickness is not particularly limited, it is required to adjust the film thickness to an appropriate value. If the film thickness is too large, a large voltage is required to be applied in order to obtain a certain optical output, which results in a poor efficiency. If the film thickness is too small, pinholes or the like are generated, and a sufficient luminance cannot be obtained even if an electrical field is applied. The suitable film thickness is normally 5 nm to 10 µm, with a range of 10 nm to 0.2 µm being further preferable.

In the case of the wet film-forming method, a thin film is formed by dissolving or dispersing materials forming each layer in an appropriate solvent such as ethanol, chloroform, tetrahydrofuran and dioxane. Any of the above-mentioned solvents can be used.

As the solvent suited to such a wet film-forming method, a solution containing the aromatic amine derivative of the invention as an organic EL material and a solvent can be used.

It is preferred that the organic EL material contain a host material and a dopant material, that the dopant material be the aromatic amine derivative of the invention, and that the host material be at least one selected from the anthracene derivatives represented by the formula (10).

In each organic thin film layer, an appropriate resin or additive may be used in order to improve film-forming properties, to prevent generation of pinholes in the film, or for other purposes.

The organic EL device of the invention can be suitably used as a planar emitting body such as a flat panel display of a wall-hanging television, backlight of a copier, a printer or a liquid crystal display, light sources for instruments, a display panel, a navigation light, or the like. The compound of the invention can be used not only in an organic EL device but also in the field of an electrophotographic photoreceptor, a photoelectric converting element, a solar cell and an image sensor.

EXAMPLES

Synthesis of Aromatic Amine Derivative

Example 1

An aromatic amine derivative DM-1 was produced as below.

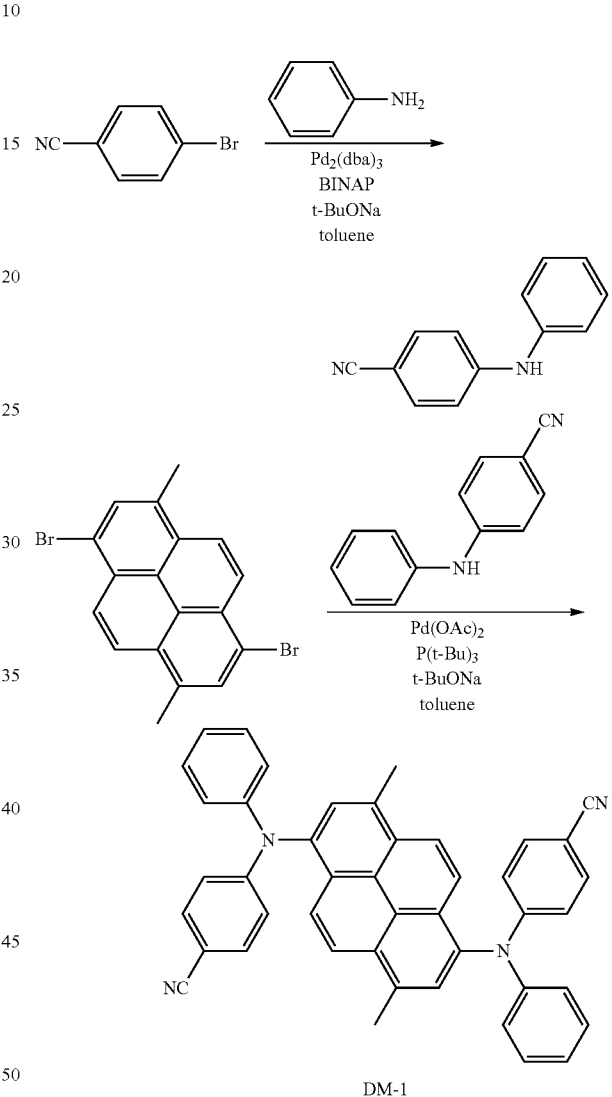

DM-1

(1) Synthesis of 4-cyanophenylphenylamine

Under a flow of argon, in a 300 mL-recovery flask, 20 g of 4-bromobenzonitrile, 30 mL of aniline, 1.50 g of tris (dibenzylideneacetone)dipalladium(0)[Pd$_2$(dba)$_3$], 2.1 g of 2,2'-bis(diphenylphosphino)-1,1'-binaphthyl[BINAP], 21.1 g of sodium tert-butoxide and 313 mL of dehydrated toluene were placed, and reacted at 85° C. for 6 hours.

After cooling, the reaction solution was filtered through celite. The crude product obtained was purified by means of silica-gel chromatography, and resulting solids were dried under reduced pressure, whereby 14.9 g of white solids were obtained (yield 70%).

(2) Synthesis of DM-1

Under a flow of argon, in a 300 mL-recovery flask, 7.2 g of 4-cyanophenyiphenylamine, 5.7 g of 1,6-dibromo-3,8-dimethylpyrene, 2.8 g of sodium tert-butoxide, 160 mg of palladium(II)acetate [Pd(OAc)$_2$], 135 mg of tri-tert-butylphosphine and 73 mL of dehydrated toluene were placed, and reacted at 85° C. for 7 hours.

The reaction solution was filtered, and the crude product obtained was purified by means of silica-gel chromatography. Solids obtained were re-crystallized with toluene, and resulting solids were dried under reduced pressure, whereby 2.6 g of yellow white solids were obtained. As a result of FD-MS (Field desorption mass spectrometry), the resulting compound was confirmed to be an intended product, which had an m/e of 614 for the molecular weight 614.25.

Example 2

As shown below, an aromatic amine derivative DM-2 was produced in the same manner as in Example 1, except that 1,6-dibromo-3,8-diisopropylpyrene was used instead of 1,6-dibromo-3,8-dimethylpyrene. As a result of mass spectroscopy analysis, the resulting compound was confirmed to be an intended product, which had an m/e of 670 for the molecular weight 670.31.

Example 3

An aromatic amine derivative DM-3 was produced as below.

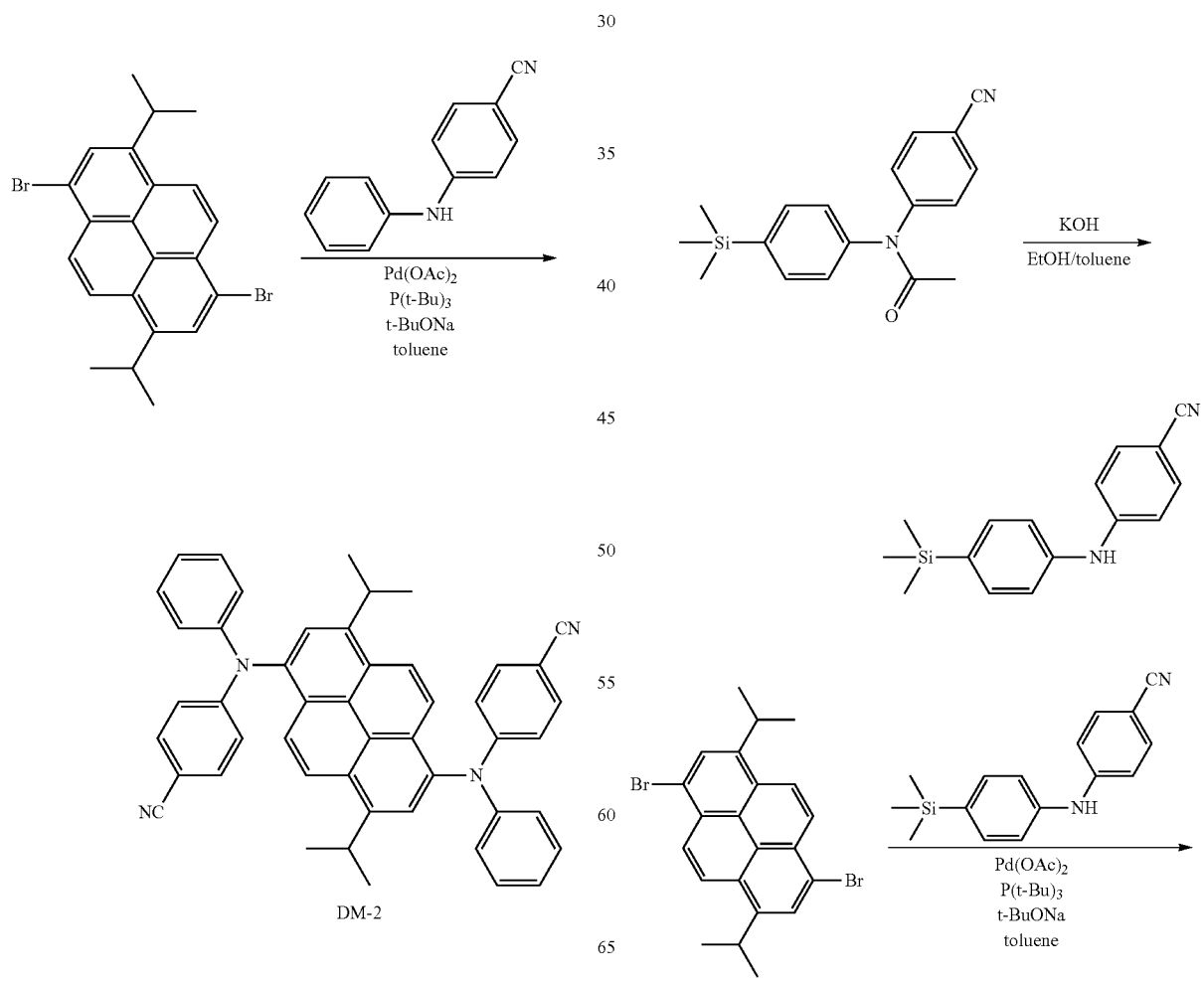

-continued

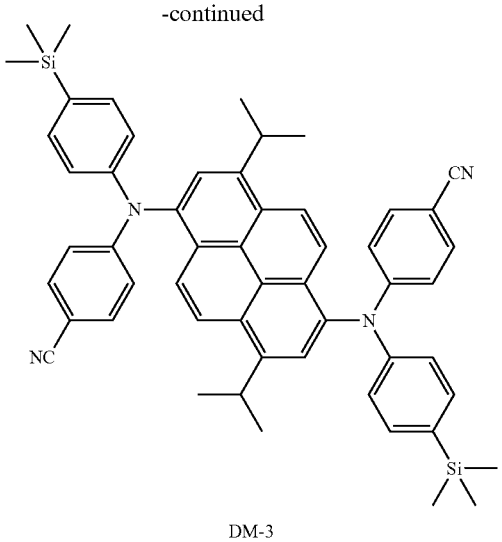

DM-3

(1) Synthesis of N-(4-(trimethylsilyl)phenyl)acetamide

Under a flow of argon, in a 1 L-recovery flask, 35 g of 1-bromo-4-(trimethylsilyl)benzene, 22.6 g of acetamide, 5.8 g of copper(I)iodide, 42.2 g of potassium carbonate, and 380 mL of xylene were placed. After stirring, 6.6 mL of N,N'-dimethylethylenediamine was added. The resultant was heated and stirred at reflux for 18 hours.

The reaction solution was filtered. The crude product obtained was washed with toluene, clean water and methanol. Resulting solids were dried under reduced pressure, whereby 27 g of solids were obtained.

(2) Synthesis of N-(4-cyanophenyl)-N-(4-(trimethylsilyl)phenyl)acetamide

Under a flow of argon, in a 1 L-recovery flask, 27 g of N-(4-(trimethylsilyl)phenyl)acetamide, 30 g of 4-bromobenzonitrile, 6.3 g of copper (I) iodide, 45.6 g of potassium carbonate, and 412 mL of xylene were placed. After stirring, 7.1 mL of N,N'-dimethylethylenediamine was added. The resultant was heated and stirred at reflux for 18 hours.

The reaction solution was extracted with toluene and then filtered. After a filtrate was concentrated, a residue was purified by means of silica-gel chromatography to obtain 34 g of solids.

(3) Synthesis of (4-cyanophenyl)(4-trimethylsilylphenyl)amine

In a 300 mL-recovery flask, 34 g of N-(4-cyanophenyl)-N-(4-(trimethylsilyl)phenyl)acetamide, 43 g of potassium hydroxide, 39 mL of clean water, 60 mL of toluene and 120 mL of ethanol were placed, and heated and stirred at reflux for 8 hours.

Ethyl acetate was added to the resultant, and separation and extraction were conducted. After that, an organic phase was washed with clean water and saturated saline, and dried with sodium sulfate. The crude product obtained by concentration was purified by means of silica-gel chromatography. Resulting solids were dried under reduced pressure, whereby 17 g of white solids were obtained (yield 59%).

(4) Synthesis of DM-3

Under a flow of argon, in a 300 mL-recovery flask, 7.5 g of (4-cyanophenyl)(4-trimethylsilylphenyl)amine, 5.0 g of 1,6-dibromo-3,8-diisopropylpyrene, 2.2 g of sodium tert-butoxide, 130 mg of palladium(II)acetate[Pd(OAc)$_2$], 135 mg of tri-tert-butylphosphine and 113 mL of dehydrated toluene were placed, and reacted at 85° C. for 7 hours.

The reaction solution was filtered, and the crude product obtained was purified by means of silica-gel chromatography. Solids obtained were re-crystallized with toluene, and resulting solids were dried under reduced pressure, whereby 8.0 g of yellow white solids were obtained. As a result of FD-MS (Field desorption mass spectrometry), the resulting compound was confirmed to be an intended product, which had an m/e of 814 for the molecular weight 814.39.

Example 4

As shown below, an aromatic amine derivative DM-4 was produced in the same manner as in Example 3, except that 4-bromobenzonitrile was used instead of 1-bromo-4-(trimethylsilyl)benzene, and N,N-bis(4-cyanophenyl)acetamide was synthesized. As a result of mass spectroscopy analysis, the resulting compound was confirmed to be an intended product, which had an m/e of 720 for the molecular weight 720.30.

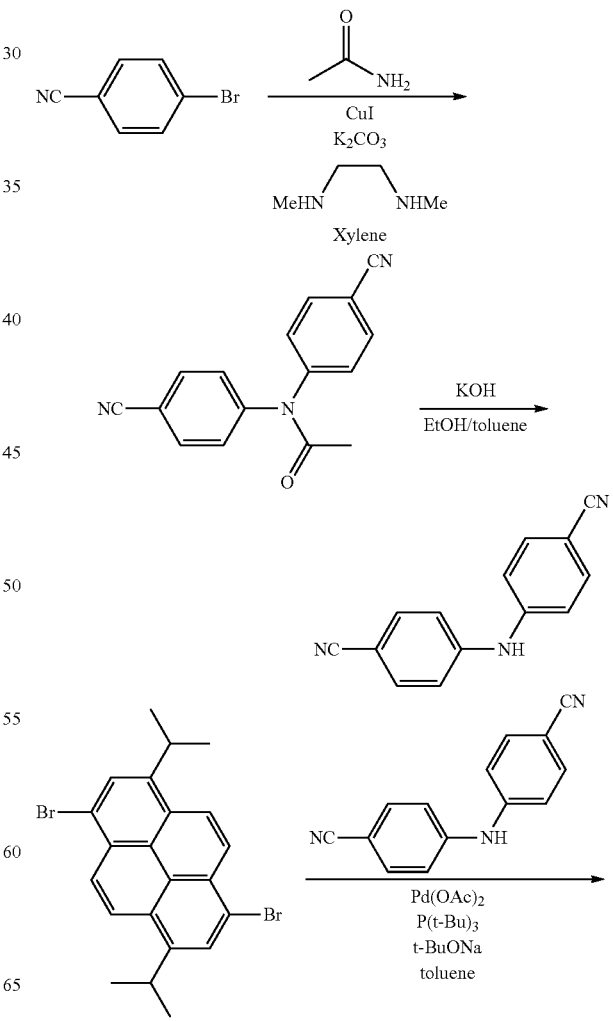

-continued

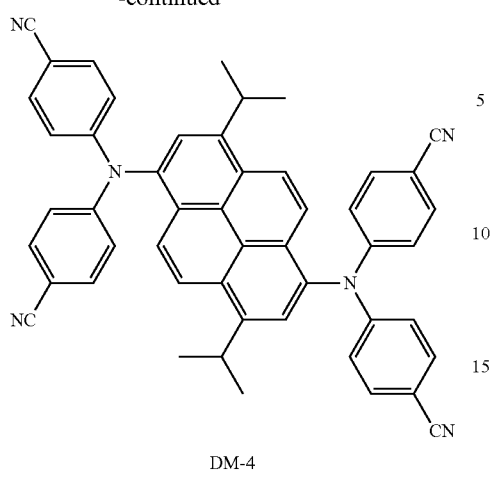

DM-4

-continued

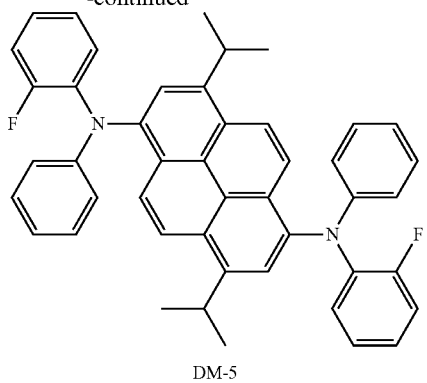

DM-5

Fabrication of Organic EL Device

Example 6

A glass substrate of 25 mm by 75 mm by 1.1 mm thick with an ITO transparent electrode (anode) (GEOMATEC CO., LTD.) was subjected to ultrasonic cleaning in isopropyl alcohol for 5 minutes, and cleaning with UV/ozone for 30 minutes. The cleaned glass substrate with transparent electrode lines was mounted on a substrate holder in a vacuum deposition apparatus. First, compound A-1 was deposited on the surface on which the transparent electrode lines were formed so as to cover the transparent electrode to form a 50 nm-thick film Subsequently, compound A-2 was deposited on the A-1 film to form a 45 nm-thick film.

Compound EM2 and compound DM-1 of the invention were deposited on the A-2 film into a thickness of 20 nm such that the film thickness ratio of EM2 and DM-1 became 20:1 to form a blue emitting layer.

On this film, the following ET-1 was deposited into a thickness of 30 nm as an electron-transporting layer. Then, LIE was deposited into a thickness of 1 nm. Metallic Al was deposited on the LiF film into a thickness of 150 nm to form a metallic cathode, whereby an organic EL device was fabricated.

Example 5

As below, an aromatic amine derivative DM-5 was produced in the same manner as in Example 1, except that 2-bromofluorobenzene was used instead of 4-bromobenzonitrile, and (2-fluorophenyl)phenylamine was synthesized. As a result of a mass spectroscopy analysis, the resulting compound was confirmed to be an intended product, which had an m/e of 656 for the molecular weight 656.30.

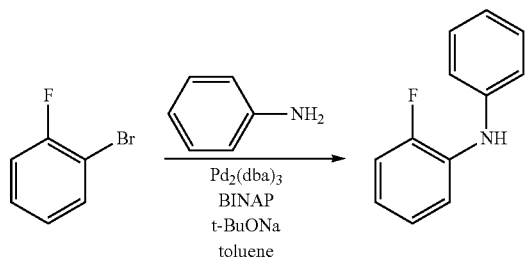

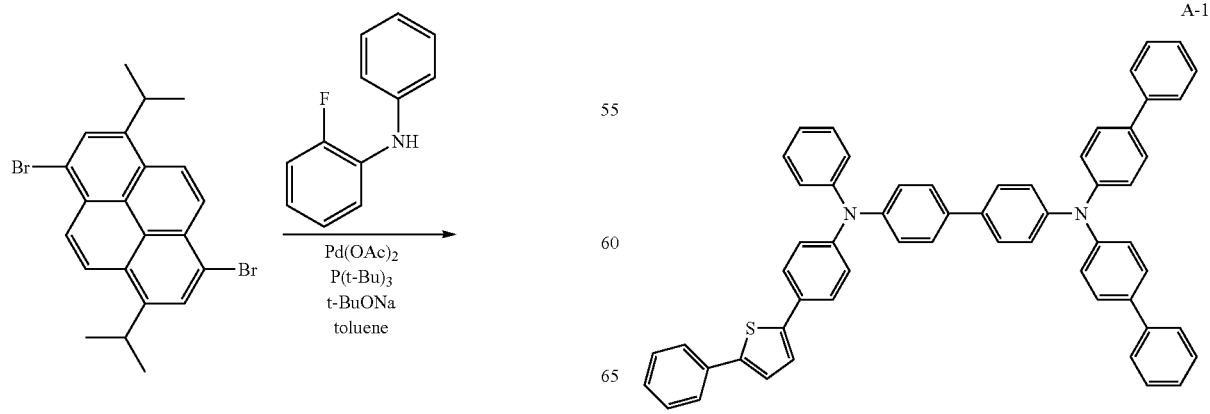

A-1

-continued

A-2
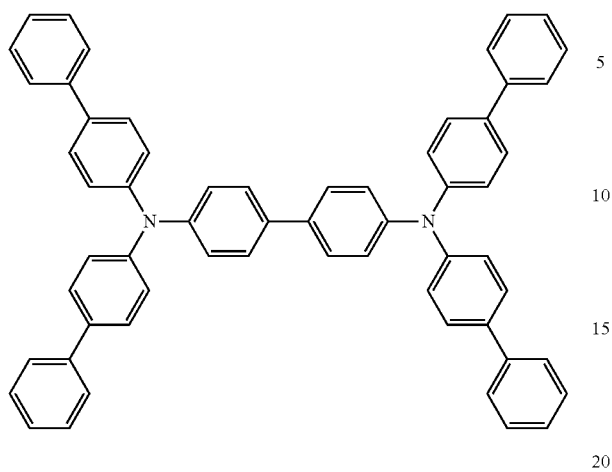

ET-1
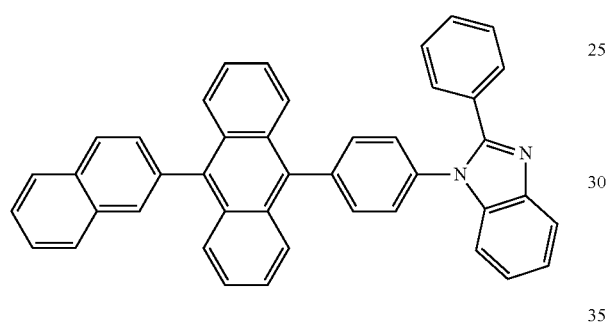

-continued

DM-C2
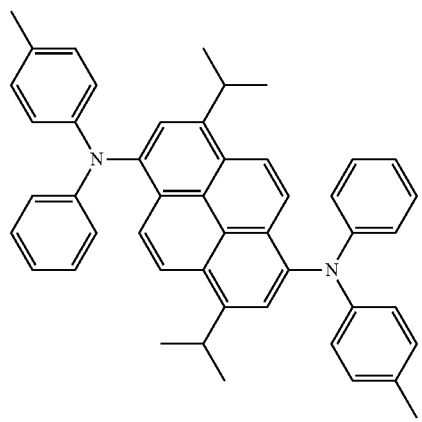

DM-C3
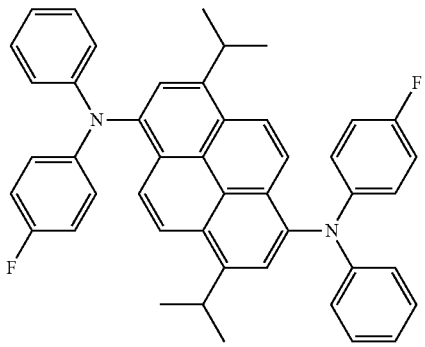

Examples 7 to 78, Comparative Examples 1 to 3

Organic EL devices were produced in the same manner as in Example 6, except that the host materials and doping materials shown in Tables 1 and 2 were used.

The doping materials used in Comparative Examples 1 to 3 are shown below.

DM-C1
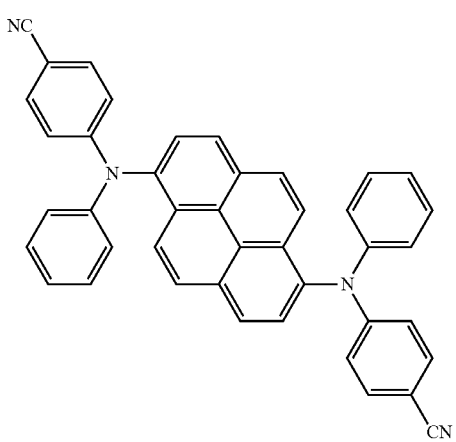

Current having a current density of 10 mA/cm² was applied to the organic EL devices produced in the Examples and Comparative Examples given above. Emission spectra thereof were measured with a spectroradiometer (CS1000, produced by MINOLTA), and external quantum efficiency was calculated by the following formula (1).

The lifetime of the organic EL device was evaluated by measuring the half life at 500 cd/m² of initial luminance. The results are shown in Tables 1 and 2.

$$E.Q.E. = \frac{N_P}{N_E} \times 100$$

$$= \frac{(\pi/10^9)\int \phi(\lambda) \cdot d\lambda}{\frac{hc}{J/10}} \times 100$$

$$= \frac{(\pi/10^9)\Sigma(\phi(\lambda) \cdot (\lambda))}{\frac{hc}{J/10}} \times 100(\%)$$

$N_P$ : Number of Photons $N_E$ : Number of electrons $\pi$ : Circular constant = 3.1416

$\lambda$ : Wavelength(nm)

$\varphi$ : Luminescence intensity(W/sr·m²·nm)

$h$ : Planck constant = $6.63 \times 10^{-34}$ (J·s)

$c$ : Light velocity = $3 \times 10^8$ (m/s)

$J$ : Current density (mA/cm²)

$e$ : Charge = $1.6 \times 10^{-19}$ (C)

TABLE 1

|  | Host | Dopant | CIEx | CIEy | EQE (%) | Life (h) |
|---|---|---|---|---|---|---|
| Example 6 | EM2 | DM-1 | 0.137 | 0.098 | 7.2 | 3300 |
| Example 7 | EM9 | DM-1 | 0.137 | 0.093 | 7.1 | 3300 |
| Example 8 | EM13 | DM-1 | 0.137 | 0.094 | 7.7 | 3900 |
| Example 9 | EM28 | DM-1 | 0.137 | 0.094 | 7.7 | 4000 |
| Example 10 | EM29 | DM-1 | 0.137 | 0.093 | 7.2 | 3400 |
| Example 11 | EM31 | DM-1 | 0.137 | 0.094 | 7.7 | 4200 |
| Example 12 | EM32 | DM-1 | 0.137 | 0.096 | 7.6 | 4100 |
| Example 13 | EM69 | DM-1 | 0.137 | 0.096 | 7.5 | 3800 |
| Example 14 | EM70 | DM-1 | 0.137 | 0.094 | 7.5 | 3700 |
| Example 15 | EM73 | DM-1 | 0.137 | 0.096 | 7.6 | 3900 |
| Example 16 | EM78 | DM-1 | 0.137 | 0.096 | 7.5 | 3400 |
| Example 17 | EM82 | DM-1 | 0.137 | 0.096 | 7.4 | 3400 |
| Example 18 | EM125 | DM-1 | 0.137 | 0.096 | 7.6 | 3800 |
| Example 19 | EM205 | DM-1 | 0.137 | 0.096 | 7.4 | 3300 |
| Example 20 | EM360 | DM-1 | 0.137 | 0.096 | 7.4 | 3100 |
| Example 21 | EM364 | DM-1 | 0.137 | 0.101 | 7.1 | 2900 |
| Example 22 | EM367 | DM-1 | 0.137 | 0.096 | 7.4 | 3100 |
| Example 23 | EM372 | DM-1 | 0.137 | 0.096 | 7.5 | 3100 |
| Example 24 | EM2 | DM-2 | 0.137 | 0.098 | 7.2 | 3400 |
| Example 25 | EM9 | DM-2 | 0.137 | 0.093 | 7.1 | 3400 |
| Example 26 | EM13 | DM-2 | 0.137 | 0.094 | 7.7 | 4000 |
| Example 27 | EM28 | DM-2 | 0.137 | 0.094 | 7.7 | 4100 |
| Example 28 | EM29 | DM-2 | 0.137 | 0.093 | 7.2 | 3500 |
| Example 29 | EM31 | DM-2 | 0.137 | 0.094 | 7.7 | 4300 |
| Example 30 | EM32 | DM-2 | 0.137 | 0.096 | 7.6 | 4200 |
| Example 31 | EM69 | DM-2 | 0.137 | 0.096 | 7.5 | 3900 |
| Example 32 | EM70 | DM-2 | 0.137 | 0.094 | 7.5 | 3800 |
| Example 33 | EM73 | DM-2 | 0.137 | 0.096 | 7.6 | 4000 |
| Example 34 | EM78 | DM-2 | 0.137 | 0.096 | 7.5 | 3500 |
| Example 35 | EM82 | DM-2 | 0.137 | 0.096 | 7.4 | 3500 |
| Example 36 | EM125 | DM-2 | 0.137 | 0.096 | 7.6 | 3900 |
| Example 37 | EM205 | DM-2 | 0.137 | 0.096 | 7.4 | 3400 |
| Example 38 | EM360 | DM-2 | 0.137 | 0.096 | 7.4 | 3200 |
| Example 39 | EM364 | DM-2 | 0.137 | 0.101 | 7.1 | 3000 |
| Example 40 | EM367 | DM-2 | 0.137 | 0.096 | 7.4 | 3200 |
| Example 41 | EM372 | DM-2 | 0.137 | 0.096 | 7.5 | 3200 |

TABLE 2

|  | Host | Dopant | CIEx | CIEy | EQE (%) | Life (h) |
|---|---|---|---|---|---|---|
| Example 42 | EM2 | DM-3 | 0.137 | 0.099 | 7.3 | 3300 |
| Example 43 | EM9 | DM-3 | 0.137 | 0.094 | 7.2 | 3300 |
| Example 44 | EM13 | DM-3 | 0.137 | 0.095 | 7.8 | 3900 |
| Example 45 | EM28 | DM-3 | 0.137 | 0.095 | 7.8 | 4000 |
| Example 46 | EM29 | DM-3 | 0.137 | 0.094 | 7.3 | 3400 |
| Example 47 | EM31 | DM-3 | 0.137 | 0.095 | 7.8 | 4200 |
| Example 48 | EM32 | DM-3 | 0.137 | 0.097 | 7.7 | 4100 |
| Example 49 | EM69 | DM-3 | 0.137 | 0.097 | 7.6 | 3800 |
| Example 50 | EM70 | DM-3 | 0.137 | 0.095 | 7.6 | 3700 |
| Example 51 | EM73 | DM-3 | 0.137 | 0.097 | 7.7 | 3900 |
| Example 52 | EM78 | DM-3 | 0.137 | 0.097 | 7.6 | 3400 |
| Example 53 | EM82 | DM-3 | 0.137 | 0.097 | 7.5 | 3400 |
| Example 54 | EM125 | DM-3 | 0.137 | 0.097 | 7.7 | 3800 |
| Example 55 | EM205 | DM-3 | 0.137 | 0.097 | 7.5 | 3300 |
| Example 56 | EM360 | DM-3 | 0.137 | 0.097 | 7.5 | 3100 |
| Example 57 | EM364 | DM-3 | 0.137 | 0.102 | 7.2 | 2900 |
| Example 58 | EM367 | DM-3 | 0.137 | 0.097 | 7.5 | 3100 |
| Example 59 | EM372 | DM-3 | 0.137 | 0.097 | 7.6 | 3100 |
| Example 60 | EM2 | DM-4 | 0.147 | 0.074 | 7.0 | 2300 |
| Example 61 | EM9 | DM-4 | 0.147 | 0.069 | 6.9 | 2300 |
| Example 62 | EM13 | DM-4 | 0.147 | 0.070 | 7.5 | 2900 |
| Example 63 | EM28 | DM-4 | 0.147 | 0.070 | 7.5 | 3000 |
| Example 64 | EM29 | DM-4 | 0.147 | 0.069 | 7.0 | 2400 |
| Example 65 | EM31 | DM-4 | 0.147 | 0.070 | 7.5 | 3200 |
| Example 66 | EM32 | DM-4 | 0.147 | 0.072 | 7.4 | 3100 |
| Example 67 | EM69 | DM-4 | 0.147 | 0.072 | 7.3 | 2800 |
| Example 68 | EM70 | DM-4 | 0.147 | 0.070 | 7.3 | 2700 |
| Example 69 | EM73 | DM-4 | 0.147 | 0.072 | 7.4 | 2900 |
| Example 70 | EM78 | DM-4 | 0.147 | 0.072 | 7.3 | 2400 |
| Example 71 | EM82 | DM-4 | 0.147 | 0.072 | 7.2 | 2400 |
| Example 72 | EM125 | DM-4 | 0.147 | 0.072 | 7.4 | 2800 |
| Example 73 | EM205 | DM-4 | 0.147 | 0.072 | 7.2 | 2300 |
| Example 74 | EM360 | DM-4 | 0.147 | 0.072 | 7.2 | 2100 |
| Example 75 | EM364 | DM-4 | 0.147 | 0.077 | 6.9 | 1900 |
| Example 76 | EM367 | DM-4 | 0.147 | 0.072 | 7.2 | 2100 |
| Example 77 | EM372 | DM-4 | 0.147 | 0.072 | 7.3 | 2100 |
| Example 78 | EM28 | DM-5 | 0.144 | 0.080 | 7.4 | 2100 |
| Com. Ex. 1 | EM2 | DM-C1 | 0.137 | 0.096 | 6.8 | 1000 |
| Com. Ex. 2 | EM2 | DM-C2 | 0.126 | 0.175 | 6.5 | 1800 |
| Com. Ex. 3 | EM28 | DM-C3 | 0.133 | 0.150 | 6.9 | 2500 |

As seen from Tables 1 and 2, by using the diaminopyrene derivative of the invention, an organic EL device capable emitting pure blue color light and having a long lifetime can be realized. As compared with Comparative Example 1, it is clear that the diaminopyrene derivative of the invention which has a substituent at a mother nucleus enables an organic EL device to have a significantly longer lifetime than the compound having no substituent at a mother nucleus.

Furthermore, as compared with Comparative Example 2, the diaminopyrene derivative of the invention enables an organic EL device to emit significantly pure blue light and to have a longer lifetime than the compound having no cyano group.

Comparison between Comparative Example 3 and Example 78 reveals that the organic EL device using the compound in which at least one of $Ar_1$ to $Ar_4$ is o-fluorophenyl can emit significantly pure blue light and has a longer lifetime than that using the compound in which at least one of $Ar_1$ to $Ar_4$ is p-fluorophenyl. Here, when lifetime is measured at the same luminance, luminosity factor is likely to vary with an increase in color purity. Therefore, a high current is required to be applied. When a high current is applied, due to load imposed on the compound, the lifetime of the EL device tends to be short. As mentioned above, it has been considered that it is difficult to achieve both high color purity and long lifetime. However, this can be achieved by using the diaminopyrene derivative of the invention.

Moreover, further significant effects are exhibited due to the combination of a specific anthracene host. Of these, an anthracene derivative substituted by a fused ring, the representative examples of which include EM28, EM29, EM31, EM32, EM69, EM70 and EM73, significantly contributes to a prolongation of lifetime. Further preferable are 1-naphthyl-substituted anthracene derivatives, the representative examples of which include EM28, EM29, EM31 and EM32. It is more preferable to use the host material stated in the examples. However, the anthracene derivative which is within the scope of the claims of the invention can be preferable used, since it can exhibit similar advantageous effects.

As stated above, a display device which has a long lifetime and has high color reproducibility can be realized by the invention.

INDUSTRIAL APPLICABILITY

The organic EL device of the invention can be suitably used as a planar emitting body such as a flat panel display of a wall television, backlight of a copier, a printer, or a liquid crystal display, light sources for instruments, a display panel, a navigation light, and the like.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. An anthracene derivative selected from the group consisting of the following compounds:

EM311

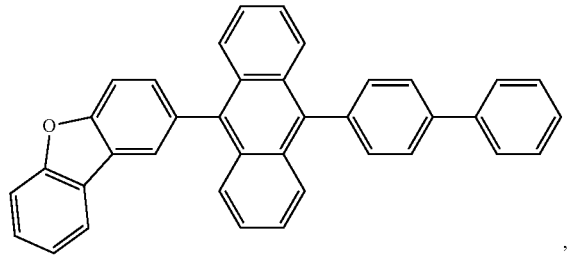

EM312

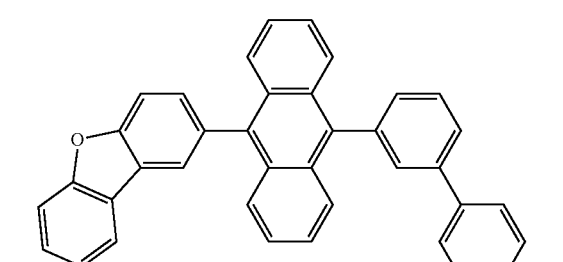

EM313

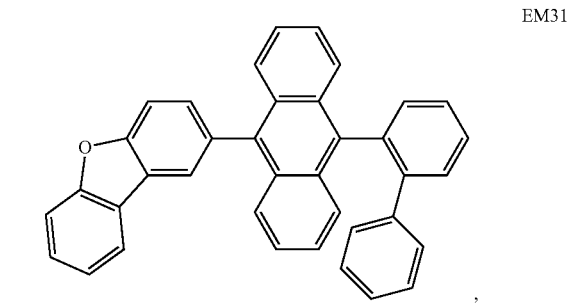

EM314

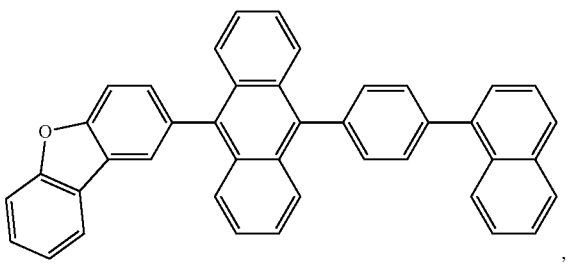

EM315

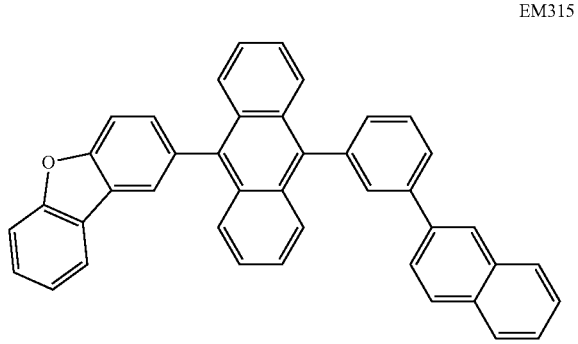 [SMILES: c1cc(-c2ccc3ccccc3c2)cc(-c2c3ccccc3c(-c3ccc4oc5ccccc5c4c3)c3ccccc23)c1]

EM316

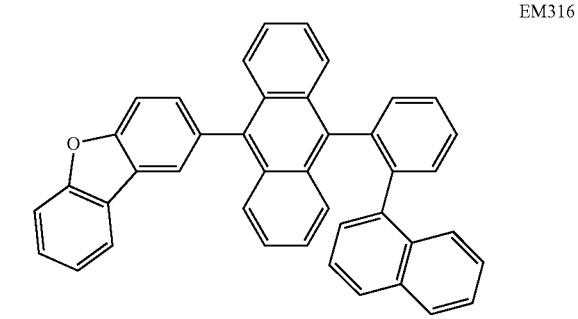 [SMILES: c1ccc(-c2c3ccccc3c(-c3ccc4oc5ccccc5c4c3)c3ccccc23)c(-c2cccc3ccccc23)c1]

EM317

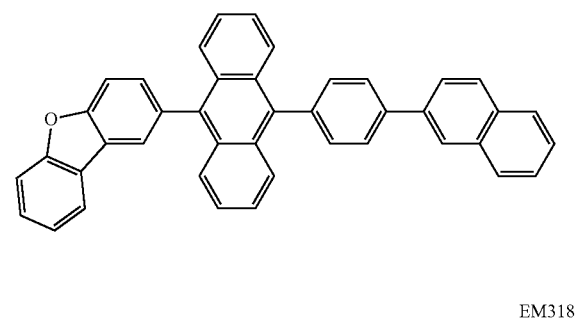

EM318

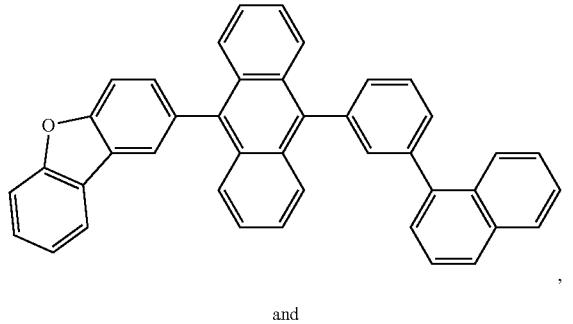

and

-continued
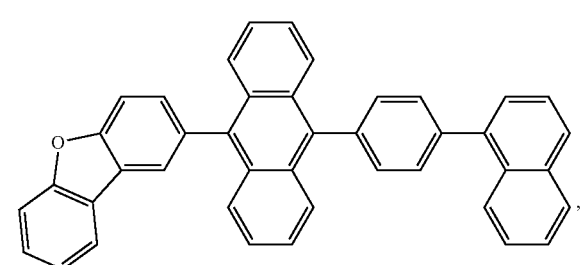
EM314
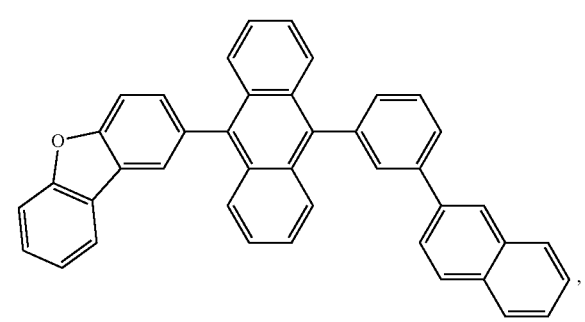
EM315
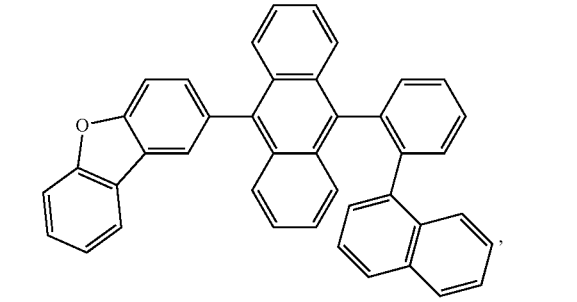
EM316
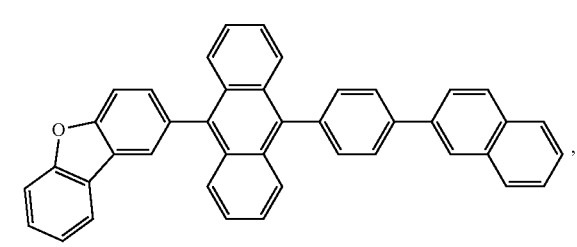
EM317
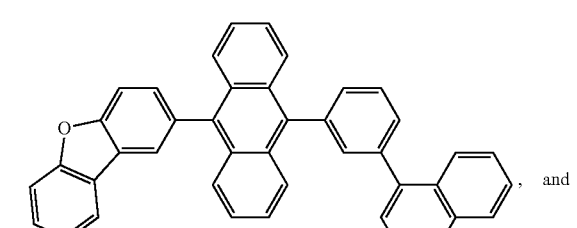
EM318, and
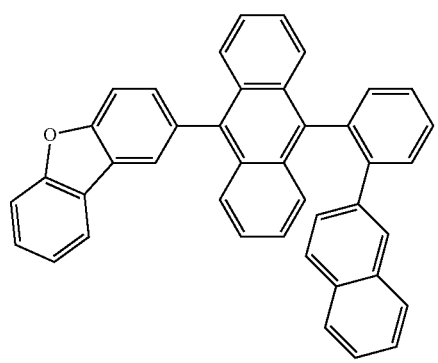
EM319
2. An anthracene derivative which is selected from the group consisting of the following compounds:
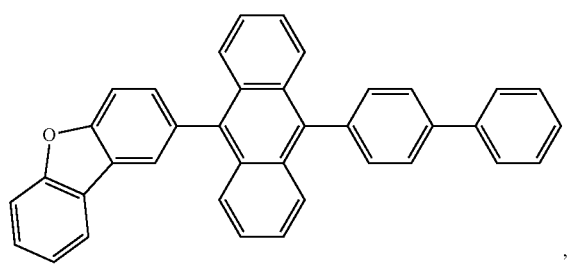
EM311,
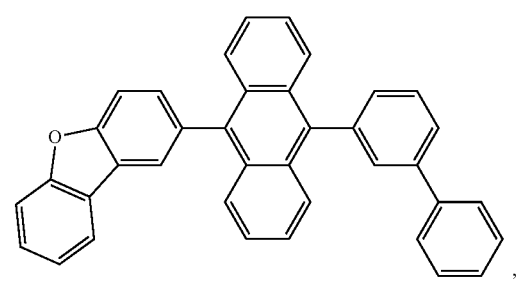
EM312, and
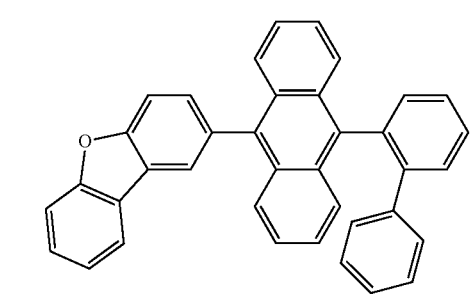
EM313
3. The anthracene derivative according to claim 1, which is selected from the group consisting of the following compounds:

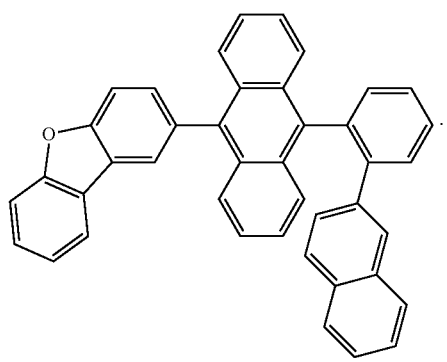
EM319

4. The anthracene derivative according to claim 1, which is selected from the group consisting of the following compounds:

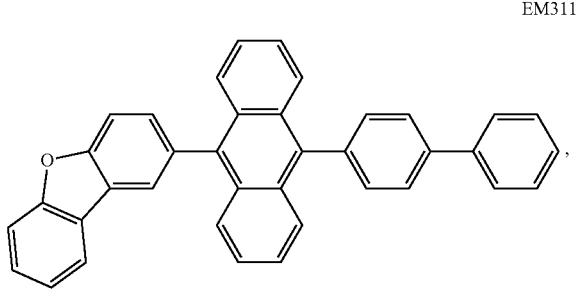 [SMILES: c1ccc(-c2ccc(-c3c4ccccc4c(-c4ccc5oc6ccccc6c5c4)c4ccccc34)cc2)cc1]
EM311

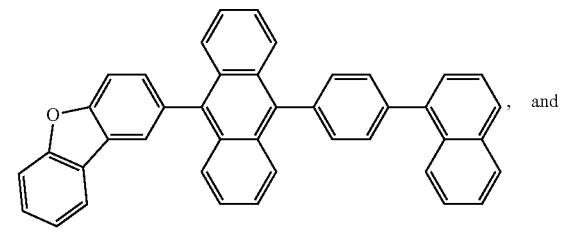
EM314

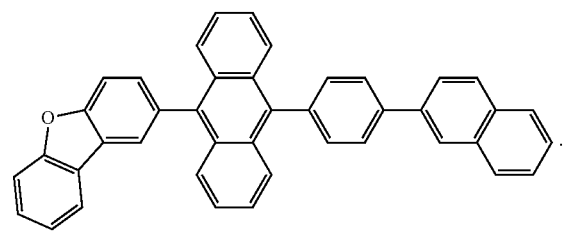
EM317

5. The anthracene derivative according to claim 1, is the following compound:

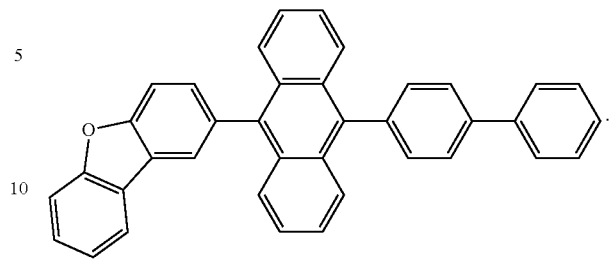
EM311

6. The anthracene derivative according to claim 1, which is the following compound:

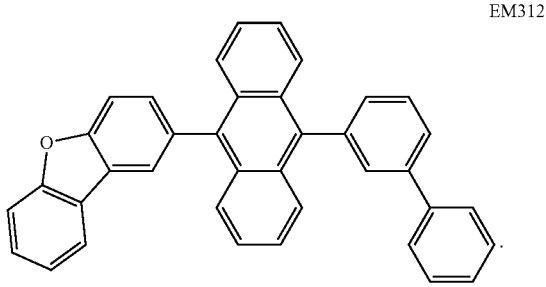
EM312

7. The anthracene derivative according to claim 1, which is the following compound:

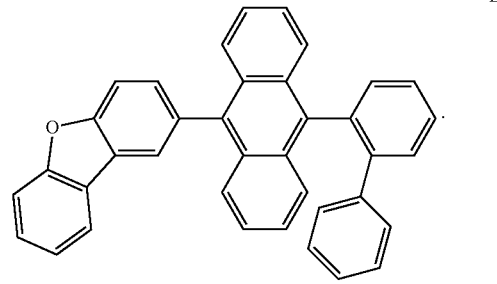
EM313

8. The anthracene derivative according to claim 1, which is the following compound:

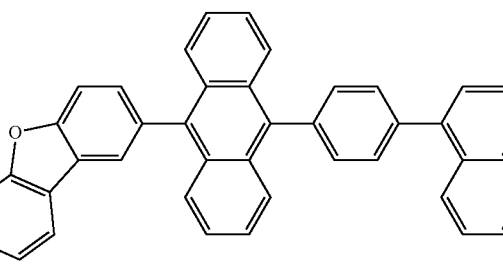
EM314

9. The anthracene derivative according to claim 1, which is the following compound:

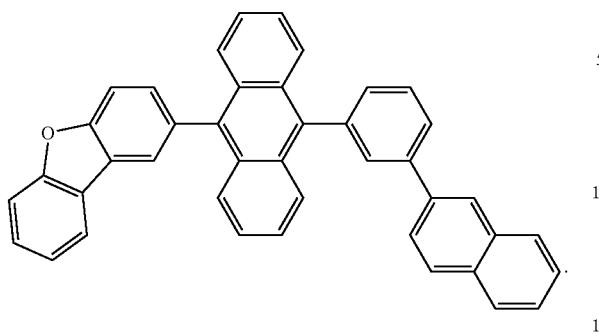

10. The anthracene derivative according to claim 1, which is the following compound:

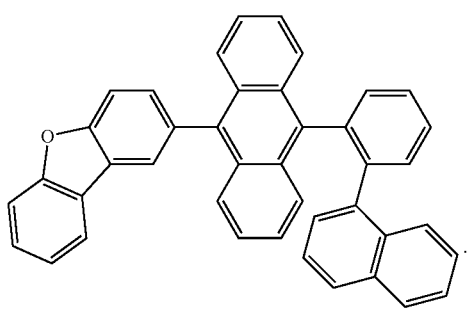

11. The anthracene derivative according to claim 1, which is the following compound:

12. The anthracene derivative according to claim 1, which is the following compound:

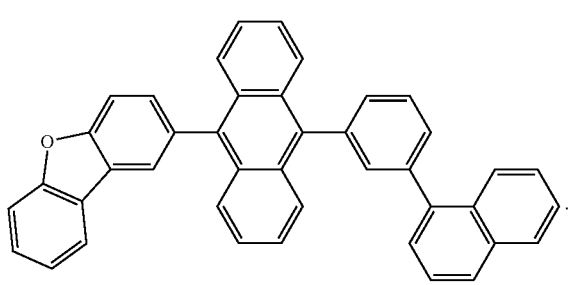

13. The anthracene derivative according to claim 1, which is the following compound:

14. An organic electroluminescence device comprising a cathode, an anode, and one or more organic thin film layers comprising an emitting layer therebetween, wherein the emitting layer comprises the anthracene derivative according to claim 1.

15. The organic electroluminescence device according to claim 14, wherein the anthracene derivative is selected from the group consisting of the following compounds:

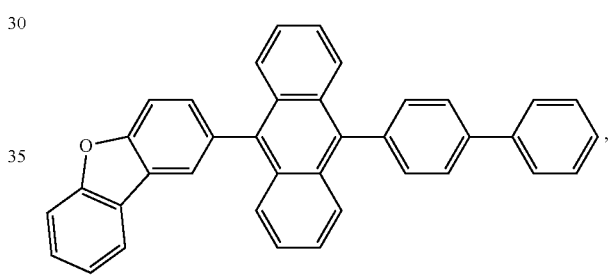

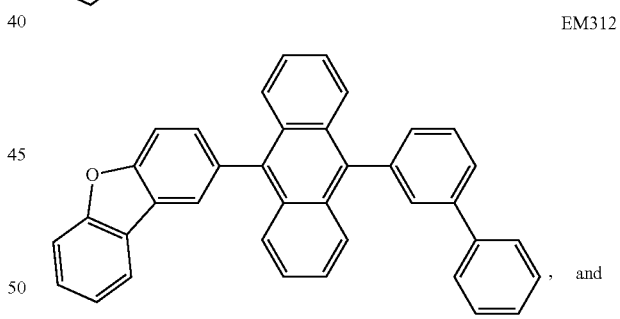

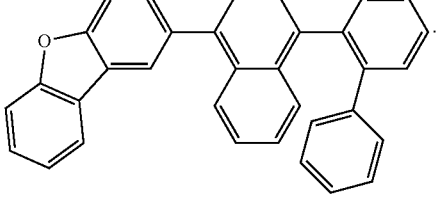

16. The organic electroluminescence device according to claim 14, wherein the anthracene derivative is selected from the group consisting of the following compounds:

EM314
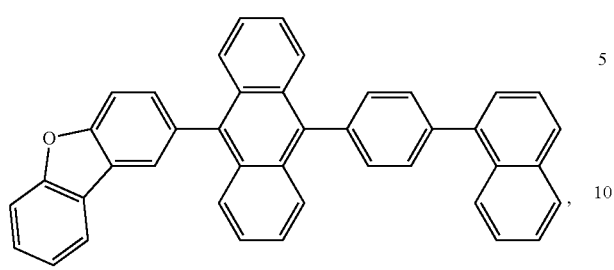
EM315
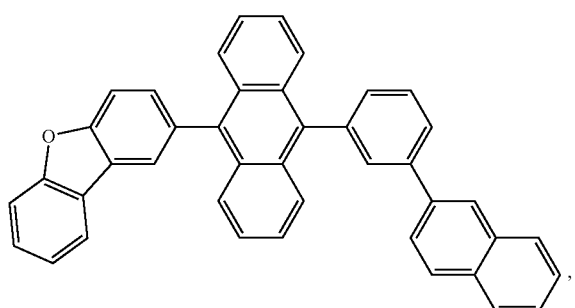
EM319
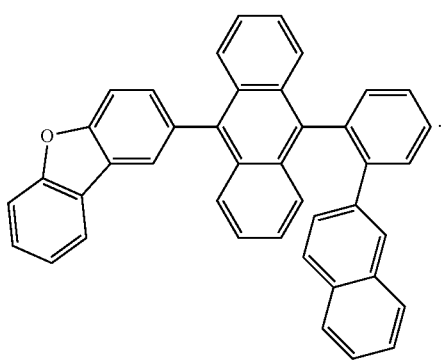
EM316
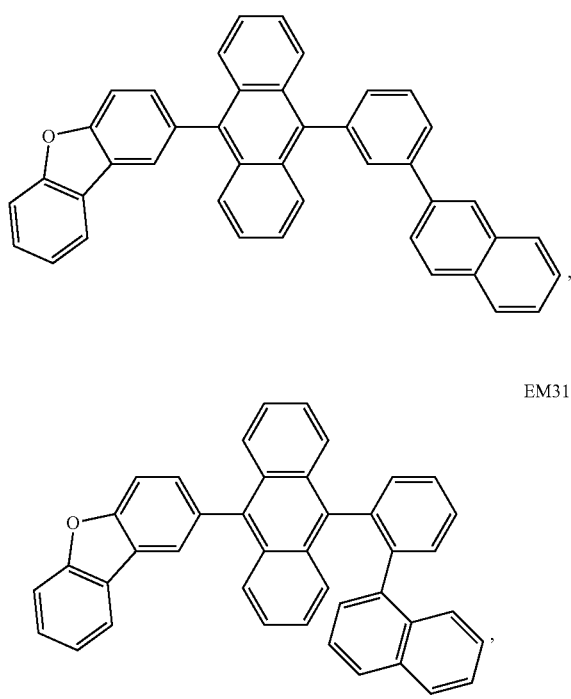
17. The organic electroluminescence device according to claim 14, wherein the anthracene derivative is selected from the group consisting of the following compounds:
EM311
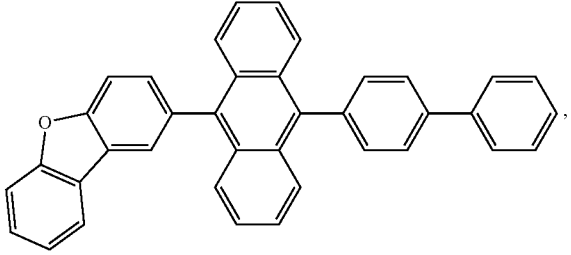
EM317
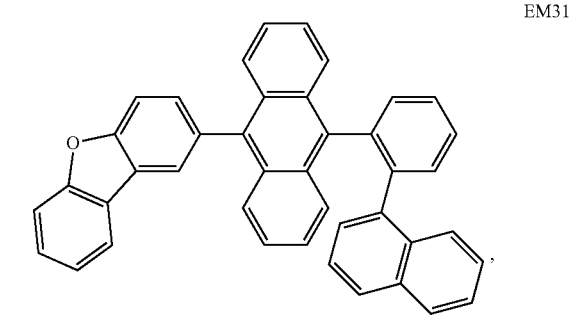
EM314
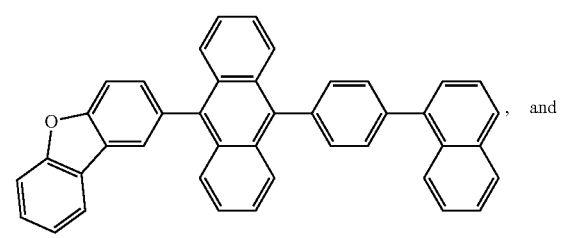
EM318
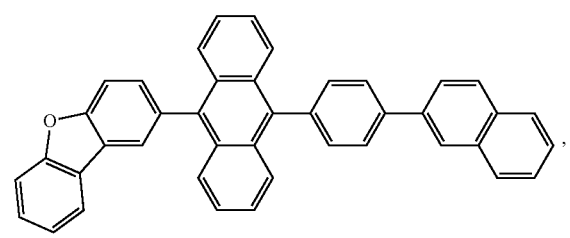, and
EM317
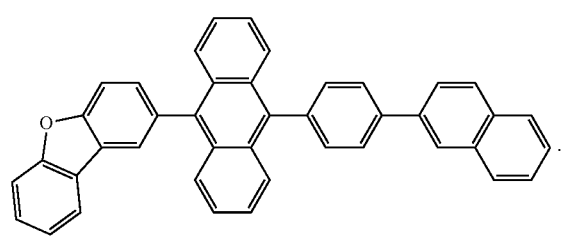
18. The organic electroluminescence device according to claim 14, wherein the anthracene derivative is the following compound:

EM311
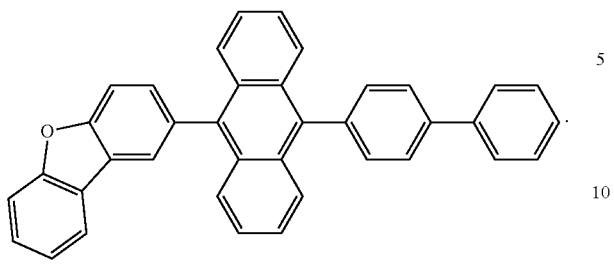
* * * * *